(12) United States Patent
Zeiner et al.

(10) Patent No.: US 10,349,940 B2
(45) Date of Patent: Jul. 16, 2019

(54) SURGICAL STAPLER BUTTRESS APPLICATOR WITH STATE INDICATOR

(71) Applicant: Ethicon Endo-Surgery, LLC, Guaynabo, PR (US)

(72) Inventors: Mark S. Zeiner, Mason, OH (US); Trevor J. Barton, Cincinnati, OH (US); Michael J. Vendely, Lebanon, OH (US); Jason L. Harris, Lebanon, OH (US); Emily A. Schellin, Cincinnati, OH (US); Frederick E. Shelton, IV, Hillsboro, OH (US); Charles J. Scheib, Loveland, OH (US); Prudence A. Turner, Independence, KY (US)

(73) Assignee: Ethicon LLC, Guaynabo, PR (US)

( * ) Notice: Subject to any disclaimer, the term of this patent is extended or adjusted under 35 U.S.C. 154(b) by 514 days.

(21) Appl. No.: 14/926,358

(22) Filed: Oct. 29, 2015

(65) Prior Publication Data

US 2017/0056018 A1 Mar. 2, 2017

Related U.S. Application Data

(60) Provisional application No. 62/209,041, filed on Aug. 24, 2015.

(51) Int. Cl.
*A61B 17/10* (2006.01)
*A61B 17/04* (2006.01)
(Continued)

(52) U.S. Cl.
CPC .......... *A61B 17/105* (2013.01); *A61B 17/068* (2013.01); *A61B 17/07292* (2013.01);
(Continued)

(58) Field of Classification Search
CPC ..... A61B 17/068; A61B 17/105; A61B 17/32; A61B 17/34
(Continued)

(56) References Cited

U.S. PATENT DOCUMENTS

| 4,805,823 A | 2/1989 | Rothfuss |
| 5,415,334 A | 5/1995 | Williamson et al. |

(Continued)

FOREIGN PATENT DOCUMENTS

| CN | 104 379 068 A | 2/2015 |
| EP | 2 090 248 A2 | 8/2009 |

(Continued)

OTHER PUBLICATIONS

European Search Report and Written Opinion dated Jan. 30, 2017 for Application No. EP 16185376.7, 14 pgs.

(Continued)

*Primary Examiner* — Robert F Long
(74) *Attorney, Agent, or Firm* — Frost Brown Todd LLC

(57) ABSTRACT

An apparatus includes a housing, a platform, a buttress assembly, at least one retainer member, and an indicator. A portion of the platform is exposed in a gap defined by the housing. The buttress assembly is exposed in the gap defined by the housing. The retainer member is configured to selectively retain the buttress assembly against the platform. The retainer member is further configured to release the buttress assembly from the platform in response to a clamping action of an end effector positioned in the gap defined by the housing. The indicator is configured to provide indication of a state of one or both of the buttress assembly or the at least one retainer member. The indicator is further configured to change state in response to a change of state of one or both of the buttress assembly or the at least one retainer member.

20 Claims, 25 Drawing Sheets

(51) Int. Cl.
  *A61B 17/072* (2006.01)
  *A61B 50/30* (2016.01)
  *A61B 17/068* (2006.01)
  *A61B 17/32* (2006.01)
  *A61B 17/34* (2006.01)
  *A61B 17/00* (2006.01)
  *A61B 90/00* (2016.01)
  *A61B 50/00* (2016.01)
  *A61B 34/30* (2016.01)
  *A61B 50/31* (2016.01)

(52) U.S. Cl.
  CPC .............. *A61B 17/32* (2013.01); *A61B 17/34* (2013.01); *A61B 50/30* (2016.02); *A61B 17/07207* (2013.01); *A61B 34/30* (2016.02); *A61B 50/31* (2016.02); *A61B 2017/0042* (2013.01); *A61B 2017/0053* (2013.01); *A61B 2017/00115* (2013.01); *A61B 2017/00477* (2013.01); *A61B 2017/00734* (2013.01); *A61B 2017/00951* (2013.01); *A61B 2017/07257* (2013.01); *A61B 2050/005* (2016.02); *A61B 2050/0059* (2016.02); *A61B 2050/314* (2016.02); *A61B 2090/037* (2016.02); *A61B 2090/081* (2016.02); *A61B 2090/0811* (2016.02); *A61B 2090/0814* (2016.02)

(58) Field of Classification Search
  USPC ............................................ 227/175.1–182.1
  See application file for complete search history.

(56) References Cited

U.S. PATENT DOCUMENTS

| | | | |
|---|---|---|---|
| 5,441,191 A * | 8/1995 | Linden | B25C 5/1689 227/120 |
| 5,465,895 A | 11/1995 | Knodel et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,752,965 A | 5/1998 | Francis et al. | |
| 5,792,135 A | 8/1998 | Madhani et al. | |
| 5,814,055 A | 9/1998 | Knodel et al. | |
| 5,817,084 A | 10/1998 | Jensen | |
| 5,878,193 A | 3/1999 | Wang et al. | |
| 6,231,565 B1 | 5/2001 | Tovey et al. | |
| 6,273,897 B1 | 8/2001 | Dalessandro et al. | |
| 6,364,888 B1 | 4/2002 | Niemeyer et al. | |
| 6,783,524 B2 | 8/2004 | Anderson et al. | |
| 6,939,358 B2 | 9/2005 | Palacios et al. | |
| 6,978,921 B2 | 12/2005 | Shelton, IV et al. | |
| 7,000,818 B2 | 2/2006 | Shelton, IV et al. | |
| 7,143,923 B2 | 12/2006 | Shelton, IV et al. | |
| 7,303,108 B2 | 12/2007 | Shelton, IV | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,524,320 B2 | 4/2009 | Tierney | |
| 7,691,098 B2 | 4/2010 | Wallace | |
| 7,721,930 B2 | 5/2010 | McKenna et al. | |
| 7,806,891 B2 | 10/2010 | Nowlin et al. | |
| 8,141,762 B2 | 3/2012 | Bedi et al. | |
| 8,210,411 B2 | 7/2012 | Yates et al. | |
| 8,371,491 B2 | 2/2013 | Huitema et al. | |
| 8,408,439 B2 | 4/2013 | Huang et al. | |
| 8,453,914 B2 | 6/2013 | Laurent et al. | |
| 8,479,969 B2 | 7/2013 | Shelton, IV | |
| 8,573,461 B2 | 11/2013 | Shelton, IV et al. | |
| 8,573,465 B2 | 11/2013 | Shelton, IV | |
| 8,602,288 B2 | 12/2013 | Shelton, IV et al. | |
| 8,616,431 B2 | 12/2013 | Timm et al. | |
| 8,783,541 B2 | 7/2014 | Shelton, IV et al. | |
| 8,800,838 B2 | 8/2014 | Shelton, IV | |
| 8,801,735 B2 | 8/2014 | Shelton, IV et al. | |
| 8,814,025 B2 | 8/2014 | Miller et al. | |
| 8,820,605 B2 | 9/2014 | Shelton, IV | |
| 8,844,789 B2 | 9/2014 | Shelton, IV et al. | |
| 8,899,464 B2 | 12/2014 | Hueil et al. | |
| 8,998,060 B2 | 4/2015 | Bruewer et al. | |
| 9,060,770 B2 | 6/2015 | Shelton, IV et al. | |
| 9,101,359 B2 | 8/2015 | Smith et al. | |
| 9,186,142 B2 | 11/2015 | Fanelli et al. | |
| 9,198,644 B2 | 12/2015 | Balek et al. | |
| 9,198,662 B2 | 12/2015 | Barton et al. | |
| 9,211,120 B2 | 12/2015 | Scheib et al. | |
| 9,220,501 B2 | 12/2015 | Baxter, III et al. | |
| 9,282,962 B2 | 3/2016 | Schmid et al. | |
| 9,301,759 B2 | 4/2016 | Spivey et al. | |
| 9,307,965 B2 | 4/2016 | Ming et al. | |
| 9,364,233 B2 | 6/2016 | Alexander, III et al. | |
| 9,393,018 B2 | 7/2016 | Wang et al. | |
| 9,398,911 B2 | 7/2016 | Auld | |
| 9,445,808 B2 | 9/2016 | Woodard et al. | |
| 9,492,170 B2 | 11/2016 | Bear et al. | |
| 9,517,065 B2 | 12/2016 | Simms et al. | |
| 9,770,245 B2 | 9/2017 | Swayze et al. | |
| 10,052,105 B2 | 8/2018 | Tannhauser et al. | |
| 2005/0070929 A1 | 3/2005 | Dalessandro et al. | |
| 2006/0173470 A1 | 8/2006 | Oray et al. | |
| 2008/0169328 A1 | 7/2008 | Shelton, IV | |
| 2009/0206126 A1 * | 8/2009 | Huitema | A61B 17/07207 227/175.1 |
| 2009/0206131 A1 | 8/2009 | Weisenburgh, II et al. | |
| 2010/0234861 A1 | 9/2010 | Oray et al. | |
| 2011/0290856 A1 | 12/2011 | Shelton, IV et al. | |
| 2012/0241492 A1 | 9/2012 | Shelton, IV et al. | |
| 2012/0241493 A1 | 9/2012 | Baxter, III et al. | |
| 2012/0292367 A1 | 11/2012 | Morgan et al. | |
| 2013/0062391 A1 | 3/2013 | Boudreaux et al. | |
| 2013/0068816 A1 | 3/2013 | Vasudevan et al. | |
| 2013/0075447 A1 * | 3/2013 | Weisenburgh, II | A61B 17/00491 227/176.1 |
| 2013/0206813 A1 | 8/2013 | Nalagatla | |
| 2013/0214030 A1 | 8/2013 | Aronhalt et al. | |
| 2014/0239036 A1 | 8/2014 | Zerkle et al. | |
| 2014/0239037 A1 | 8/2014 | Boudreaux et al. | |
| 2014/0239038 A1 | 8/2014 | Leimbach et al. | |
| 2014/0239040 A1 | 8/2014 | Fanelli et al. | |
| 2014/0239041 A1 | 8/2014 | Zerkle et al. | |
| 2014/0239043 A1 | 8/2014 | Simms et al. | |
| 2014/0239044 A1 | 8/2014 | Hoffman | |
| 2014/0263563 A1 | 9/2014 | Stokes et al. | |
| 2015/0272575 A1 | 10/2015 | Leimbach et al. | |
| 2015/0351754 A1 | 12/2015 | Harris et al. | |
| 2015/0351758 A1 | 12/2015 | Shelton, IV et al. | |
| 2015/0351763 A1 | 12/2015 | Shelton, IV et al. | |
| 2015/0374360 A1 | 12/2015 | Scheib et al. | |
| 2015/0374373 A1 | 12/2015 | Rector et al. | |
| 2016/0089142 A1 | 3/2016 | Harris et al. | |
| 2016/0089146 A1 | 3/2016 | Harris et al. | |
| 2016/0278774 A1 | 9/2016 | Shelton, IV et al. | |
| 2017/0027567 A1 | 2/2017 | Scheib et al. | |
| 2017/0027568 A1 | 2/2017 | Scheib et al. | |
| 2017/0027569 A1 | 2/2017 | Scheib et al. | |
| 2017/0049444 A1 | 2/2017 | Schellin et al. | |
| 2017/0055980 A1 | 3/2017 | Vendely et al. | |
| 2017/0055981 A1 | 3/2017 | Vendely et al. | |
| 2017/0055982 A1 | 3/2017 | Zeiner et al. | |
| 2017/0055986 A1 | 3/2017 | Harris et al. | |
| 2017/0056016 A1 | 3/2017 | Barton et al. | |
| 2017/0056017 A1 | 3/2017 | Vendely et al. | |

FOREIGN PATENT DOCUMENTS

| | | |
|---|---|---|
| EP | 2 764 833 A2 | 8/2014 |
| EP | 3 072 457 A2 | 9/2016 |
| EP | 3072460 A2 | 9/2016 |

(56) References Cited

FOREIGN PATENT DOCUMENTS

WO    WO 2005/079675 A2    9/2005
WO    WO 2013/119365 A1    8/2013

OTHER PUBLICATIONS

European Search Report and Written Opinion dated Jan. 24, 2017 for Application No. EP 16185387.4, 10 pgs.
International Search Report and Written Opinion dated Dec. 23, 2016 for Application No. PCT/US2016/048352, 16 pgs.
International Search Report and Written Opinion dated Feb. 17, 2017 for Application No. PCT/US2016/048356, 17 pgs.
International Search Report and Written Opinion dated Jan. 2, 2017 for Application No. PCT/US2016/048359, 12 pgs.
International Search Report and Written Opinion dated Dec. 21, 2016 for Application No. PCT/US2016/048362, 11 pgs.
International Search Report and Written Opinion dated Dec. 6, 2016 for Application No. PCT/US2016/048364, 12 pgs.
U.S. Appl. No. 14/871,071, filed Sep. 30, 2015.
U.S. Appl. No. 14/871,131, filed Sep. 30, 2015.
U.S. Appl. No. 14/926,027, filed Oct. 29, 2015.
U.S. Appl. No. 14/926,029, filed Oct. 29, 2015.
U.S. Appl. No. 14/926,045, filed Oct. 29, 2015.
U.S. Appl. No. 14/926,057, filed Oct. 29, 2015.
U.S. Appl. No. 14/926,072, filed Oct. 29, 2015.
U.S. Appl. No. 14/926,090, filed Oct. 29, 2015.
U.S. Appl. No. 14/926,131, filed Oct. 29, 2015.
U.S. Appl. No. 14/926,160, filed Oct. 29, 2016.
U.S. Appl. No. 14/926,194, filed Oct. 29, 2015.
U.S. Appl. No. 62/209,041, filed Aug. 24, 2015.
U.S. Appl. No. 14/926,267.
U.S. Appl. No. 14/926,296.
U.S. Appl. No. 14/926,322.
U.S. Appl. No. 14/926,609.
U.S. Appl. No. 14/926,764.
Extended European Search Report and Written Opinion dated Jan. 20, 2017 for Application No. EP 16185368.4, 10 pgs.
Extended European Search Report and Written Opinion dated Jan. 24, 2017 for Application No. EP 16185370.0, 11 pgs.
Extended European Search Report and Written Opinion dated Jun. 8, 2017 for Application No. EP 16185375.9, 16 pgs.
European Search Report, Extended, and Written Opinion dated Oct. 18, 2017 for Application No. EP 18182626.4, 8 pgs.
European Examination Report dated Jan. 3, 2018 for Application No. EP 16185368.4, 4pgs.
European Examination Report dated Oct. 16, 2018 for Application No. EP 16185368.4, 4 pgs.
European Examination Report dated Jan. 15, 2018 for Application No. EP 16185370.0, 4 pgs.

* cited by examiner

SURGICAL STAPLER BUTTRESS APPLICATOR WITH STATE INDICATOR

PRIORITY

This application claims priority to U.S. Patent App. No. 62/209,041, entitled "Method and Apparatus for Applying a Buttress to End Effector of a Surgical Stapler," filed Aug. 24, 2015, the disclosure of which is incorporated by reference herein.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited for use through a thoracotomy are disclosed in U.S. Patent Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015; U.S. Patent Pub. No. 2014/0239041, entitled "Lockout Feature for Movable Cutting Member of Surgical Instrument," published Aug. 28, 2014, issued as U.S. Pat. No. 9,717,497 on Aug. 1, 2017; U.S. Patent Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; U.S. Patent Pub. No. 2014/0239036, entitled "Jaw Closure Feature for End Effector of Surgical Instrument," published Aug. 28, 2014, issued as U.S. Pat. No. 9,839,421 on Dec. 12, 2017; U.S. Patent Pub. No. 2014/0239040, entitled "Surgical Instrument with Articulation Lock having a Detenting Binary Spring," published Aug. 28, 2014, issued as U.S. Pat. No. 9,867,615 on Jan. 16, 2018; U.S. Patent Pub. No. 2014/0239043, entitled "Distal Tip Features for End Effector of Surgical Instrument," published Aug. 28, 2014, issued as U.S. Pat. No. 9,622,746 on Apr. 18, 2017; U.S. Patent Pub. No. 2014/0239037, entitled "Staple Forming Features for Surgical Stapling Instrument," published Aug. 28, 2014, issued as U.S. Pat. No. 10,092,292 on Oct. 9, 2018; U.S. Patent Pub. No. 2014/0239038, entitled "Surgical Instrument with Multi-Diameter Shaft," published Aug. 28, 2014, issued as U.S. Pat. No. 9,795,379 on Oct. 24, 2017; and U.S. Patent Pub. No. 2014/0239044, entitled "Installation Features for Surgical Instrument End Effector Cartridge," published Aug. 28, 2014, issued as U.S. Pat. No. 9,808,248 on Nov. 7, 2017. The disclosure of each of the above-cited U.S. Patent Publications is incorporated by reference herein.

Additional surgical stapling instruments are disclosed in U.S. Pat. No. 8,801,735, entitled "Surgical Circular Stapler with Tissue Retention Arrangements," issued Aug. 12, 2014; U.S. Pat. No. 8,141,762, entitled "Surgical Stapler Comprising a Staple Pocket," issued Mar. 27, 2012; U.S. Pat. No. 8,371,491, entitled "Surgical End Effector Having Buttress Retention Features," issued Feb. 12, 2013; U.S. Pub. No. 2014/0263563, entitled "Method and Apparatus for Sealing End-to-End Anastomosis" published Sep. 18, 2014, issued as U.S. Pat. No. 9,597,082 on Mar. 3, 2017; U.S. Pub. No. 2014/0246473, entitled "Rotary Powered Surgical Instruments with Multiple Degrees of Freedom," published Sep. 4, 2014, issued as U.S. Pat. No. 9,398,911 on Jul. 26, 2016; U.S. Pub. No. 2013/0206813, entitled "Linear Stapler," published Aug. 15, 2013, now abandoned; U.S. Pub. No. 2008/0169328, entitled "Buttress Material for Use with a Surgical Stapler," published Jul. 17, 2008, now abandoned; U.S. patent application Ser. No. 14/300,804, entitled "Woven and Fibrous Materials for Reinforcing a Staple Line," filed Jun. 10, 2014, issued as U.S. Pat. No. 9,848,871 on Dec. 26, 2017; U.S. patent application Ser. No. 14/300,811, entitled "Devices and Methods for Sealing Staples in Tissue" 2014, issued as U.S. Pat. No. 9,936,954 on Apr. 10, 2018; and U.S. patent application Ser. No. 14/498,070, entitled "Radically Expandable Staple Line" filed Sep. 26, 2014, published as U.S. Pub. No. 2016/0089146. The disclosure of each of the above-cited U.S. Patents, U.S. Patent Publications, and U.S. Patent Applications is incorporated by reference herein.

In some instances, it may be desirable to equip a surgical stapling instrument with a buttress material to reinforce the mechanical fastening of tissue provided by staples. Such a buttress may prevent the applied staples from pulling through tissue and may otherwise reduce a risk of tissue tearing at or near the site of applied staples.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
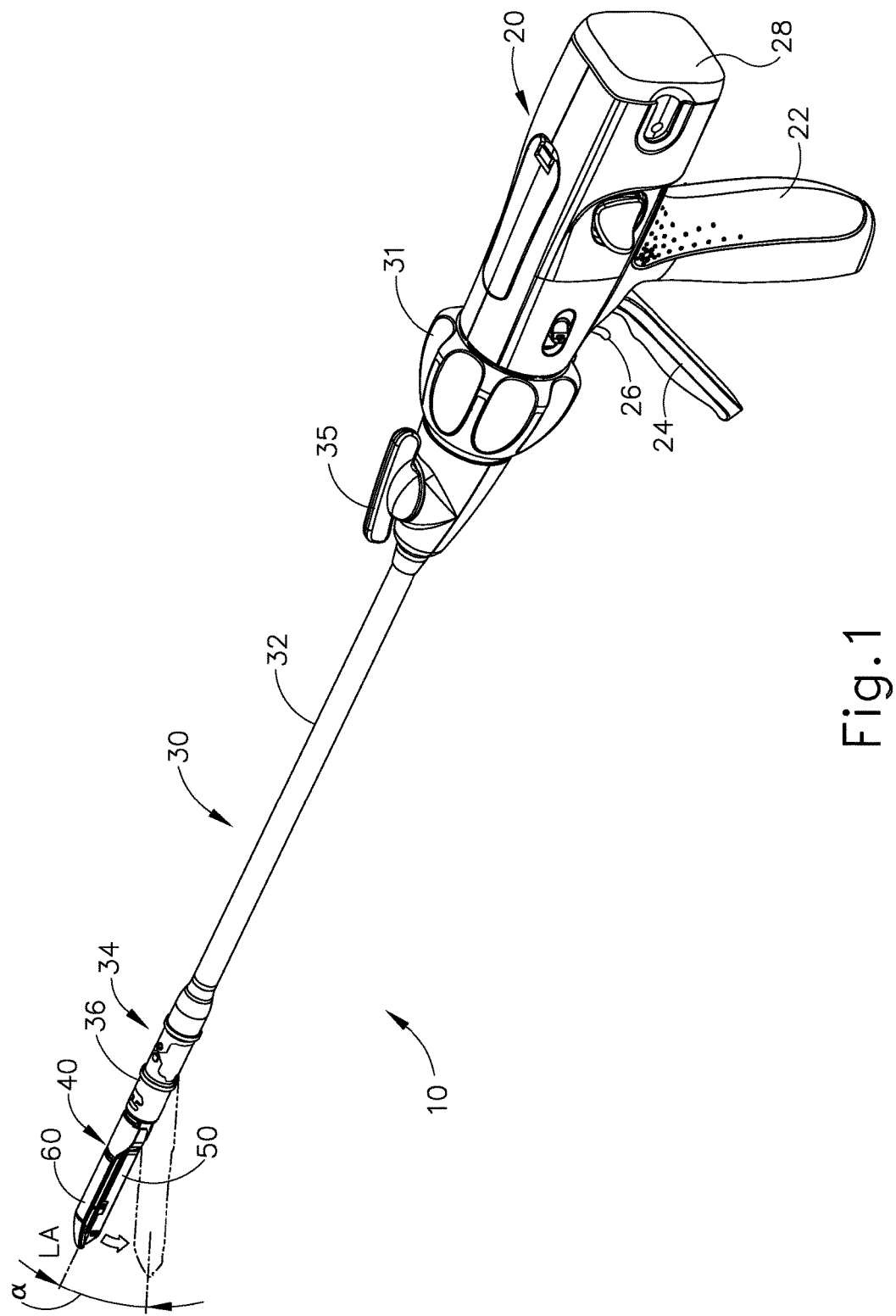
FIG. 1 depicts a perspective view of an exemplary articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIG. 1 depicts an exemplary surgical stapling and severing instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, end effector (40) and the distal portion of shaft assembly (30) may be inserted directly through a thoracotomy or other type of incision. It should be understood that terms such as "proximal" and "distal" are used herein with reference to a clinician gripping handle assembly (20) of instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

A. Exemplary Handle Assembly and Shaft Assembly

As shown in FIG. 1, handle assembly (20) of the present example comprises pistol grip (22), a closure trigger (24), and a firing trigger (26). Each trigger (24, 26) is selectively pivotable toward and away from pistol grip (22) as will be described in greater detail below. Handle assembly (20) further includes a removable battery pack (28). These components will also be described in greater detail below. Of course, handle assembly (20) may have a variety of other components, features, and operabilities, in addition to or in lieu of any of those noted above. Other suitable configurations for handle assembly (20) will be apparent to those of ordinary skill in the art in view of the teachings herein.

Figure 2:
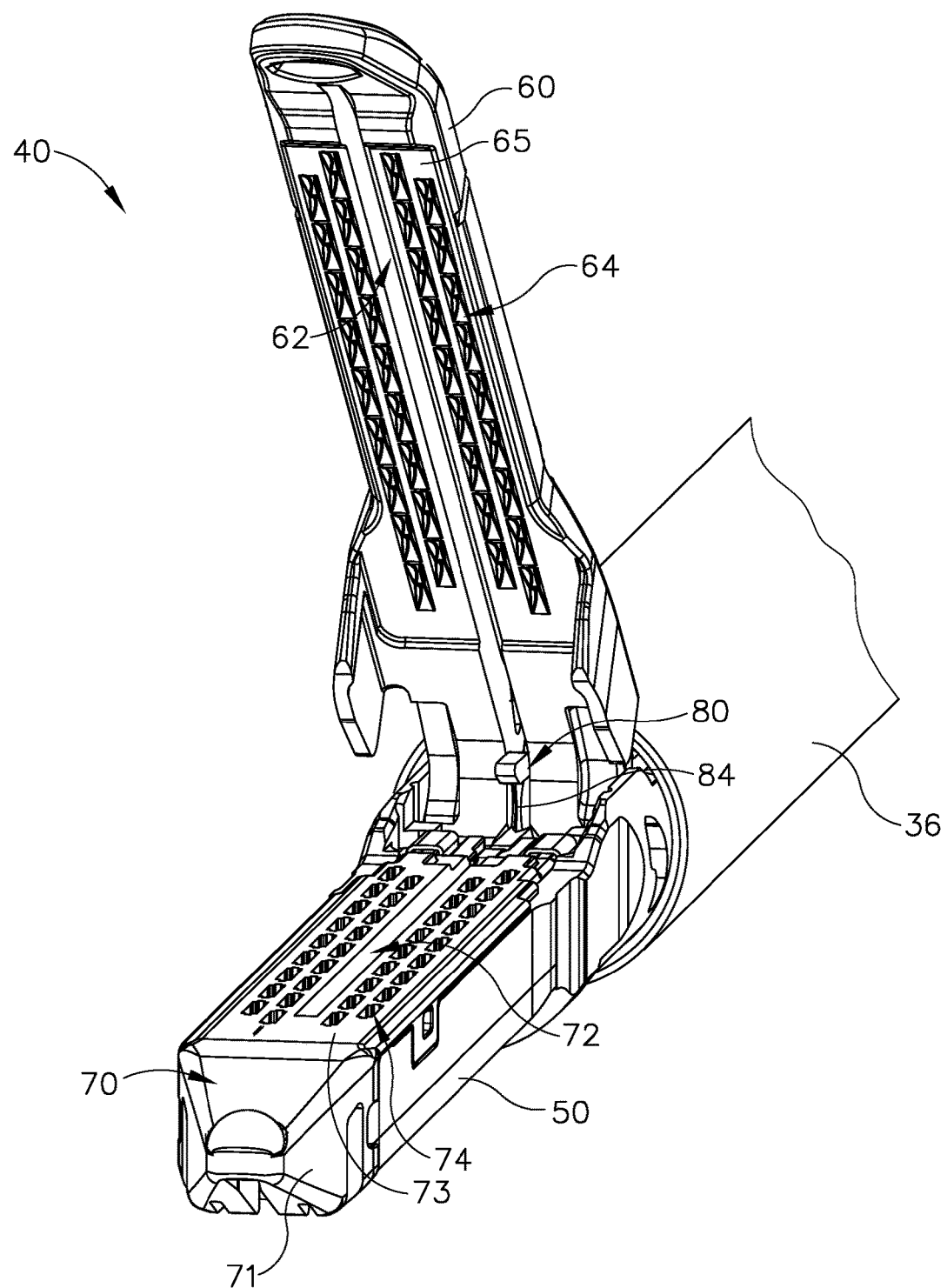
FIG. 2 depicts a perspective view of an end effector of the instrument of FIG. 1, with the end effector in an open configuration.

As shown in FIGS. 1-2, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34). Exemplary features that may be used to provide longitudinal translation of closure tube (32) and closure ring (36) will be described in greater detail below.

Articulation section (34) is operable to laterally deflect closure ring (36) and end effector (40) laterally away from the longitudinal axis (LA) of shaft assembly (30) at a desired angle (a). In the present example, articulation is controlled through an articulation control knob (35) which is located at the proximal end of shaft assembly (30). Closure ring (36) and end effector (40) pivot about an axis that is perpendicular to the longitudinal axis (LA) of shaft assembly (30) in response to rotation of knob (35). Articulation section (34) is configured to communicate longitudinal translation of closure tube (32) to closure ring (36), regardless of whether articulation section (34) is in a straight configuration or an articulated configuration. By way of example only, articulation section (34) and/or articulation control knob (35) may be constructed and operable in accordance with at least some of the teachings of U.S. Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015, the disclosure of which is incorporated by reference herein; and/or U.S. patent application Ser. No. 14/314,125, entitled "Articulation Drive Features for Surgical Stapler," filed Jun. 25, 2014, published as U.S. Pub. No. 2015/0374360 on Dec. 31, 2015, the disclosure of which is incorporated by reference herein; and/or in accordance with the various teachings below. Other suitable forms that articulation section (34) and articulation knob (35) may take will be apparent to those of ordinary skill in the art in view of the teachings herein.

As shown in FIG. 1, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). Of course, shaft assembly (30) may have a variety of other components, features, and operabilities, in addition to or in lieu of any of those noted above. By way of example only, at least part of shaft assembly (30) is constructed in accordance with at least some of the teachings of U.S. Pub. No. 2014/0239038, entitled "Surgical Instrument with Multi-Diameter Shaft," published Aug. 28, 2014, issued as U.S. Pat. No. 9,795,379 on Oct. 24, 2017, the disclosure of which is incorporated by reference herein. Other suitable configurations for shaft assembly (30) will be apparent to those of ordinary skill in the art in view of the teachings herein.

B. Exemplary End Effector

Figure 3:
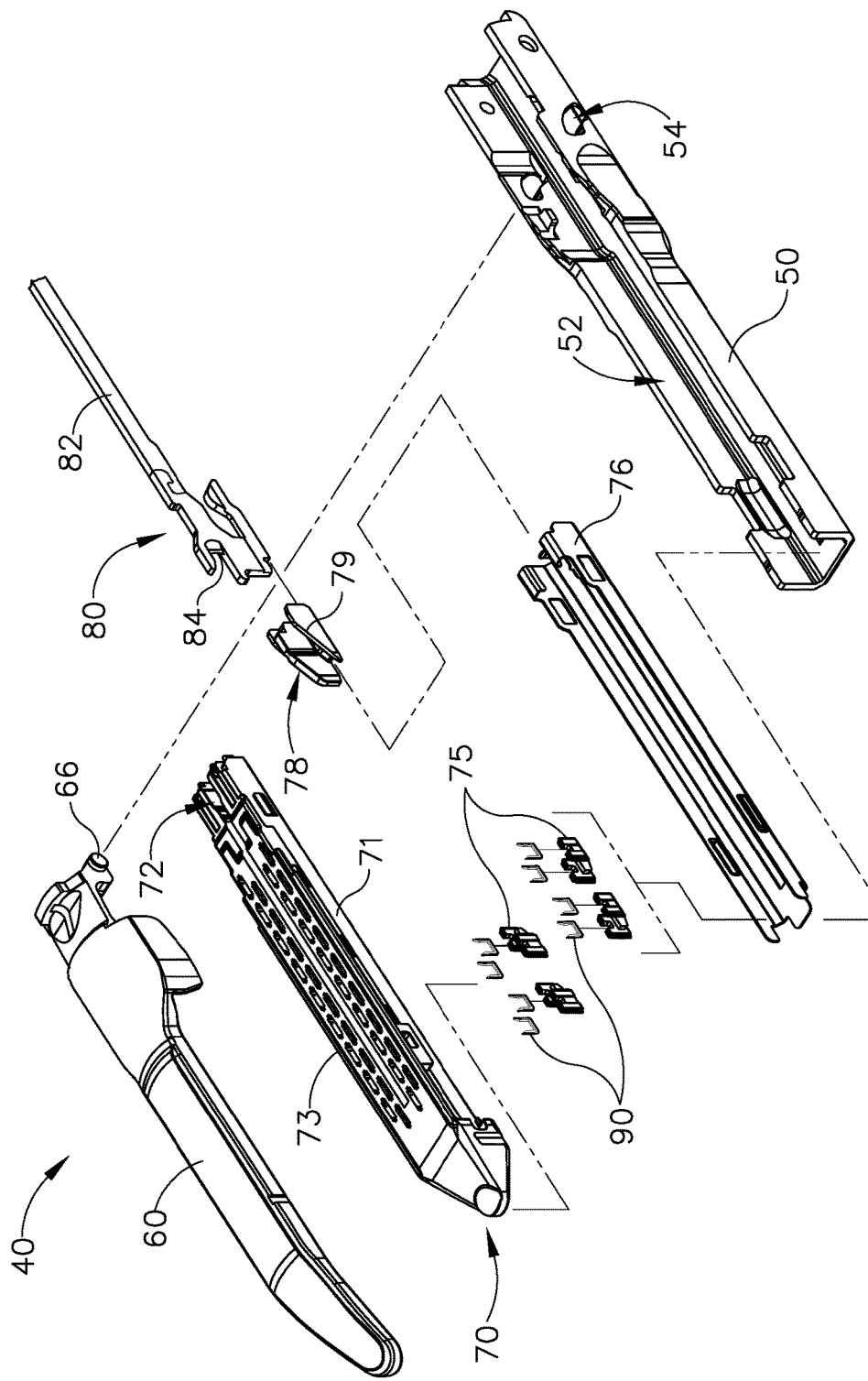
FIG. 3 depicts an exploded perspective view of the end effector of FIG. 2.

As also shown in FIGS. 1-3, end effector (40) of the present example includes a lower jaw (50) and a pivotable anvil (60). Anvil (60) includes a pair of integral, outwardly extending pins (66) that are disposed in corresponding curved slots (54) of lower jaw (50). Anvil (60) is pivotable toward and away from lower jaw (50) between an open position (shown in FIG. 2) and a closed position (shown in FIG. 1). Use of the term "pivotable" (and similar terms with "pivot" as a base) should not be read as necessarily requiring pivotal movement about a fixed axis. For instance, in the present example, anvil (60) pivots about an axis that is defined by pins (66), which slide along curved slots (54) of lower jaw (50) as anvil (60) moves toward lower jaw (50). In such versions, the pivot axis translates along the path defined by slots (54) while anvil (60) simultaneously pivots about that axis. In addition or in the alternative, the pivot axis may slide along slots (54) first, with anvil (60) then pivoting about the pivot axis after the pivot axis has slid a certain distance along the slots (54). It should be understood that such sliding/translating pivotal movement is encompassed within terms such as "pivot," "pivots," "pivotal," "pivotable," "pivoting," and the like. Of course, some versions may provide pivotal movement of anvil (60) about an axis that remains fixed and does not translate within a slot or channel, etc.

As best seen in FIG. 3, lower jaw (50) of the present example defines a channel (52) that is configured to receive a staple cartridge (70). Staple cartridge (70) may be inserted into channel (52), end effector (40) may be actuated, and then staple cartridge (70) may be removed and replaced with another staple cartridge (70). Lower jaw (50) thus releasably retains staple cartridge (70) in alignment with anvil (60) for actuation of end effector (40). In some versions, lower jaw (50) is constructed in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Other suitable forms that lower jaw (50) may take will be apparent to those of ordinary skill in the art in view of the teachings herein.

As best seen in FIGS. 2-3, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (90) is positioned in each staple pocket (74). A staple driver (75) is also positioned in each staple pocket (74), underneath a corresponding staple (90), and above tray (76). As will be described in greater detail below, staple drivers (75) are operable to translate upwardly in staple pockets (74) to thereby drive staples (90) upwardly through staple pockets (74) and into engagement with anvil (60). Staple drivers (75) are driven upwardly by a wedge sled (78), which is captured between cartridge body (71) and tray (76), and which translates longitudinally through cartridge body (71).

Wedge sled (78) includes a pair of obliquely angled cam surfaces (79), which are configured to engage staple drivers (75) and thereby drive staple drivers (75) upwardly as wedge sled (78) translates longitudinally through cartridge (70). For instance, when wedge sled (78) is in a proximal position, staple drivers (75) are in downward positions and staples (90) are located in staple pockets (74). As wedge sled (78) is driven to the distal position by a translating knife member (80), wedge sled (78) drives staple drivers (75) upwardly, thereby driving staples (90) out of staple pockets (74) and into staple forming pockets (64) that are formed in the underside (65) of anvil (60). Thus, staple drivers (75) translate along a vertical dimension as wedge sled (78) translates along a horizontal dimension.

In some versions, staple cartridge (70) is constructed and operable in accordance with at least some of the teachings of U. U.S. Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016, the disclosure of which is incorporated by reference herein. In addition or in the alternative, staple cartridge (70) may be constructed and operable in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Other suitable forms that staple cartridge (70) may take will be apparent to those of ordinary skill in the art in view of the teachings herein.

As best seen in FIG. 2, anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (90) when staples (90) are driven through tissue and into anvil (60). In particular, staple forming pockets (64) are configured to bend the legs of staples (90) to secure the formed staples (90) in the tissue. Anvil (60) may be constructed in accordance with at least some of the teachings of U.S. Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017; and/or at least some of the teachings of U.S. Pub. No. 2014/0239037, entitled "Staple Forming Features for Surgical Stapling Instrument," published Aug. 28, 2014, issued as U.S. Pat. No. 10,092,292 on Oct. 9, 2018, the disclosure of which is incorporated by reference herein. Other suitable forms that anvil (60) may take will be apparent to those of ordinary skill in the art in view of the teachings herein.

In the present example, a knife member (80) is configured to translate through end effector (40). As best seen in FIG. 3, knife member (80) is secured to the distal end of a firing beam (82), which extends through a portion of shaft assembly (30). As best seen in FIG. 2, knife member (80) is positioned in channels (62, 72) of anvil (60) and staple cartridge (70). Knife member (80) includes a distally presented cutting edge (84) that is configured to sever tissue that is compressed between anvil (60) and deck (73) of staple cartridge (70) as knife member (80) translates distally through end effector (40). As noted above, knife member (80) also drives wedge sled (78) distally as knife member (80) translates distally through end effector (40), thereby driving staples (90) through tissue and against anvil (60) into formation.

C. Exemplary Actuation of End Effector

In the present example, anvil (60) is driven toward lower jaw (50) by advancing closure ring (36) distally relative to end effector (40). Closure ring (36) cooperates with anvil (60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40). By way of example only, closure ring (36) and anvil (60) may interact in accordance with at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017, the disclosure of which is incorporated by reference herein; and/or in accordance with at least some of the teachings of U.S. patent application Ser. No. 14/314,108, entitled "Jaw Opening Feature for Surgical Stapler," filed on Jun. 25, 2014, published as U.S. Pub. No. 2015/0374373 on Dec. 31, 2015, the disclosure of which is incorporated by reference herein.

As noted above, handle assembly (20) includes a pistol grip (22) and a closure trigger (24). As also noted above, anvil (60) is closed toward lower jaw (50) in response to distal advancement of closure ring (36). In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein.

Also in the present example, instrument (10) provides motorized control of firing beam (82). In particular, instrument (10) includes motorized components that are configured to drive firing beam (82) distally in response to pivoting of firing trigger (26) toward pistol grip (22). In some versions, a motor (not shown) is contained in pistol grip (22) and receives power from battery pack (28). This motor is coupled with a transmission assembly (not shown) that converts rotary motion of a drive shaft of the motor into linear translation of firing beam (82). By way of example only, the features that are operable to provide motorized actuation of firing beam (82) may be configured and operable in accordance with at least some of the teachings of U.S. Pat. No. 8,210,411, entitled "Motor-Driven Surgical Instrument," issued Jul. 3, 2012, the disclosure of which is incorporated by reference herein; U.S. Pat. No. 8,453,914, entitled "Motor-Driven Surgical Cutting Instrument with Electric Actuator Directional Control Assembly," issued Jun. 4, 2013, the disclosure of which is incorporated by reference herein; and/or U.S. patent application Ser. No. 14/226,142, entitled "Surgical Instrument Comprising a Sensor System," filed Mar. 26, 2014, issued as U.S. Pat. No. 9,913,642 on Mar. 13, 2018, the disclosure of which is incorporated by reference herein.

It should also be understood that any other components or features of instrument (10) may be configured and operable in accordance with any of the various references cited herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should therefore be understood that the teachings below may be readily incorporated into the various instruments taught in the various references that are cited herein. It should also be understood that the below teachings are not limited to instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Buttress Assembly for Surgical Stapler

In some instances, it may be desirable to equip end effector (40) with a buttress material to reinforce the mechanical fastening of tissue provided by staples (90). Such a buttress may prevent the applied staples (90) from pulling through the tissue and may otherwise reduce a risk of tissue tearing at or near the site of applied staples (90). In addition to or as an alternative to providing structural support and integrity to a line of staples (90), a buttress may provide various other kinds of effects such as spacing or gap-filling, administration of therapeutic agents, and/or other effects. In some instances, a buttress may be provided on deck (73) of staple cartridge (70). In some other instances, a buttress may be provided on the surface of anvil (60) that faces staple cartridge (70). It should also be understood that a first buttress may be provided on deck (73) of staple cartridge (70) while a second buttress is provided on anvil (60) of the same end effector (40). Various examples of forms that a buttress may take will be described in greater detail below. Various ways in which a buttress may be secured to a staple cartridge (70) or an anvil (60) will also be described in greater detail below.

A. Exemplary Composition of Buttress Assembly for Surgical Stapler

Figure 4:
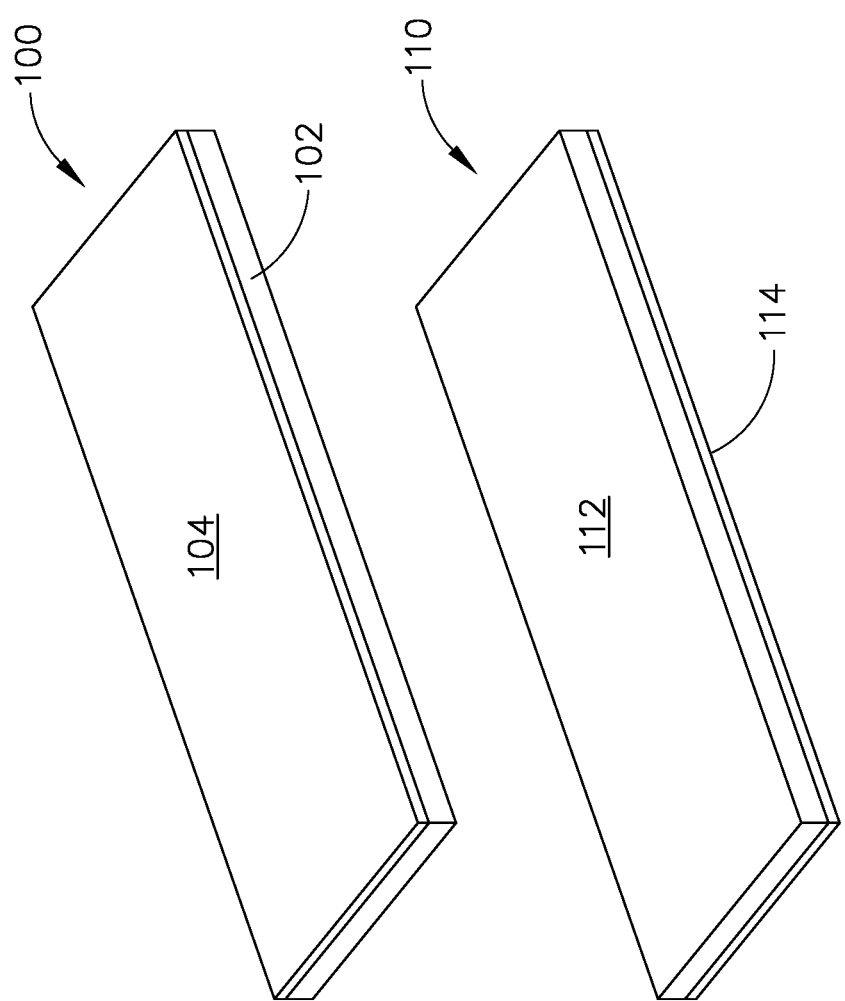
FIG. 4 depicts a perspective view of an exemplary upper buttress and an exemplary lower buttress, each of which may be applied to the end effector of FIG. 2.

FIG. 4 shows an exemplary pair of buttress assemblies (100, 110) with a basic composition. Buttress assembly (100) of this example comprises a buttress body (102) and an upper adhesive layer (104). Similarly, buttress assembly (110) comprises a buttress body (112) and a lower adhesive layer (114). In the present example, each buttress body (102, 112) comprises a strong yet flexible material configured to structurally support a line of staples (90). By way of example only, each buttress body (102, 112) may comprise a woven mesh of polyglactin 910 material by Ethicon, Inc. of Somerville, N.J. Alternatively, any other suitable materials or combinations of materials may be used in addition to or as an alternative to polyglactin 910 material to form each buttress body (102, 112). Each buttress body (102, 112) may take any other suitable form and may be constructed of any other suitable material(s). By way of further example only, each buttress body (102, 112) may comprise one or more of the following: NEOVEIL absorbable PGA felt by Gunze Limited, of Kyoto, Japan; SEAMGUARD polyglycolic acid: trimethylene carbonate (PGA:TMC) reinforcement material by W.L. Gore & Associates, Inc., of Flagstaff, Ariz.; PERI-STRIPS DRY with VERITAS Collagen Matrix (PSDV) reinforcement material, by Baxter Healthcare Corporation of Deerfield, Ill.; BIODESIGN biologic graft material by Cook Medical, Bloomington, Ind.; and/or SURGICEL NU-KNIT hemostat material by Ethicon, Inc. of Somerville, N.J. Still other suitable materials that may be used to form each buttress body (102, 112) will be apparent to those of ordinary skill in the art in view of the teachings herein.

In addition or in the alternative, each buttress body (102, 112) may comprise a material including, for example, a hemostatic agent such as fibrin to assist in coagulating blood and reduce bleeding at the severed and/or stapled surgical site along tissue (90). As another merely illustrative example, each buttress body (102, 112) may comprise other adjuncts or hemostatic agents such as thrombin may be used such that each buttress body (102, 112) may assist to coagulate blood and reduce the amount of bleeding at the surgical site. Other adjuncts or reagents that may be incorporated into each buttress body (102, 112) may further include but are not limited to medical fluid or matrix components. Merely illustrative examples of materials that may be used to form each buttress body (102, 112), as well as materials that may be otherwise incorporated into each buttress body (102, 112), are disclosed in U.S. patent application Ser. No. 14/667,842, entitled "Method of Applying a Buttress to a Surgical Stapler," filed Mar. 25, 2015, published as U.S. Pub. No. 2016/0278774 on Sep. 29, 2016, the disclosure of which is incorporated by reference herein. Alternatively, any other suitable materials may be used.

By way of further example only, each buttress body (102, 112) may be constructed in accordance with at least some of the teachings of U.S. Patent Pub. No. 2012/0241493, entitled "Tissue Thickness Compensator Comprising Controlled Release and Expansion," published Sep. 27, 2012, issued as U.S. Pat. No. 10,123,798 on Nov. 13, 2018, the disclosure of which is incorporated by reference herein; U.S. Patent Pub. No. 2013/0068816, entitled "Surgical Instrument and Buttress Material," published Mar. 21, 2013, now abandoned, the disclosure of which is incorporated by reference herein; U.S. Patent Pub. No. 2013/0062391, entitled "Surgical Instrument with Fluid Fillable Buttress," published Mar. 14, 2013, issued as U.S. Pat. No. 9,999,408 on Mar. 24, 2016, the disclosure of which is incorporated by reference herein; U.S. Patent Pub. No. 2013/0068820, entitled "Fibrin Pad Matrix with Suspended Heat Activated Beads of Adhesive," published Mar. 21, 2013, issued as U.S. Pat. No. 8,814,025 on Aug. 26, 2014, the disclosure of which is incorporated by reference herein; U.S. Patent Pub. No. 2013/0082086, entitled "Attachment of Surgical Staple Buttress to Cartridge," published Apr. 4, 2013, issued as U.S. Pat. No. 8,998,464 on Dec. 2, 2014, the disclosure of which is incorporated by reference herein; U.S. Patent Pub. No. 2013/0037596, entitled "Device for Applying Adjunct in Endoscopic Procedure," published Feb. 14, 2013, issued as U.S. Pat. No. 9,492,170 on Nov. 15, 2016, the disclosure of which is incorporated by reference herein; U.S. Patent Pub. No. 2013/0062393, entitled "Resistive Heated Surgical Staple Cartridge with Phase Change Sealant," published Mar. 14, 2013, issued as U.S. Pat. No. 8,998,060 on Apr. 10, 2015, the disclosure of which is incorporated by reference herein; U.S. Patent Pub. No. 2013/0075446, entitled "Surgical Staple Assembly with Hemostatic Feature," published Mar. 28, 2013, issued as U.S. Pat. No. 9,393,018 on Jul. 19, 2016, the disclosure of which is incorporated by reference herein; U.S. Patent Pub. No. 2013/0062394, entitled "Surgical Staple Cartridge with Self-Dispensing Staple Buttress," published Mar. 14, 2013, issued as U.S. Pat. No. 9,101,359 on Aug. 11, 2015, the disclosure of which is incorporated by reference herein; U.S. Patent Pub. No. 2013/0075445, entitled "Anvil Cartridge for Surgical Fastening Device," published Mar. 28, 2013, issued as U.S. Pat. No. 9,198,644 on Dec. 1, 2015, the disclosure of which is incorporated by reference herein; U.S. Patent Pub. No. 2013/0075447, entitled "Adjunct Therapy for Applying Hemostatic Agent," published Mar. 28, 2013, now abandoned, the disclosure of which is incorporated by reference herein; U.S. Patent Pub. No. 2013/0256367, entitled "Tissue Thickness Compensator Comprising a Plurality of Medicaments," published Oct. 3, 2013, issued as U.S. Pat. No. 9,211,120 on Dec. 15, 2015, the disclosure of which is incorporated by reference herein; U.S. patent application Ser. No. 14/300,954, entitled "Adjunct Materials and Methods of Using Same in Surgical Methods for Tissue Sealing," filed Jun. 10, 2014, issued as U.S. Pat. No. 10,172,611 on Jan. 8, 2019, the disclosure of which is incorporated by reference herein; U.S. patent application Ser. No. 14/827,856, entitled "Implantable Layers for a Surgical Instrument," filed Aug. 17, 2015, published as U.S. Pub. No. 2017/0049444 on Feb. 23, 2017, the disclosure of which is incorporated by reference herein; U.S. patent application Ser. No. 14/840,613, entitled "Drug Eluting Adjuncts and Methods of Using Drug Eluting Adjuncts," filed Aug. 31, 2015, published as U.S. Pub. No. 2017/0055986 on Mar. 2, 2017, the disclosure of which is incorporated by reference herein; U.S. patent application Ser. No. 14/871,071, entitled "Compressible Adjunct with Crossing Spacer Fibers," filed Sep. 30, 2015, published as U.S. Pub. No. 2017/0086837 on Mar. 30, 2017, the disclosure of which is incorporated by reference herein; and/or U.S. patent application Ser. No. 14/871,131, entitled "Method for Applying an Implantable Layer to a Fastener Cartridge," filed Sep. 30, 2015, published as U.S. Pub. No. 2017/0086842 on Mar. 30, 2017, the disclosure of which is incorporated by reference herein.

In the present example, adhesive layer (104) is provided on buttress body (102) in order to adhere buttress body (102) to underside (65) of anvil (60). Similarly, adhesive layer (114) is provided on buttress body (112) in order to adhere buttress body (112) to deck (73) of staple cartridge (70). Adherence of the buttress body (102) to underside (65) of anvil (60) or to deck (73) of staple cartridge (70) can occur through a variety of mechanisms including but not limited to a pressure sensitive adhesive. In some versions, each adhesive layer (104, 114) comprise a pressure sensitive adhesive material. Examples of various suitable materials that may be used to form adhesive layers (104, 114) are disclosed in U.S. patent application Ser. No. 14/667,842, entitled "Method of Applying a Buttress to a Surgical Stapler," filed Mar. 25, 2015, published as U.S. Pub. No. 2016/0278774 on Sep. 29, 2016, the disclosure of which is incorporated by reference herein. Alternatively, any other suitable materials may be used. It should be understood that the term "adhesive," as used herein, may include (but is not limited to) tacky materials and also materials that are pliable or wax-like and adhere to a complex geometry via deformation and conformance. Some suitable adhesives may provide such pliability to adhere to a complex geometry via deformation and conformance without necessarily providing a high initial tack. In some instances, adhesives with lower tackiness may be removed more cleanly from surfaces. Various suitable materials that may be used to form adhesive layers (104, 114) will be apparent to those of ordinary skill in the art in view of the teachings herein.

B. Exemplary Materials and Techniques for Providing Adhesion of Buttress to Surgical Stapler As noted above, a buttress assembly (100, 110) may include a layer (104, 114) of adhesive material (or other form of adhesive material) that adheres buttress body (102, 112) to either underside (65) of anvil (60) or deck (73) of staple cartridge (70). Such an adhesive material may provide proper positioning of buttress body (102, 112) before and during actuation of end effector (40); then allow buttress body (102, 112) to separate from end effector (40) after end effector (40) has been actuated, without causing damage to buttress body (102, 112) that is substantial enough to compromise the proper subsequent functioning of buttress body (102, 112).

Figure 5A:
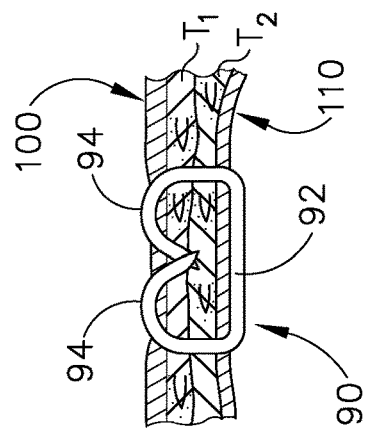
FIG. 5A depicts a cross-sectional end view of a portion of the end effector of FIG. 2 with a buttress assembly formed by the buttresses of FIG. 4 applied to the end effector, with tissue positioned between the buttresses in the end effector, and with the anvil in an open position.
Figure 5B:
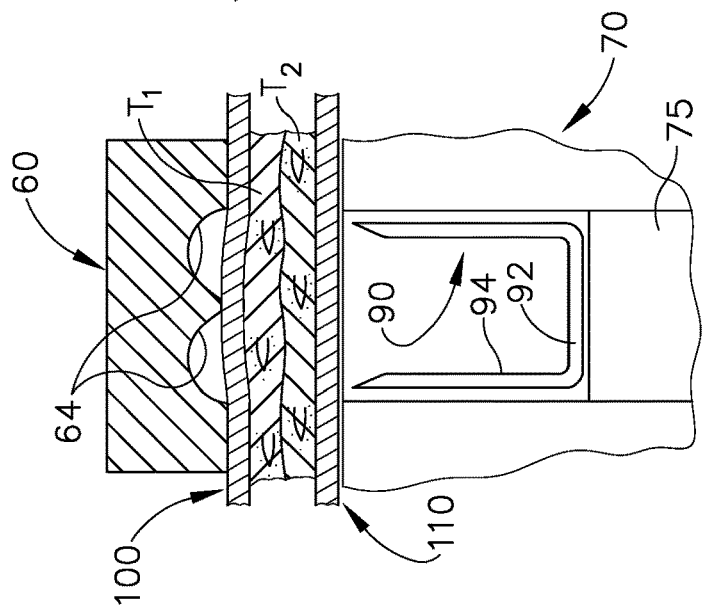
FIG. 5B depicts a cross-sectional end view of the combined end effector and buttress assembly of FIG. 5A, with tissue positioned between the buttresses in the end effector, and with the anvil in a closed position.
Figure 5C:
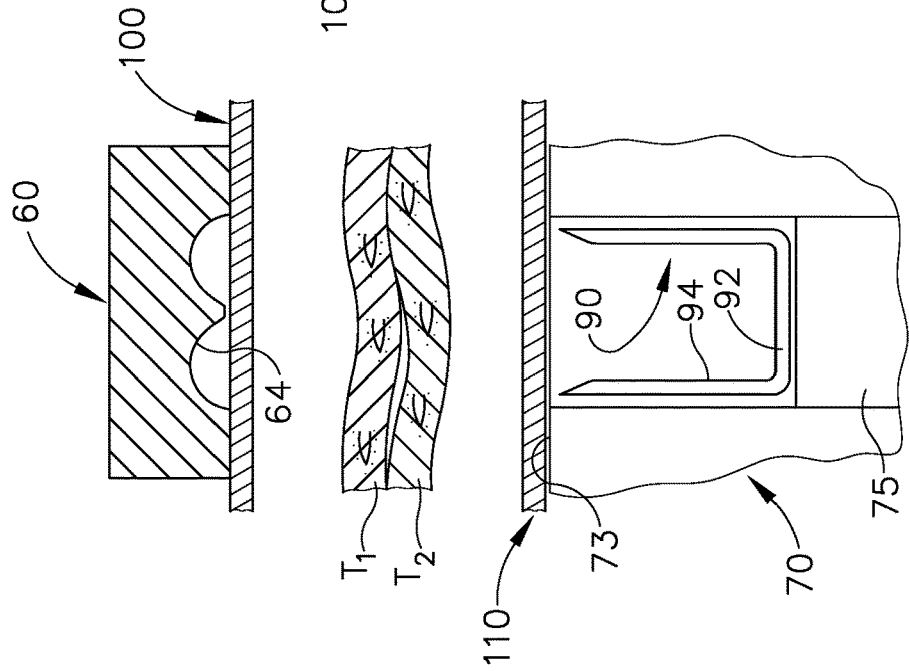
FIG. 5C depicts a cross-sectional view of a staple and the buttress assembly of FIG. 5A having been secured to the tissue by the end effector of FIG. 2.

FIGS. 5A-5C show a sequence where an end effector (40) that has been loaded with buttress assemblies (100, 110) is actuated to drive staples (90) through two apposed layers of tissue ($T_1$, $T_2$), with buttress assemblies (100, 110) being secured to the same layers of tissue ($T_1$, $T_2$) by staples (90). In particular, FIG. 5A shows layers of tissue ($T_1$, $T_2$) positioned between anvil (60) and staple cartridge (70), with anvil (60) in the open position. Buttress assembly (100) is adhered to the underside (65) of anvil (60) via adhesive layer (104); while buttress assembly (110) is adhered to deck (73) of staple cartridge (70) via adhesive layer (114). Layers of tissue ($T_1$, $T_2$) are thus interposed between buttress assemblies (100, 110). Next, trigger (24) is pivoted toward pistol grip (22) to drive closure tube (32) and closure ring (36) distally. This drives anvil (60) to the closed position as shown in FIG. 5B. At this stage, layers of tissue ($T_1$, $T_2$) are compressed between anvil (60) and staple cartridge (70), with buttress assemblies (100, 110) engaging opposite surfaces of tissue layers ($T_1$, $T_2$). End effector (40) is then actuated as described above, driving staple (90) through buttress assemblies (100, 110) and tissue (90). As shown in FIG. 5C, crown (92) of driven staple (90) captures and retains buttress assembly (110) against layer of tissue ($T_2$). Deformed legs (94) of staple (90) capture and retain buttress assembly (100) against layer of tissue ($T_1$).

Figure 6:
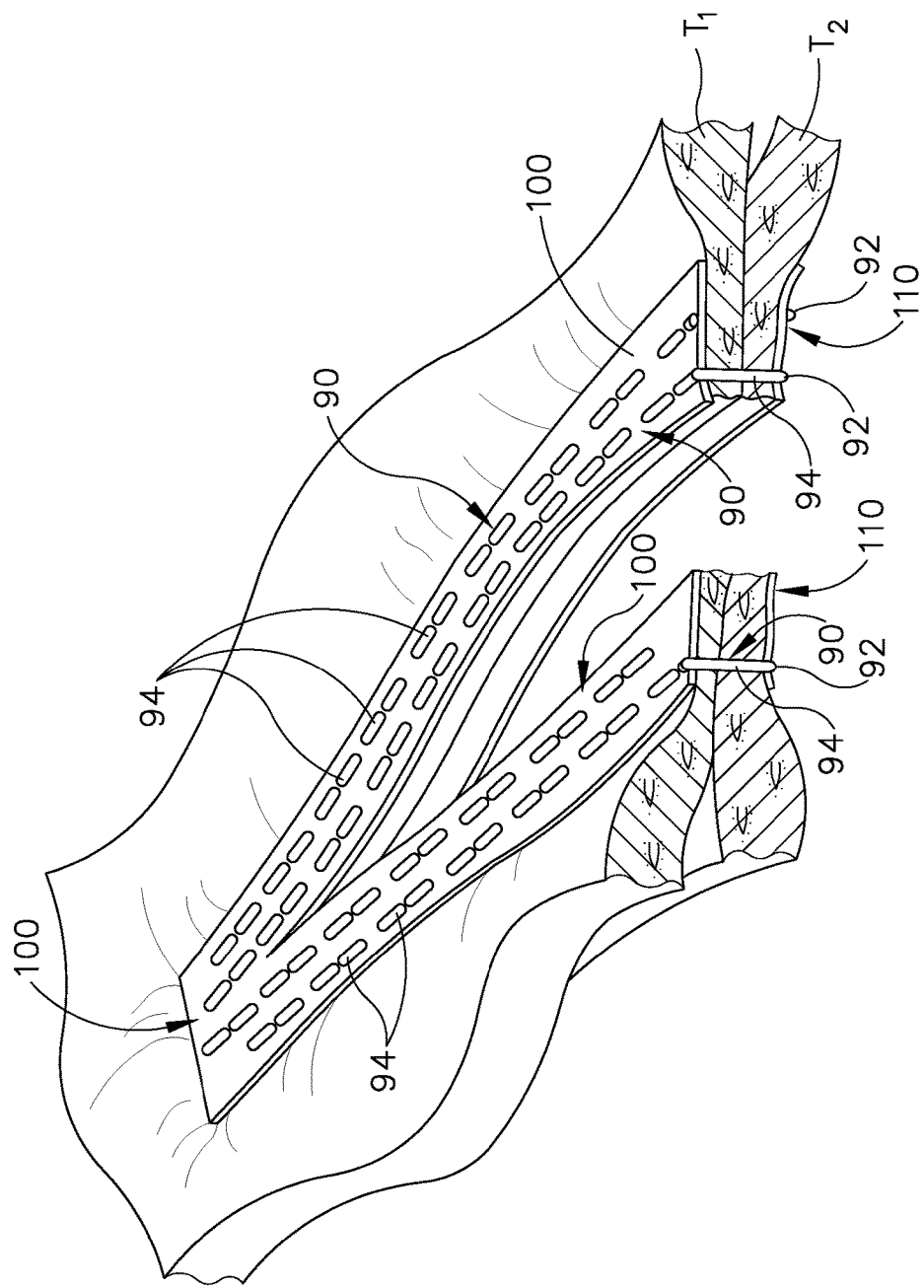
FIG. 6 depicts a perspective view of staples and the buttress assembly of FIG. 5A having been secured to the tissue by the end effector of FIG. 2.

It should be understood that a series of staples (90) will similarly capture and retain buttress assemblies (100, 110) against layers of tissue ($T_1$, $T_2$), thereby securing buttress assemblies (100, 110) to tissue ($T_1$, $T_2$) as shown in FIG. 6. As end effector (40) is pulled away from tissue (90) after deploying staples (90) and buttress assemblies (100, 110), buttress assemblies (100, 110) disengage end effector), such that buttress assemblies (100, 110) remain secured to tissue ($T_1$, $T_2$) with staples (90). Buttress tissue ($T_1$, $T_2$) thus provide structural reinforcement to the lines of staples (90). As can also be seen in FIG. 6, knife member (80) also cuts through a centerline of buttress tissue assemblies (100, 110), separating each buttress assemblies (100, 110) into a corresponding pair of sections, such that each section remains secured to a respective severed region of tissue ($T_1$, $T_2$).

In the foregoing example, buttress assembly (100) is sized to span across the full width of underside (65), such that buttress assembly (100) spans across channel (62). Thus, knife member (80) cuts through buttress assembly (100) during actuation of end effector (40) as described above. In some other examples, such as those described below, buttress assembly (100) is provided in two separate, laterally spaced apart portions, with one portion being disposed on underside (65) on one side of channel (62) and another portion being disposed on underside (65) on the other side of channel (62). In such versions, buttress assembly (100) does not span across channel (62), such that knife member (80) does not cut through buttress assembly (100) during actuation of end effector (40).

Likewise, buttress assembly (110) may be sized to span across the full width of deck (73), such that buttress assembly (110) spans across channel (72), and such that knife member (80) cuts through buttress assembly (110) during actuation of end effector (40) as described above. Alternatively, buttress assembly (110) may be provided in two separate, laterally spaced apart portions, with one portion being disposed on deck (73) on one side of channel (72) and another portion being disposed on deck (73) on the other side of channel (72), such that buttress assembly (110) does not span across channel (72), and such that knife member (80) does not cut through buttress assembly (110) during actuation of end effector (40).

In addition to the foregoing, it should also be understood that any of the various buttress assemblies described herein may be further constructed and operable in accordance with at least some of the teachings of U.S. patent application Ser. No. 14/667,842, entitled "Method of Applying a Buttress to a Surgical Stapler," filed Mar. 25, 2015, published as U.S. Pub. No. 2016/0278774 on Sep. 29, 2016, the disclosure of which is incorporated by reference herein.

III. Exemplary Buttress Applier Cartridge

As noted above, buttress assembly (100) may be applied to the underside (65) of anvil (60), and buttress (110) may be applied to deck (73) of staple cartridge (70), before tissue ($T_1$, $T_2$) is positioned in end effector (40), and before end effector (40) is actuated. Because end effector (40) may be actuated many times during use of instrument (10) in a single surgical procedure, it may be desirable to enable an operator to repeatedly and easily load buttress assemblies (100) on underside (65) of anvil (60) during that single surgical procedure. In other words, because end effector (40) may be actuated many times during use of instrument (10) in a single surgical procedure, it may be insufficient to simply provide anvil (60) pre-loaded with a buttress assembly (100) without facilitating the re-loading of anvil (60) with additional buttress assemblies (100) after end effector (40) has been actuated.

Similarly, those of ordinary skill in the art will recognize that staple cartridge (70) will need to be replaced each time end effector (40) is actuated. When end effector (40) is actuated several times during use of instrument (10) in a single surgical procedure, several staple cartridges (70) may thus be used during that surgical procedure. It may seem that each of these staple cartridges (70) may be provided with buttress assembly (110) pre-loaded on deck (73). However, there are some reasons why it may be undesirable to provide a staple cartridge (70) with buttress assembly (110) pre-loaded on deck (73). In other words, it may be desirable to provide loading of buttress assembly (110) on deck (73) immediately prior to usage of staple cartridge in the surgical procedure, rather than loading buttress assembly (110) on deck (73) a substantial time prior to the surgical procedure. For instance, buttress assembly (110) may not be compatible with the same sterilization techniques as staple cartridge (70), such that it may present processing difficulties to package staple cartridge (70) with buttress assembly (110) pre-loaded on deck (73). In addition, the material forming buttress assembly (110) may have certain environmental sensitivities that staple cartridge (70) does not have, such that it may be beneficial to enable buttress assembly (110) and staple cartridge (70) to be stored separately before use. Moreover, buttress assembly (110) may not be warranted or otherwise desired in some surgical procedures, such that it may be desirable to enable a physician to easily choose whether staple cartridge (70) should be loaded with buttress assembly (110) before that staple cartridge (70) is used in the surgical procedure.

In view of the foregoing, it may be desirable to enable an operator to repeatedly and easily load buttress assemblies (100, 110) on end effector (40) on an ad hoc basis during a given surgical procedure. It may also be desirable to provide a device that provides support and protection to buttress assemblies (100, 110) before buttress assemblies (100, 110) are loaded on end effector (40), in addition to that same device also enabling buttress assemblies (100, 110) to be easily loaded on end effector. The examples described below relate to various cartridge assemblies that provide such support, protection, and loading of buttress assemblies (100, 110). It should be understood that the following examples are merely illustrative. Numerous variations will be apparent to those of ordinary skill in the art in view of the teachings herein.

Figure 7:
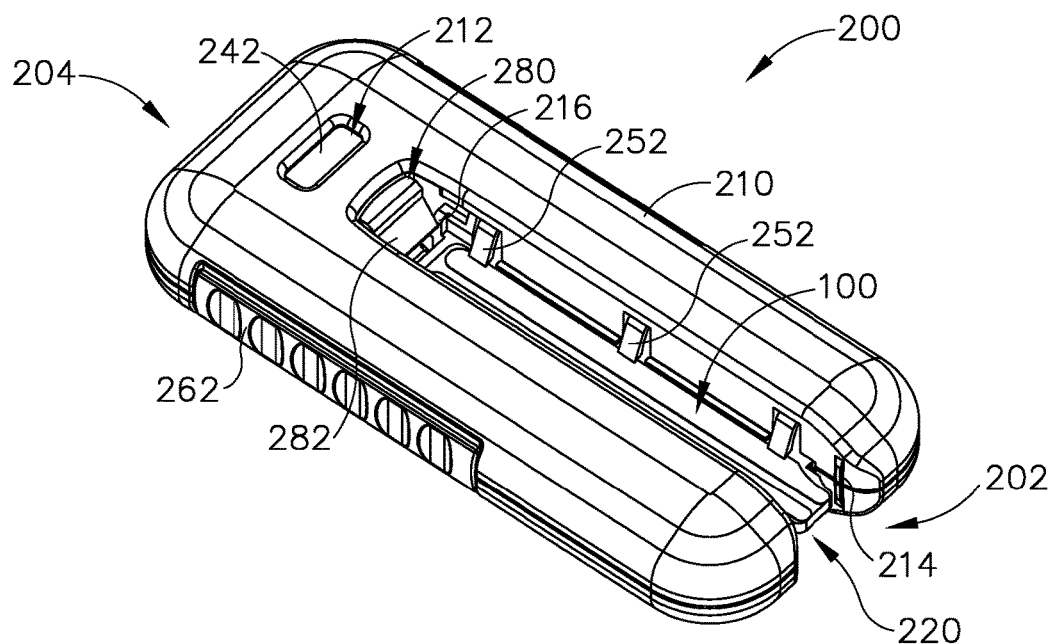
FIG. 7 depicts a perspective view of an exemplary buttress applier cartridge that may be used to carry and apply the buttress assembly of FIG. 5A.
Figure 8:
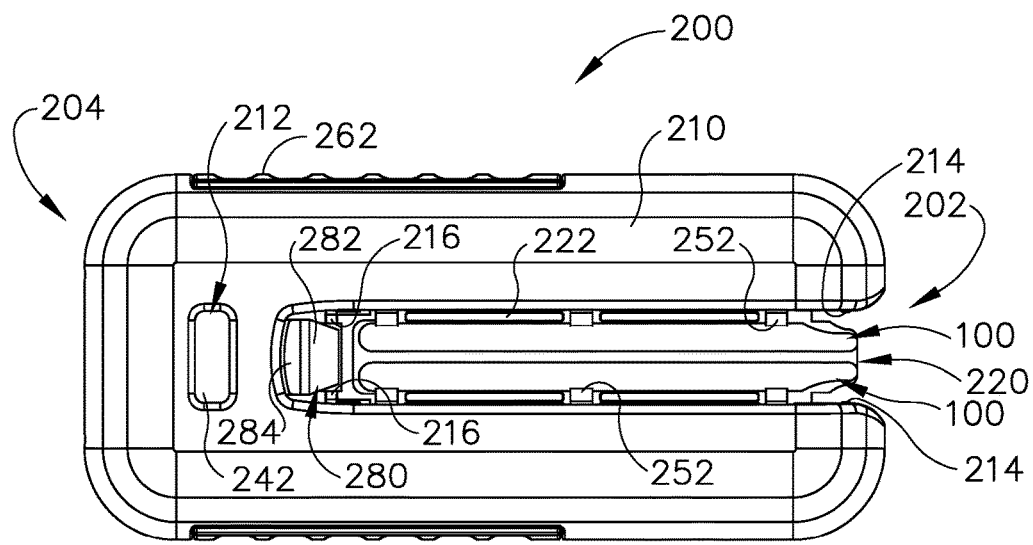
FIG. 8 depicts a top plan view of the buttress applier cartridge of FIG. 7.
Figure 9:
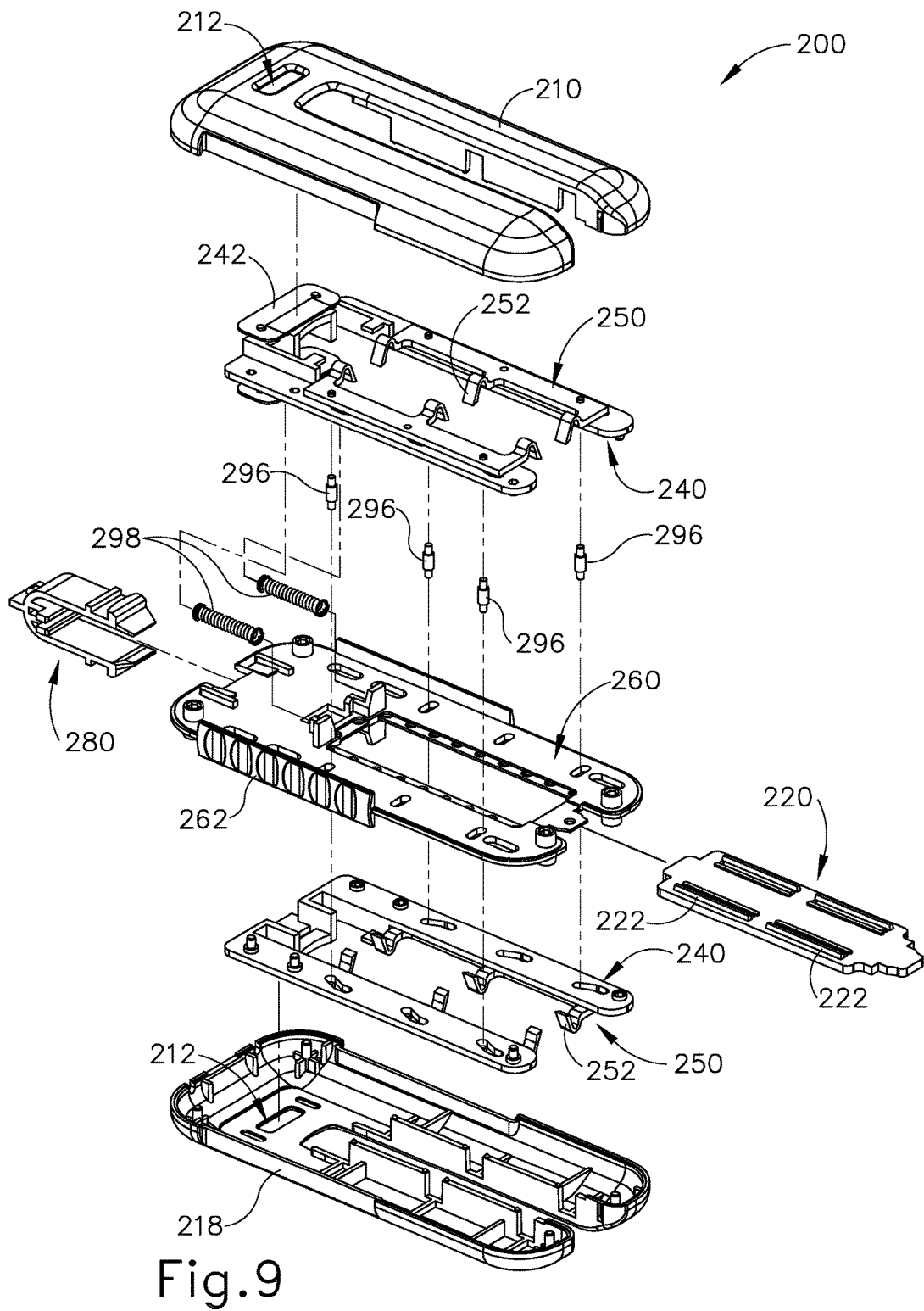
FIG. 9 depicts an exploded perspective view of the buttress applier cartridge of FIG. 7.

FIGS. 7-17B show an exemplary buttress applier cartridge (200) that may be used to support and protect buttress assemblies (100, 110). Cartridge (200) may also be used to easily load buttress assemblies (100, 110) on end effector (40). As best seen in FIGS. 7-8, cartridge (200) of this example comprises an open end (202) and a closed end (204). Open end (202) is configured to receive end effector (40) as will be described in greater detail below. Cartridge (200) further includes a first housing (210) and a second housing (218), which each generally define a "U" shape to present open end (202). As best seen in FIG. 9, various components are interposed between housings (210, 218). In particular, these components include a platform (220), a pair of actuator sleds (240), a pair of retainers (250), a chassis (260), and a sled retainer (280). Each of these components will be described in greater detail below.

Platform (220) of the present example is configured to support a pair of buttress assemblies (100) on one side of platform (220) and another pair of buttress assemblies (110) on the other side of platform (220). Platform (220) is exposed in recesses that are formed between the prongs of the "U" configuration of housings (210, 218). The location of platform (220) and buttress assemblies (100, 110) in such recesses may prevent inadvertent contact between buttress assemblies (100, 110) and other devices in the operating room. In other words, housings (210, 218) may provide some degree of physical shielding of buttress assemblies (100, 110).

In the present example, each buttress assembly (100, 110) is provided in a respective pair of portions that are separated to avoid spanning across channels (62, 72) of anvil (60) and staple cartridge (70), respectively, though it should be understood that platform (220) may just as easily support wide versions of buttress assemblies (100, 110) that unitarily span across channels (62, 72) of anvil (60) and staple cartridge (70), respectively. The outer edges of platform (220) are captured between housings (210, 218) and include retention features (222) in the form of ridges that further engage housings (210, 218) to prevent platform (220) from sliding relative to housings (210, 218). In some versions, platform (220) is formed of a material that provides a high coefficient of friction, thereby reducing any tendency that buttress assemblies (100, 110) might otherwise have to slide along corresponding surfaces of platform (220). For instance, platform (220) may comprise an elastomeric material and/or a foam material. In some instances, platform (220) is formed of a compressible foam material that is configured to maintain a compressed configuration after being compressed by end effector (40). By way of example only, platform (220) may comprise Santoprene, closed-cell polyurethane foam, any other compressible material, and/or a material that may be made compressible via geometry (e.g., a rubber material with deformable standing features). Various suitable materials and structural configurations that may be used to form platform (220) will be apparent to those of ordinary skill in the art in view of the teachings herein.

Figure 11:
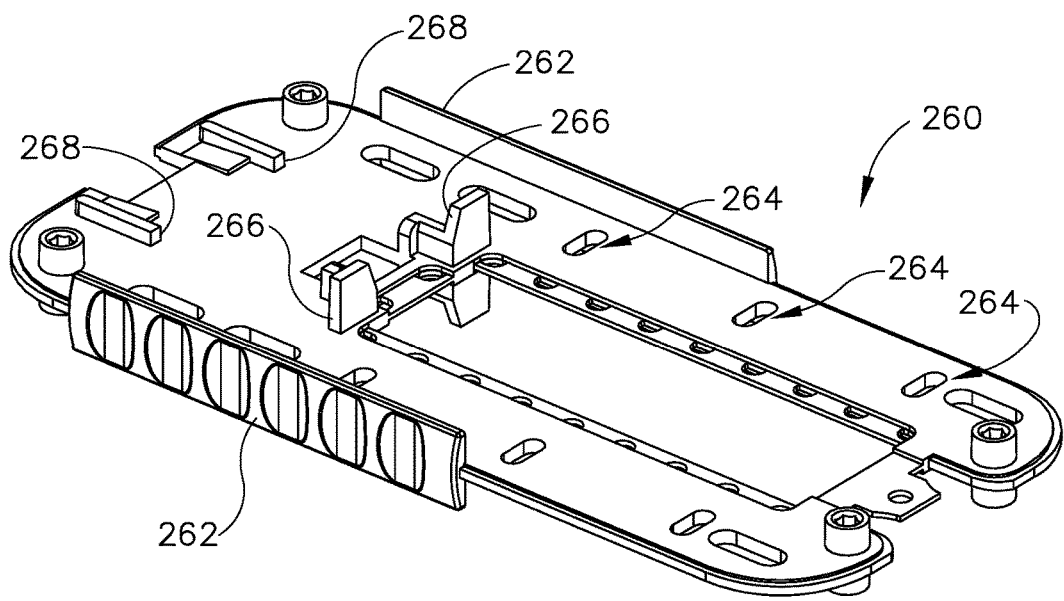
FIG. 11 depicts a perspective view of a chassis of the buttress applier cartridge of FIG. 7.
Figure 15A:
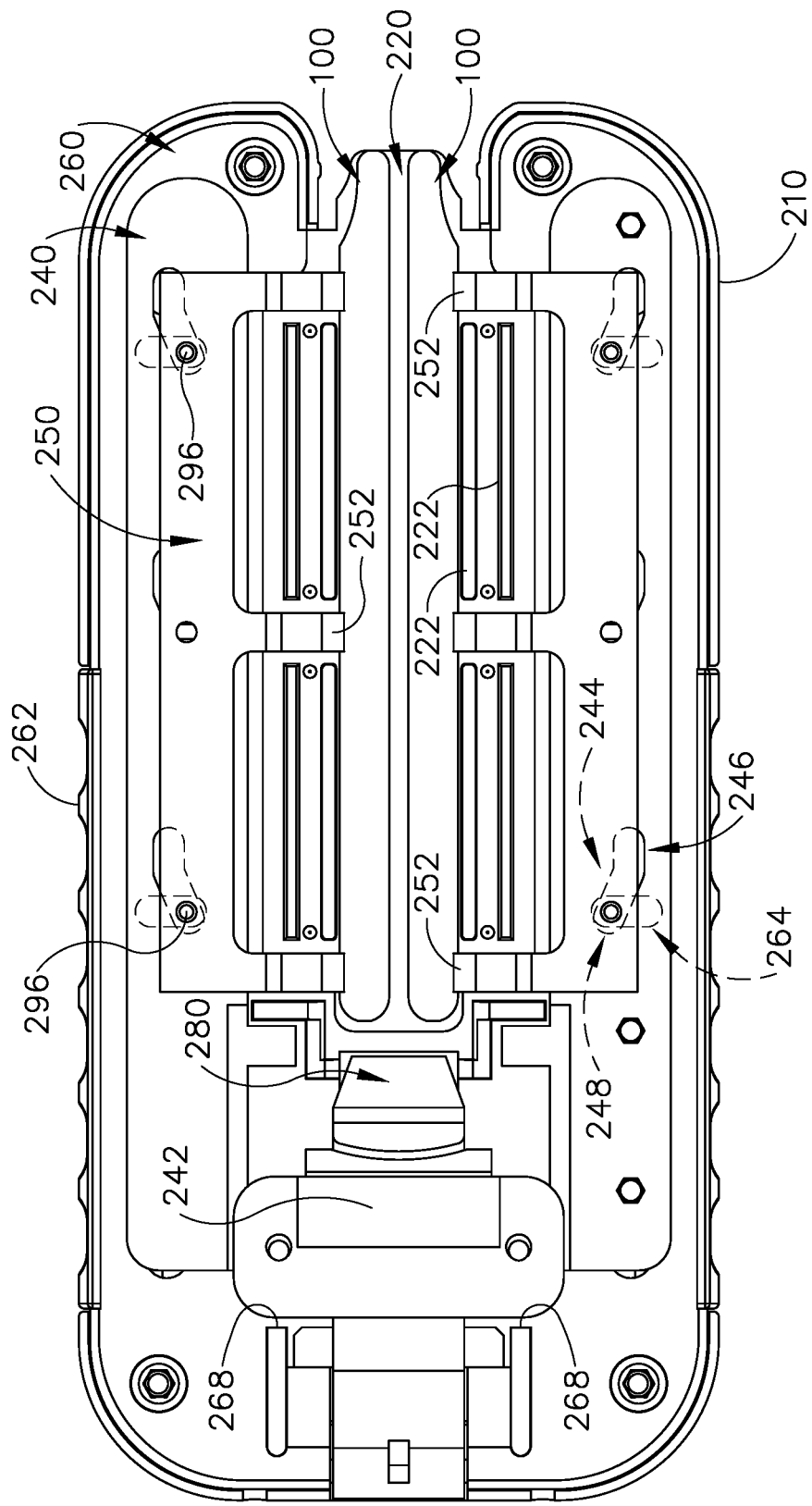
FIG. 15A depicts a top plan view of the buttress applier cartridge of FIG. 7, with a housing member removed, with a buttress assembly loaded on a platform of the buttress applier cartridge, and with retainers positioned to secure the buttress assembly to the platform.
Figure 15B:
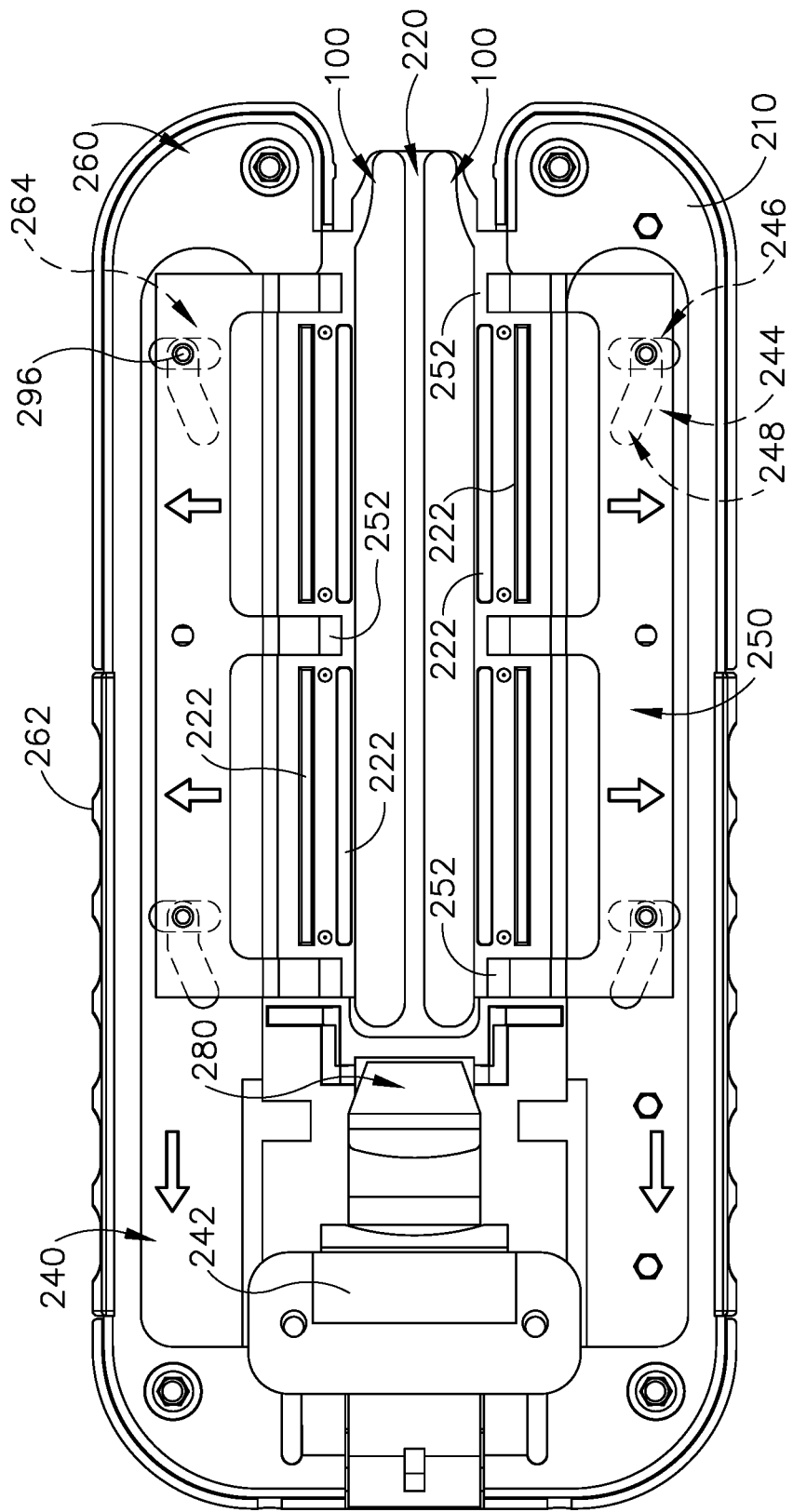
FIG. 15B depicts a top plan view of the buttress applier cartridge of FIG. 7, with a housing member removed, with a buttress assembly loaded on a platform of the buttress applier cartridge, and with retainers positioned to release the buttress assembly to the platform.

Chassis (260) is configured to cooperate with housings (210, 218) to provide a mechanical ground for moving components of cartridge (200) and provide structural support for components of cartridge (200). As shown in FIGS. 7-8, chassis (260) includes integral gripping features (262) that are exposed on opposite sides of housings (210, 218). Gripping features (262) have a surface geometry that is configured to promote an operator's grip of cartridge (200) during use of cartridge (200). Various suitable configurations that may be used for gripping features (262) will be apparent to those of ordinary skill in the art in view of the teachings herein. Similarly, various surface treatments (e.g., elastomeric material, etc.) that may be applied to gripping features (262) will be apparent to those of ordinary skill in the art in view of the teachings herein. As best seen in FIG. 11, chassis (260) further includes a set of laterally oriented slots (264), a first pair of bosses (266), and a second pair of bosses (268). Slots (264) are configured to slidably receive pins (296) as shown in FIGS. 9 and 15A-15B. In particular, pins (296) may translate laterally within slots (264) (i.e. toward and away from the central longitudinal axis extending along the center of platform (220)). In the present example, there are six slots (264) and only four pins (296), such that two of the slots (264) are not used. In other versions, there are six pins (296) such that all six slots (264) are used. In still other versions, there are only four slots (264), corresponding with the four pins (296) of the present example.

Figure 12:
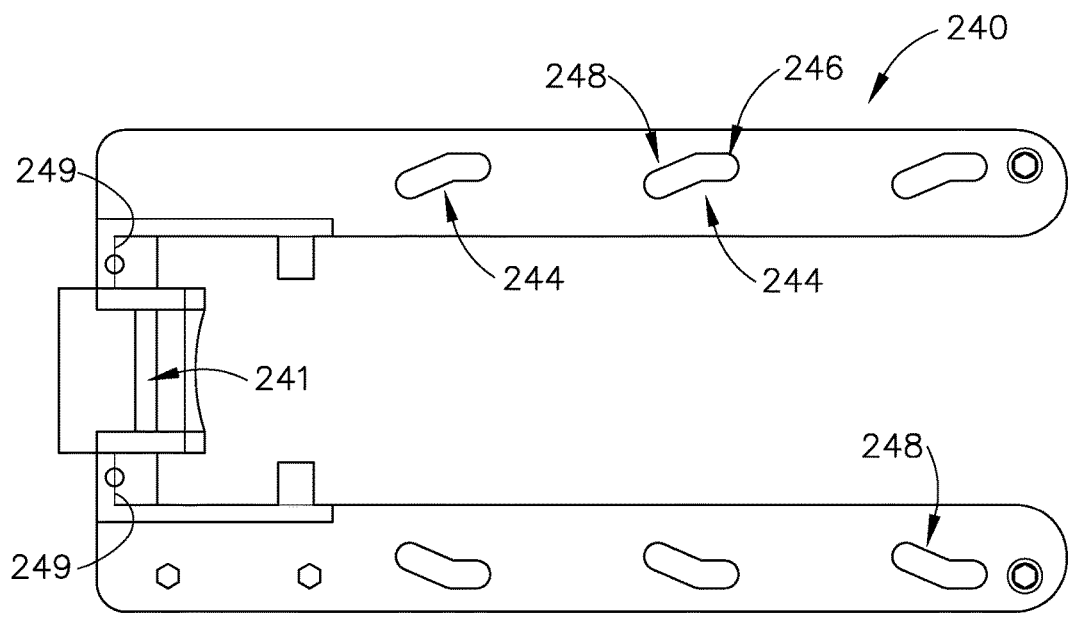
FIG. 12 depicts a top plan view of an actuator sled of the buttress applier cartridge of FIG. 7.

Actuator sleds (240) are slidably positioned on opposite faces of chassis (260). As shown in FIG. 12, each actuator sled includes a locking recess (241), a set of slots (244), and a pair of boss features (249). As shown in FIG. 9, a set of coil springs (298) are positioned between bosses (266) of chassis (260) and boss features (249) of actuator sled (240). Coil springs (298) resiliently bias actuator sleds (240) proximally relative to chassis (260). As will be described in greater detail below, locking recess (241) is configured to selectively engage a locking ridge (286) of sled retainer (280) to selectively lock the longitudinal position of actuator sleds (240) relative to chassis (260), thereby resisting the resilient bias of coil springs (298). As shown in FIGS. 9 and 15A-15B, an indicator plate (242) is secured to the proximal end of each actuator sled (240), such that indicator plates (242) will translate unitarily with actuator sleds (240). Indicator plates (242) are positioned to correspond with windows (212) that are formed in housings (210, 218), such that indicator plates (242) are visible through windows (212) when actuator sleds (240) are in a distal position and when actuator sleds (240) are in a proximal position. As will be described in greater detail below, indicator plates (242) may include different colored regions or other markings that provide visual indication through windows (212), visually indicating whether actuator sleds (240) are in the distal position or the proximal position.

As shown in FIGS. 9 and 15A-15B, slots (244) are positioned to also receive pins (296). Each slot (244) includes a longitudinally extending portion (246) and an obliquely extending portion (248). Pins (296) are configured to travel along the longitudinally extending portion (246) of each corresponding slot (244) and along the obliquely extending portion (248) of each corresponding slot (244). In the present example, there are six slots (244) and only four pins (296), such that two of the slots (244) are not used. In other versions, there are six pins (296) such that all six slots (244) are used. In still other versions, there are only four slots (244), corresponding with the four pins (296) of the present example.

Figure 13:
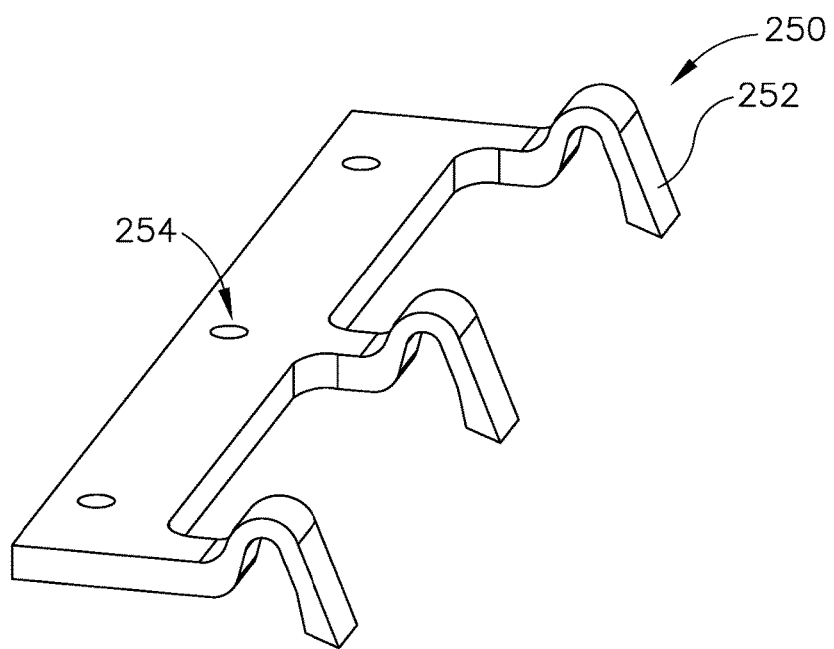
FIG. 13 depicts a perspective view of a retainer of the buttress applier cartridge of FIG. 7.

Retainers (250) are slidably disposed on respective actuator sleds (240), such that each actuator sled (240) is slidably interposed between chassis (260) and a corresponding retainer (250). As shown in FIG. 13, each retainer (250) includes a set of arms (252) and a set of openings (254). Openings (254) are positioned to receive pins (296). Pins (296) are secured within openings (254) such that pins (296) do not move within corresponding openings (254). Retainers (250) thus travel unitarily with pins (296) in this example, as will be described in greater detail below. In the present example, there are six openings (254) and only four pins (296), such that two of the openings (254) are not used. In other versions, there are six pins (296) such that all six openings (254) are used. In still other versions, there are only four openings (254), corresponding with the four pins (296) of the present example.

Arms (252) of the present example are configured to selectively secure buttress assemblies (100, 110) to platform (220). In particular, FIGS. 7-8, 14A, and 15A show retainers (250) positioned such that buttress assemblies (100, 110) are interposed between the free ends of arms (252) and platform (220). As described in greater detail below, retainers (250) are movable laterally outwardly such that arms (252) disengage buttress assemblies (100, 110), thereby enabling buttress assemblies (100, 110) to be removed from platform (220). In the present example, arms (252) are resilient and are thus configured to resiliently bear against buttress assemblies (100, 110), thereby pinching buttress assemblies (100, 110) against platform (220). Other suitable ways in which arms (252) may engage buttress assemblies (100, 110) will be apparent to those of ordinary skill in the art in view of the teachings herein.

Figure 10:
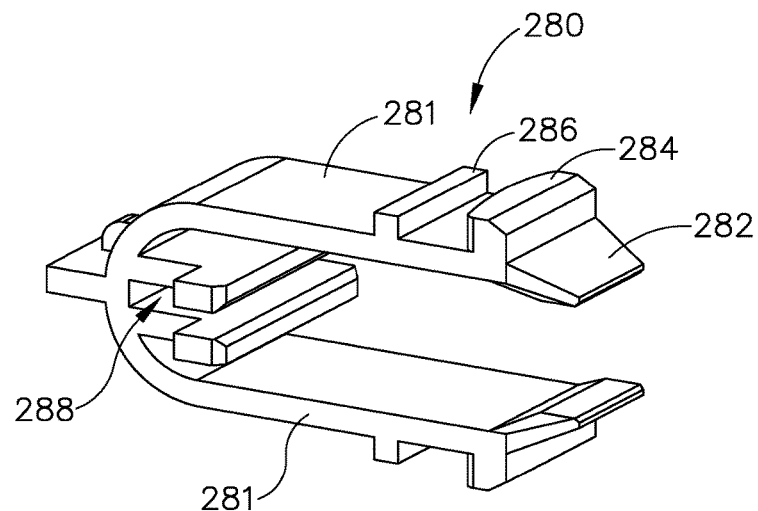
FIG. 10 depicts a perspective view of a sled retainer of the buttress applier cartridge of FIG. 7.
Figure 14A:
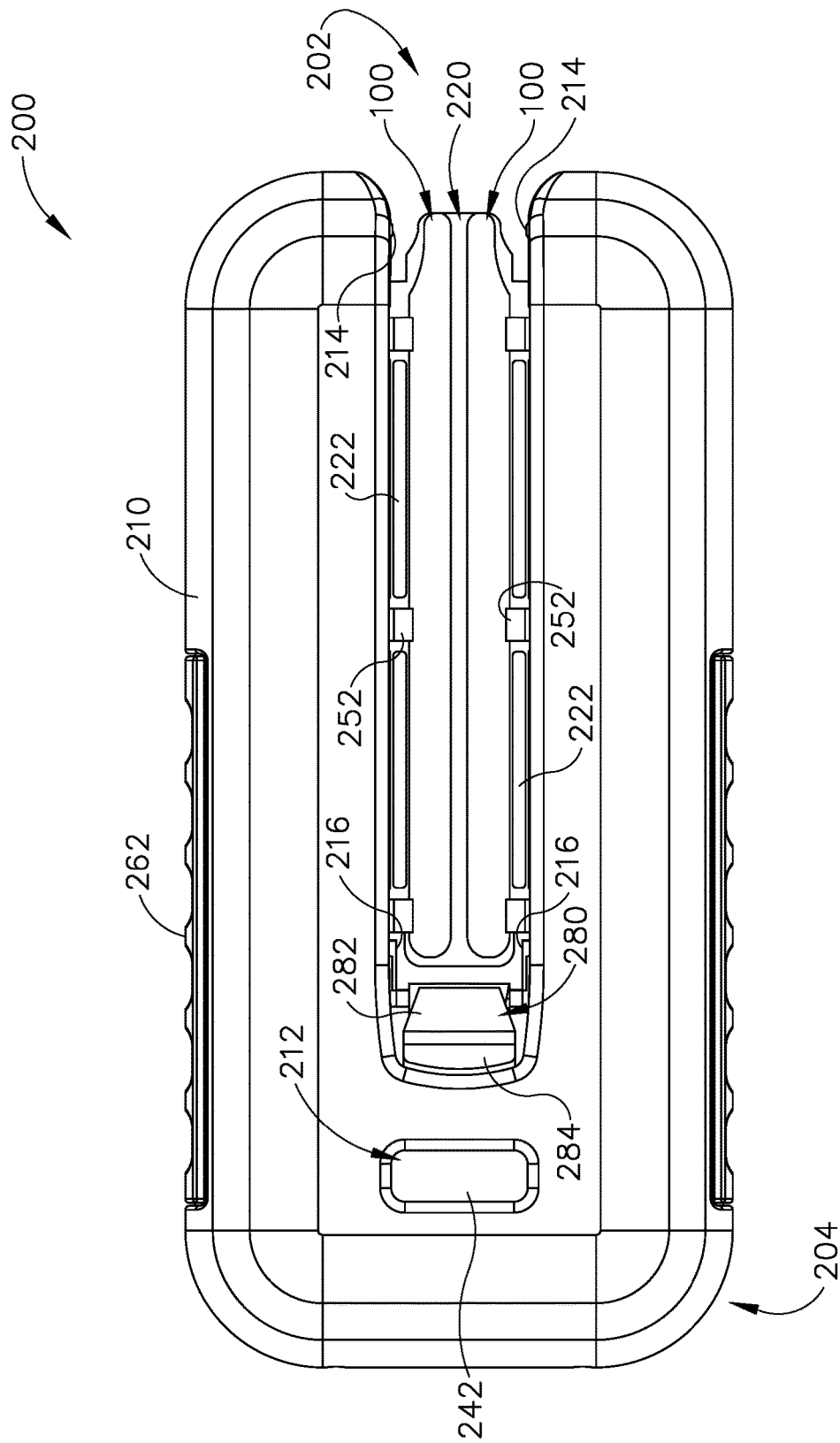
FIG. 14A depicts a top plan view of the buttress applier cartridge of FIG. 7, with a buttress assembly loaded on a platform of the buttress applier cartridge, and with retainers positioned to secure the buttress assembly to the platform.
Figure 14B:
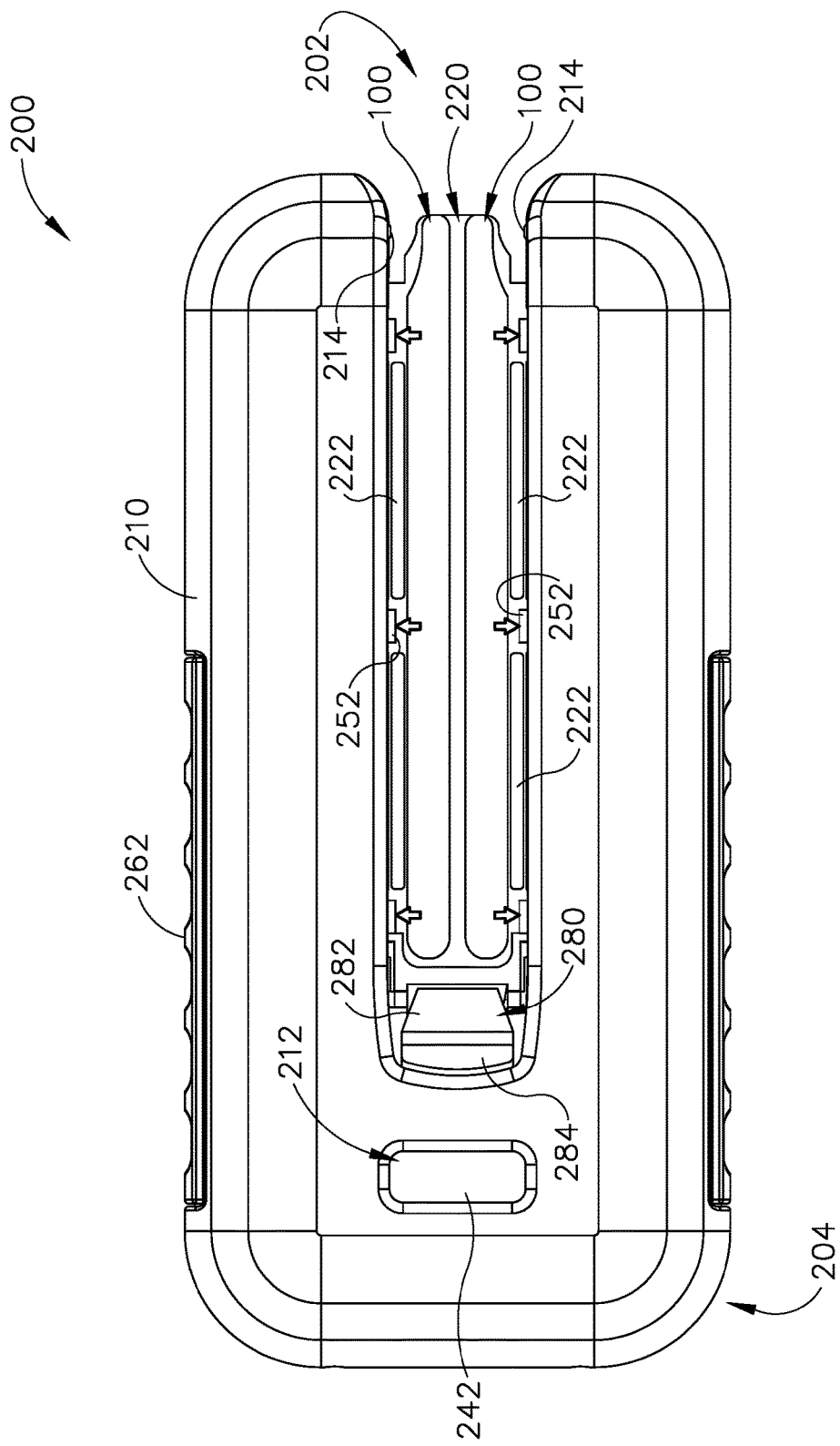
FIG. 14B depicts a top plan view of the buttress applier cartridge of FIG. 7, with a buttress assembly loaded on a platform of the buttress applier cartridge, and with retainers positioned to release the buttress assembly to the platform.

As shown in FIG. 10, sled retainer (280) includes a pair of arms (281) that together generally define a "U" shape. The free end of each arm (281) includes a tapered cam surface (282) and a housing engagement feature (284). As best seen in FIGS. 8 and 14A-14B, housing engagement features (284) are positioned to engage corresponding surfaces of housings (210, 218). Each arm (281) further includes a respective locking ridge (286) spaced proximally from the corresponding housing engagement feature (284). Sled retainer (280) further defines a channel (288) in the region where arms (281) meet each other. As shown in FIG. 9, channel (288) is configured to receive the proximal end of chassis (260).

Figure 16A:
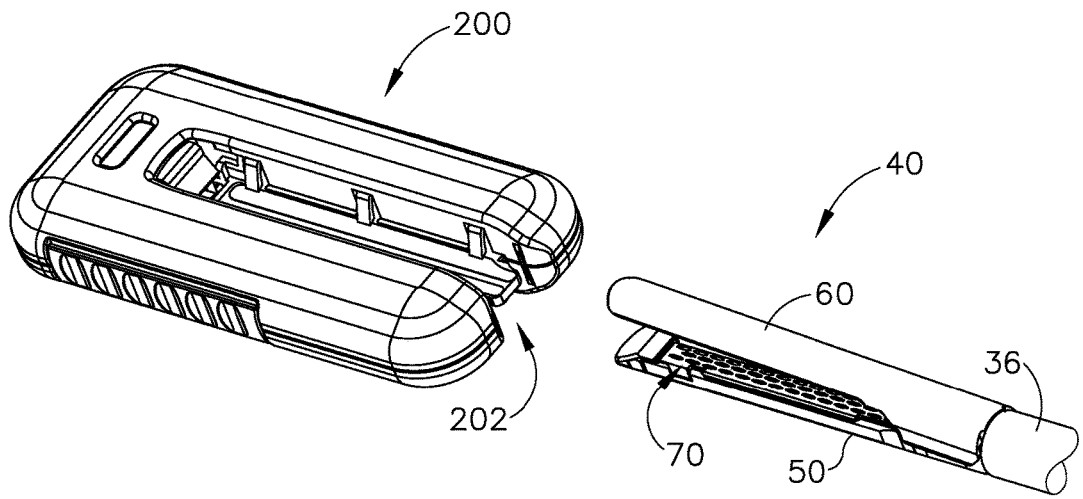
FIG. 16A depicts a perspective view of the end effector of FIG. 2 and the buttress applier cartridge of FIG. 7, with the end effector approaching the buttress applier cartridge.
Figure 16B:
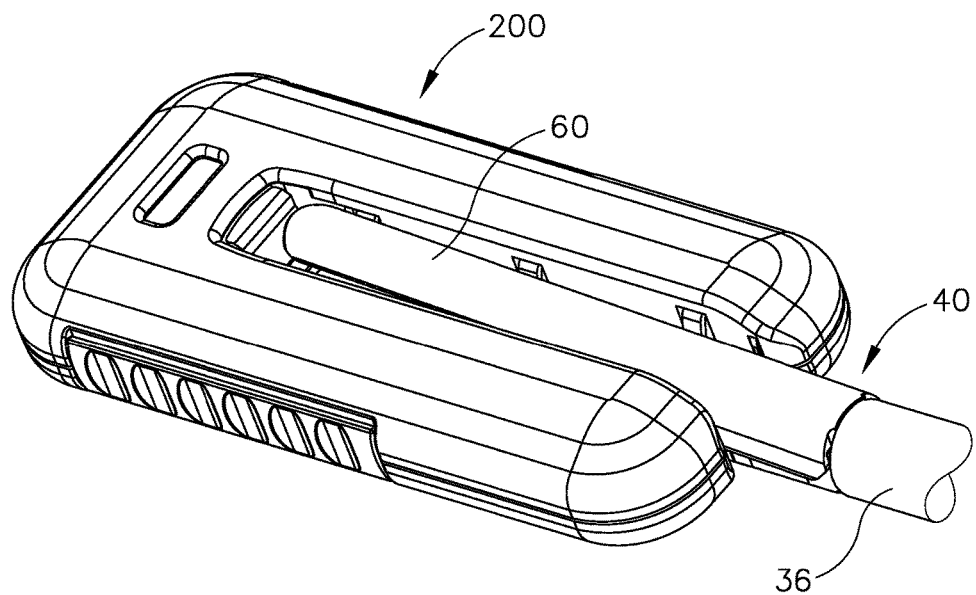
FIG. 16B depicts a perspective view of the end effector of FIG. 2 and the buttress applier cartridge of FIG. 7, with the buttress applier cartridge positioned in the end effector.
Figure 17A:
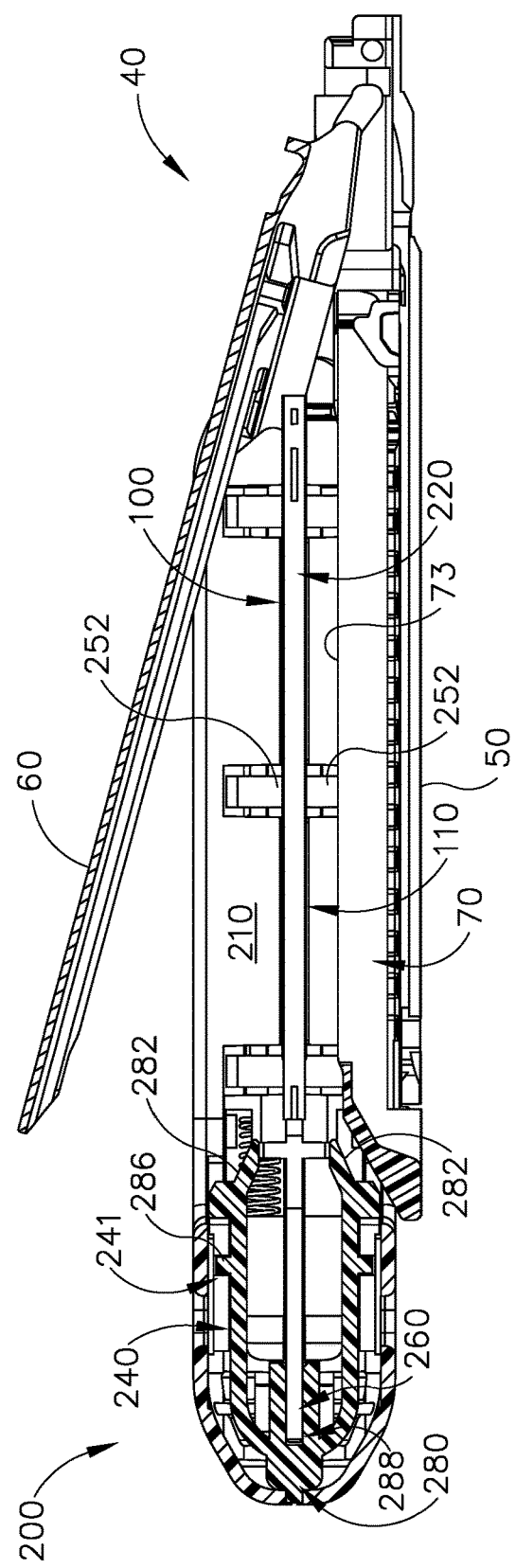
FIG. 17A depicts a cross-sectional side view of the end effector of FIG. 2 and the buttress applier cartridge of FIG. 7, with the buttress applier cartridge positioned in the end effector, and with the end effector in an open configuration.
Figure 17B:
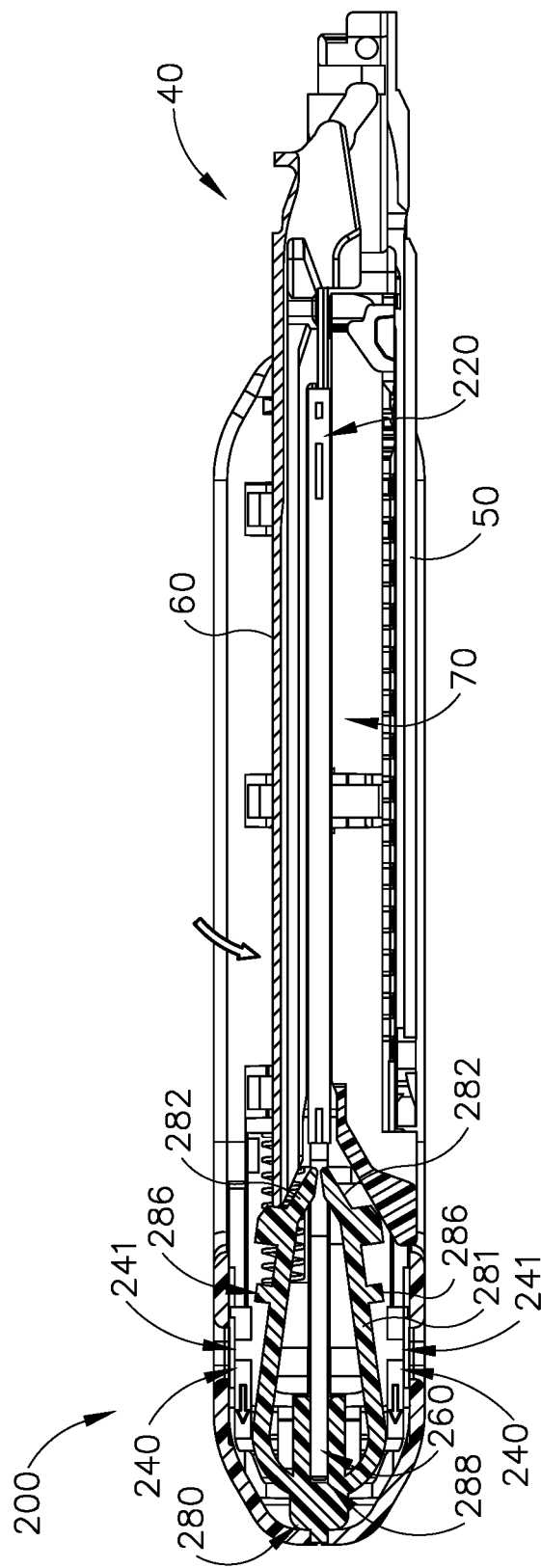
FIG. 17B depicts a cross-sectional side view of the end effector of FIG. 2 and the buttress applier cartridge of FIG. 7, with the buttress applier cartridge positioned in the end effector, and with the end effector in a closed configuration.

FIGS. 14A-17B show cartridge (200) in different stages of operation. In particular, FIGS. 14A, 15A, and 17A show cartridge (200) in a configuration where retainer arms (252) are positioned to hold buttress assemblies (100, 110) against platform (220); while FIGS. 14B, 15B, and 17B show cartridge (200) in a configuration where retainer arms (252) are positioned to release buttress assemblies (100, 110) from platform (220). While FIGS. 14A-17B only show buttress assembly (100) on platform (220), it should be understood that buttress assembly (110) would be retained on and released from platform (220) in an identical fashion.

To use cartridge (200) to load end effector (40), the operator would first position cartridge (200) and end effector (40) such that end effector is aligned with open end (202) of cartridge (200) as shown in FIG. 16A. The operator would then advance end effector (40) distally (and/or retract cartridge (200) proximally) to position platform (220) and buttress assemblies (100, 110) between anvil (60) and staple cartridge (70) as shown in FIG. 16B. This will ultimately result in the arrangement shown in FIG. 17A. While end effector (40) is not shown in FIG. 14A or 15A, it should be understood that cartridge (200) is in the same state in FIG. 17A as the state shown in FIGS. 14A and 15A. In this state, actuator sleds (240) are in a first longitudinal position (i.e., closer to open end (202)). Coil springs (298) are resiliently urging actuator sleds (240) toward a second longitudinal position (i.e., closer to closed end (204)). However, as best seen in FIG. 17A, locking ridges (286) of sled retainer (280) are disposed in locking recesses (241) of actuator sleds (240), thereby holding actuator sleds (240) in the first longitudinal position. With actuator sleds (240) in the first longitudinal position, retainers (250) are located at inward positions to retain buttress assemblies (100, 110) against platform (220). As shown in FIG. 15A, at this stage, pins (296) are positioned at the inner ends of slots (264) of chassis (260); and in the ends of obliquely extending portions (248) of slots (244).

In order to load buttress assemblies (100, 110) on end effector (40), the operator may simply close end effector (40) by pivoting anvil (60) toward staple cartridge (70), as described above, to reach the state shown in FIG. 17B. As shown, closure of end effector (40) results in the distal ends of anvil (60) and staple cartridge (70) bearing against cam surfaces (282) of sled retainer (280). This causes arms (281) of sled retainer (280) to deform toward each other, such that locking ridges (286) disengage locking recesses (241) of actuator sleds (240). With locking ridges (286) disengaged from locking recesses (241) of actuator sleds (240), coil springs (298) drive actuator sleds (240) proximally to the second longitudinal position. Actuator sleds (240) engage bosses (268) of chassis (260) when actuator sleds (240) reach the proximal position, such that bosses (268) provide a hard stop.

It should be understood that, when actuator sleds (240) are driven proximally by coil springs (298) in response to release of actuator sleds (240) by sled retainer (280), the sudden, striking engagement between actuator sleds (240) and bosses (268) may produce a click or snap sound, providing audible feedback to the operator indicating actuation of cartridge (200). Moreover, the sudden, striking engagement between actuator sleds (240) and bosses (268) may provide tactile feedback to the operator's hand grasping cartridge (200) indicating that the release mechanism has been successfully actuated. As another merely illustrative variation, platform (220) may include various features that provide audible and/or tactile feedback to indicate that end effector (40) has clamped on buttress assemblies (100, 110) and platform (220) with sufficient force, including but not limited to popping bubbles in platform, a snapping dome of spring steel, etc. It should also be understood that some component of cartridge (200) may include a frangible component that fractures in response to end effector (40) clamping on buttress assemblies (100, 110) and platform (220) with sufficient force, such that the fracture of the frangible component provides the operator with audible and/or tactile feedback. As yet another merely illustrative example, cartridge (200) may include a motorized or spring-loaded off center counter weight that spins in response to end effector (40) clamping on buttress assemblies (100, 110) and platform (220) with sufficient force, such that the spinning off center counter weight provides the operator with audible and/or tactile feedback. Other suitable features that may be used to provide the operator with audible and/or tactile feedback to indicate that end effector (40) has clamped on buttress assemblies (100, 110) and platform (220) with sufficient force will be apparent to those of ordinary skill in the art in view of the teachings herein.

In the present example, cartridge (200) is configured such that both arms (281) must be deformed toward each other at the same time in order for actuator sleds (240) to be unlocked and thereby permitted to translate proximally to the second longitudinal position. If only one arm (281) is deformed toward the other arm (281), the locking ridge (286) of the non-deformed arm (281) will remain disposed in the corresponding locking recess (241) of actuator sled (240), thereby continuing to hold actuator sled (240) in the first longitudinal position. By requiring both arms (281) to be deformed toward each other at the same time in order for actuator sleds (240) to be unlocked, the configuration of sled retainer (280) will reduce the risk of cartridge (200) being actuated prematurely or inadvertently.

As best seen in the transition from the view shown in FIG. 15A (actuator sleds (240) in the first longitudinal position) to the view shown in FIG. 15B (actuator sleds (240) in the second longitudinal position), slots (244) act as cams against pins (296) and thereby drive retainers (250) outwardly as actuator sleds (240) travel proximally. In particular, pins (296) traverse obliquely extending portions (248) of slots (244) and then longitudinally extending portions (246) of slots (244). Obliquely extending portions (248) of slots (244) drive pins (296) outwardly during this range of travel. Since retainers (250) travel unitarily with pins (296), retainers (250) travel outwardly as well. Laterally oriented slots (264) of chassis (260) accommodate the outward lateral movement of pins (296) but prevent pins (296) from moving longitudinally during the transition from the state shown in FIG. 15A to the state shown in FIG. 15B.

Upon reaching the state shown in FIG. 15B, retainers (250) are disengaged from buttress assemblies (100, 110). This state is also shown in FIG. 14B. It should be understood that end effector (40) is still in the closed configuration at this stage, as also shown in FIG. 17B. Thus, with end effector (40) clamping on both buttress assemblies (100, 110), adhesive layers (104, 114) are adhered to underside (65) of anvil (60) and deck (73) of staple cartridge (70). End effector (40) may then be re-opened (i.e., pivoting anvil (60) away from staple cartridge (70)) and pulled away from cartridge (200). With retainers (250) disengaged from buttress assemblies (100, 110), end effector (40) may freely pull buttress assemblies (100, 110) away from platform (220) as end effector (40) is pulled away from cartridge (200). With buttress assemblies (100, 110) loaded on end effector (40), end effector (40) may then be used as described above with reference to FIGS. 5A-6.

Referring back to FIGS. 7-8, housings (210, 218) of the present example include proximal guide features (214) and distal guide features (216). Guide features (214, 216) are configured to assist in providing proper alignment of end effector (40) with cartridge (200). In particular, guide features (214, 216) are configured to engage the lateral sides of lower jaw (50) and anvil (60) to ensure that the central longitudinal axis of end effector (40) is coplanar with the central longitudinal axis of platform (220). Such alignment will prevent buttress assemblies (100, 110) from being applied to underside (65) or deck (73) in a skewed orientation. In some versions, guide features (214, 216) engage the lateral sides of lower jaw (50) and anvil (60) as soon as end effector (40) is positioned as shown in FIG. 16B (i.e., before anvil (60) is pivoted to the closed position). In some other versions, guide features (214, 216) do not engage the lateral sides of lower jaw (50) and anvil (60) until anvil (60) is pivoted closer to the closed position. In the present example, guide features (214, 216) are unitarily formed features of housings (210, 218). In some other versions, guide features (214, 216) are movable relative to housings (210, 218) and are resiliently biased to provide self-centering guidance to the lateral sides of lower jaw (50) and anvil (60). Various suitable forms that guide features (214, 216) may take will be apparent to those of ordinary skill in the art in view of the teachings herein.

As noted above, indicator plates (242) may include different colored regions or other markings (e.g., text, pictograms, etc.) that provide visual indication through windows (212), visually indicating whether actuator sleds (240) are in the first longitudinal position (FIG. 15A) or the second longitudinal position (FIG. 15B). The operator may thus view indicator plate (242) through window (212) to determine whether cartridge (200) has successfully released buttress assemblies (100, 110). An operator may also view indicator plate (242) through window (212) to determine whether cartridge (200) has been previously used. Various suitable markings that may be provided on indicator plates (242) to provide visual feedback indicating the state of cartridge (200) will be apparent to those of ordinary skill in the art in view of the teachings herein.

It should also be understood that platform (220) may be modified to include a high contrast color under buttress assemblies (100, 110). In particular, such regions of high contrast color may be completely obscured by buttress assemblies (100, 110) reside on platform (220); and may be fully revealed when buttress assemblies (100, 110) are removed from on platform (220). The color may be different from the color of buttress assemblies (100, 110); and may provide a high contrast with adjacent regions of platform (220). The high contrast region of platform (220) may thus provide a clear visual indication to the operator that buttress assemblies (100, 110) have been removed from platform (220), making it clear to the operator that cartridge (200) has already been used. The high contrast regions may also include textual (e.g., the word "USED", etc.), pictorial, and/or other indicators to further indicate to the operator that buttress assemblies (100, 110) have been removed from platform (220). As yet another merely illustrative example, platform (220) may be configured to compress and remain compressed when end effector (40) clamps down to pick up buttress assemblies (100, 110), such that the region of platform (220) that was compressed by clamping end effector (40) will remain compressed even after end effector (40) is re-opened and thereby removed from platform (220). The resulting depressed region of platform (220) may thus provide visual indication to the operator that buttress assemblies (100, 110) have been removed from platform (220). Other suitable features that may indicate to an operator that a cartridge (200) has already been used will be apparent to those of ordinary skill in the art in view of the teachings herein.

In some versions, cartridge (200) is modified to include dampening elements that retard the outward movement of retainers (250) when sled retainer (280) releases actuator sleds (240). This may increase the time required for retainers (250) to fully release buttress assemblies (100, 110). This may be desirable in instances where the composition of adhesive layers (104, 114) warrants lengthened application of pressure by anvil (60) and staple cartridge (70) in order to provide reliable adhesion of buttress assemblies (100, 110) to anvil (60) and staple cartridge (70). Various suitable ways in which this may be accomplished will be apparent to those of ordinary skill in the art in view of the teachings herein.

IV. Exemplary End Effector Alignment Features for Buttress Applier Cartridge In some instances, it may be desirable to configure buttress assembly (100) such that the lateral width of buttress assembly (100) closely matches the lateral width of underside (65) of anvil (60). Likewise, it may be desirable to configure buttress assembly (110) such that the lateral width of buttress assembly (110) closely matches the lateral width of deck (73) of anvil (70). Matching these widths may present little to no margin of error with respect to alignment of end effector (40) with buttress assemblies (100, 110). It may therefore be desirable to provide features that ensure or otherwise promote proper alignment of end effector (40) with buttress assemblies (100, 110). Such alignment may include proper lateral positioning of end effector along a lateral plane (i.e., a plane that is parallel to the planes defined by buttress assemblies (100, 110)). Such alignment may also include proper "yaw" positioning about an axis that is perpendicular to the same lateral plane (i.e., a plane that is parallel to the planes defined by buttress assemblies (100, 110)). Several examples of features that may be used to ensure or otherwise promote proper alignment of end effector (40) with buttress assemblies (100, 110) are described in greater detail below, while other examples will be apparent to those of ordinary skill in the art in view of the teachings herein.

Figure 18:
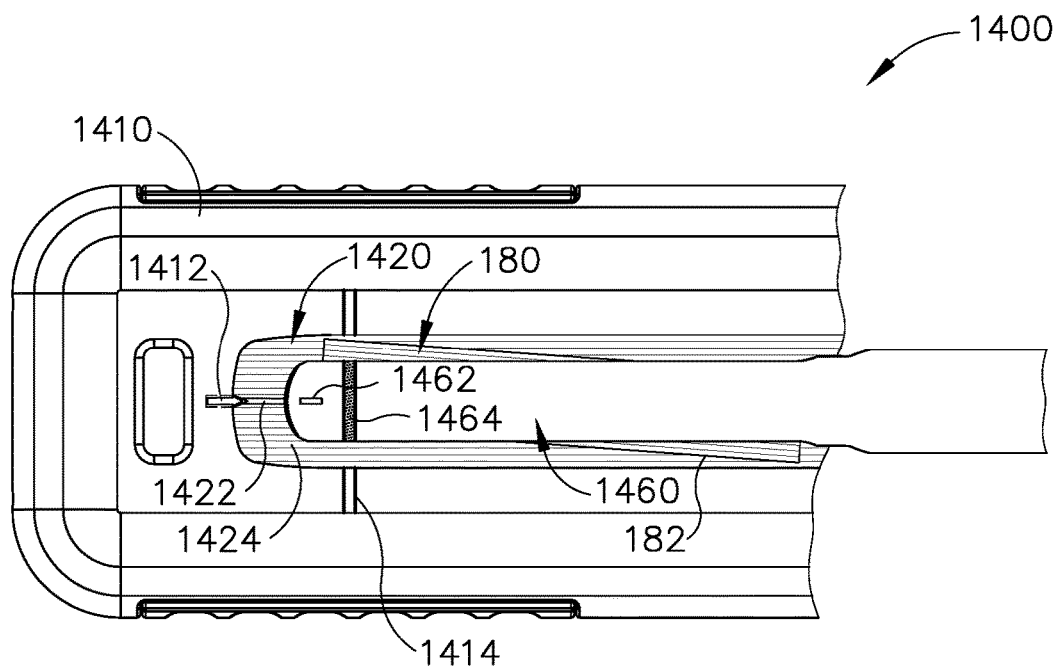
FIG. 18 depicts a top plan view of another exemplary alternative buttress applier cartridge, with a platform of the buttress applier cartridge positioned in the end effector of FIG. 2.

FIG. 18 shows an exemplary buttress applier cartridge (1400) that may be used to support and protect upper and lower buttress assemblies (1420). Cartridge (1400) may also be used to easily load upper and lower buttress assemblies (180) on end effector (40). Cartridge (1400) includes a housing (1410) and a platform (1420) supporting at least one buttress assembly (180). Buttress assembly (180) may be configured and operable just like any other buttress assembly described herein, except for the differences specifically noted below. It should also be understood that buttress assembly (180) may be releasably secured to platform (1420) in accordance with any of the teachings herein relating to securing of buttress assemblies to platforms.

Buttress applier cartridge (1400) is configured to be used with an end effector (40) that incorporates anvil (1460) in place of anvil (60). Anvil (1460) is identical to anvil (60) except that anvil (1460) includes a first marking (1462) and a second marking (1464). First marking (1462) is positioned at the distal end of anvil (1460), extends longitudinally, and is laterally centered along the width of anvil (1460). First marking (1462) is configured to correspond with a first marking (1412) on housing (1410). First marking (1462) is laterally positioned to be centered along the width of the recess in which buttress assembly (180) is disposed. Thus, in order to ensure that anvil (1460) (and, hence, end effector (40)) has proper lateral alignment with cartridge (1400), the operator may view the positions of markings (1412, 1462) in relation to each other to confirm that markings (1412, 1462) are properly aligned with each other.

Second marking (1464) extends cross the width of anvil (1460) and is oriented perpendicularly relative to the longitudinal axis of anvil (1460). Second marking (1464) is configured to correspond with second markings (1414) on housing (1410). Second markings (1414) are located at a predetermined position along the length of the recess in which buttress assembly (180) is disposed. This position is located such that when marking (1464) is aligned with markings (1414), a proper length of buttress assembly (180) and platform (1420) have been received between anvil (1460) and staple cartridge (70). Thus, in order to further ensure that end effector (40) has been advanced to a proper longitudinal position in relation to cartridge (1400), the operator may view the positions of markings (1414, 1464) in relation to each other to confirm that markings (1414, 1464) are properly aligned with each other.

Platform (1420) of the present example further includes markings (1422, 1424) that assist in proper positioning and alignment of end effector (40) relative to cartridge (1400). In particular, platform (1420) includes a marking (1422) in the form of a line that extends longitudinally along the lateral center of platform (1420). Marking (1422) thus aligns with marking (1412) of housing (1410). It should therefore be appreciated that marking (1422) may assist the operator in aligning marking (1462) with marking (1412), such that the operator may observe marking (1422) as representing the same lateral position as marking (1412). It should also be understood that, in versions where marking (1422) is included, marking (1412) may simply be omitted. In addition to including marking (1422), platform (1424) includes markings, which include an array of longitudinally extending lines that are parallel to marking (1422) and that are equidistantly laterally offset from marking (1422). Markings (1422) may assist the operator in achieving a proper yaw orientation of end effector (40) relative to cartridge (1400). In particular, the operator may observe the positioning of the lateral edges of anvil (1460) in relation to markings (1422) to ensure that the lateral edges of anvil (1460) remain parallel with markings (1422).

In addition to helping ensure proper yaw orientation of end effector (40) relative to cartridge (1400), markings (1422) may also help to ensure proper yaw orientation of buttress assembly (180) on platform (1420). In particular, buttress assembly (180) of this example includes a plurality of markings (182) in the form of longitudinally extending lines that are equidistantly spaced apart across the width of buttress assembly (180). In the present example, the spacing of markings (182) is closer than the spacing of markings (1422) to promote easier visualization of buttress assembly (180) on platform (1420), though it should be understood that the spacings may have any other suitable relationship. Markings (182) of buttress assembly (180) may be viewed in relation to markings (1422) of platform (1420) to ensure that markings (182) are parallel with markings (1422). If markings (182) are not parallel with markings (1422) (e.g., as shown in FIG. 18), this may indicate that buttress assembly (180) does not have a proper yaw orientation on platform (1420), such that cartridge (1400) should be discarded.

Figure 19:
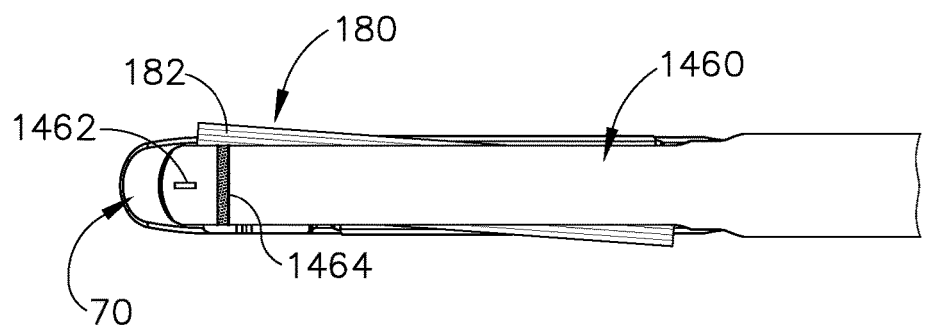
FIG. 19 depicts a top plan view of the end effector of FIG. 2 with a buttress from the buttress applier cartridge of FIG. 18, with the buttress in a skewed position.

Markings (182) of buttress assembly (180) may also be viewed in relation to the lateral edges of anvil (1460) to ensure that buttress assembly (180) has a proper yaw orientation on anvil (1460). As shown in FIG. 19, markings (182) may provide visual emphasis to indicate when buttress assembly (180) does not have proper yaw orientation on anvil (1460). If the operator observes this mis-orientation, the operator by peel buttress assembly (180) away from anvil (1460) and apply another buttress assembly (180) to anvil (1460).

V. Exemplary Features to Indicate Used State of Buttress Applier Cartridge

Some surgical procedures may call for the use of several buttress applier cartridges since end effector (40) may need to be actuated repeatedly in order to complete a surgical task. This may create a scenario in an operating room where spent buttress applier cartridges and unspent buttress applier cartridges are present in the vicinity of each other, causing a potential for inadvertent commingling and confusion. In some cases, an operator may attempt to use an already spent buttress applier cartridge to apply buttress assemblies (100, 110) to an end effector (40); and may fail to realize that the buttress applier cartridge did not in fact have any buttress assemblies (100, 110) loaded on it before the operator then actuates end effector (40) in the patient. It may therefore be desirable to incorporate one or more features into a buttress applier cartridge in order to enable an operator to more readily ascertain whether the buttress applier cartridge has already been used to apply buttress assemblies (100, 110) to an end effector (40). The following discussion provides several merely illustrative examples of features that may be used to readily indicate the spent state of a buttress applier cartridge. Further examples will be apparent to those of ordinary skill in the art in view of the teachings herein.

A. Exemplary Electrically Activated Indicators

Figure 20:
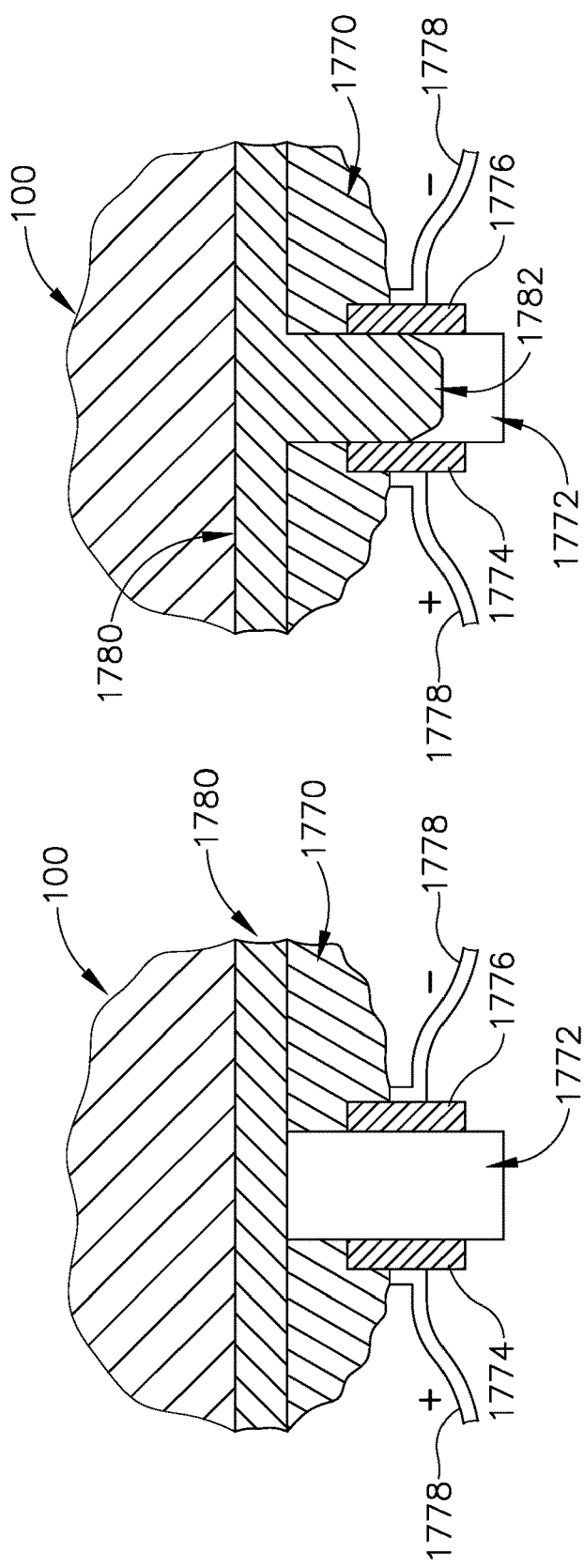
FIG. 20A depicts a cross-sectional detail view of an electrically activated indicator of a buttress applier cartridge, with the indicator in an inactivated state.
FIG. 20B depicts a cross-sectional detail view of the indicator of FIG. 20A, in an activated state.

FIGS. 20A-20B show components that may be readily incorporated into any of the buttress applier cartridges described herein to provide an electrical signal in response to use of the buttress applier cartridge to apply buttress assemblies (100, 110) to an end effector (40). In particular, FIGS. 20A-20B show a base (1770), a layer of medium (1780), and a buttress assembly (100) laid over medium (1780). In some variations, another layer is interposed between buttress assembly (100) and medium (1780). Such an intermediate layer may be substantially non-compressible such that the intermediate layer will efficiently transfer compression forces from buttress assembly (100) to medium (1780) (e.g., when an anvil (60) clamps down on buttress assembly (100)).

Base (1770) may be incorporated into any of the various platforms discussed herein. Medium (1780) of this example comprises a flowable, electrically conductive material. The material forming medium (1780) is configured to maintain a flat structural configuration as shown in FIG. 20A when medium (1780) is not being pressed against base (1770). However, when medium (1780) is pressed against base (1770), such as when an anvil (60) clamps buttress assembly (100) against base (1770) and an underlying platform, medium (1780) will flow into a recess (1772) formed in base (1770) as shown in FIG. 20B. Medium (1780) will then stay in recess (1772).

Various suitable materials that may be used to form medium (1780) will be apparent to those of ordinary skill in the art in view of the teachings herein. By way of example only, medium (1780) may comprise an adhesive material that removably adheres buttress assembly (100) to base (1770). For instance, medium (1780) may comprise PEG blends, PVP/PEG blends, PLC/PGA copolymers, TMC/PGA copolymers, etc., with one or more additives that make the adhesive material electrically conductive. In some versions, medium (1780) comprises the same adhesive material (albeit with electrically conductive material added) that is used to apply buttress assemblies (100, 110) to underside (65) of anvil (60) and deck (73) of staple cartridge (70). By using a similar adhesive material for medium (1780), the flow of medium (1780) into recesses (1772) may occur substantially contemporaneously with the flow of adhesive material forming adhesive layers (102, 112) into the various recesses and other surface features found in underside (65) of anvil (60) and deck (73) of staple cartridge (70). In other words, the flow of medium (1780) into recesses (1772) may be indicative of the flow of adhesive material forming adhesive layers (102, 112) into the various recesses and other surface features found in underside (65) of anvil (60) and deck (73) of staple cartridge (70). Other suitable materials that may be used to form medium (1780) will be apparent to those of ordinary skill in the art in view of the teachings herein.

In the present example, a pair of electrodes (1774, 1776) are fixedly positioned on opposite sides of recess (1772). Electrodes (1774, 1776) include conductive contacts that are exposed to the space within recess (1772). Electrodes (1774, 1776) are coupled with a voltage source (not shown) (e.g., a battery) via wires (1778), such that electrode (1774) provides a positive charge and electrode (1776) provides a negative charge. It should be understood from the foregoing that, it the state shown in FIG. 20A, there is nothing to provide electrical continuity between electrodes (1774, 1776), such that electrical current will not flow through wires (1778). However, once medium (1780) enters recess (1772) as shown in FIG. 20B and thereby provides a path for electrical communication between electrodes (1774, 1776), electrical current will flow through wires (1778).

Various suitable indicator features may be in electrical communication with wires (1778) such that an indicator is electrically activated in response to entry of medium (1780) in recess (1772). By way of example only, such an indicator feature may comprise a light source such as an LED, etc. that is viewable from the exterior of the buttress applier cartridge. In such versions, since the light source is not illuminated until medium (1780) is compressed by closure of anvil (60), the illumination of the light source may provide a clear visual indication that the buttress applier cartridge has already been used to apply buttress assembly (100) to anvil (60). Since medium (1780) will remain in recess (1772), the light source may remain illuminated until the voltage source runs out of power or the circuit is otherwise interrupted. By way of example only, wires (1778) may be in communication with any of the various indicator features described in U.S. patent application Ser. No. 14/926,131, entitled "Surgical Stapler Buttress Applicator with Data Communication," filed on even date herewith, issued as U.S. Pat. No. 10,251,649 on Apr. 9, 2019, the disclosure of which is incorporated by reference herein. Other suitable indicators that may be in communication with wires (1778) to indicate a spent state of a buttress applier cartridge will be apparent to those of ordinary skill in the art in view of the teachings herein.

B. Exemplary Fluid Transfer Indicators

Figure 21:
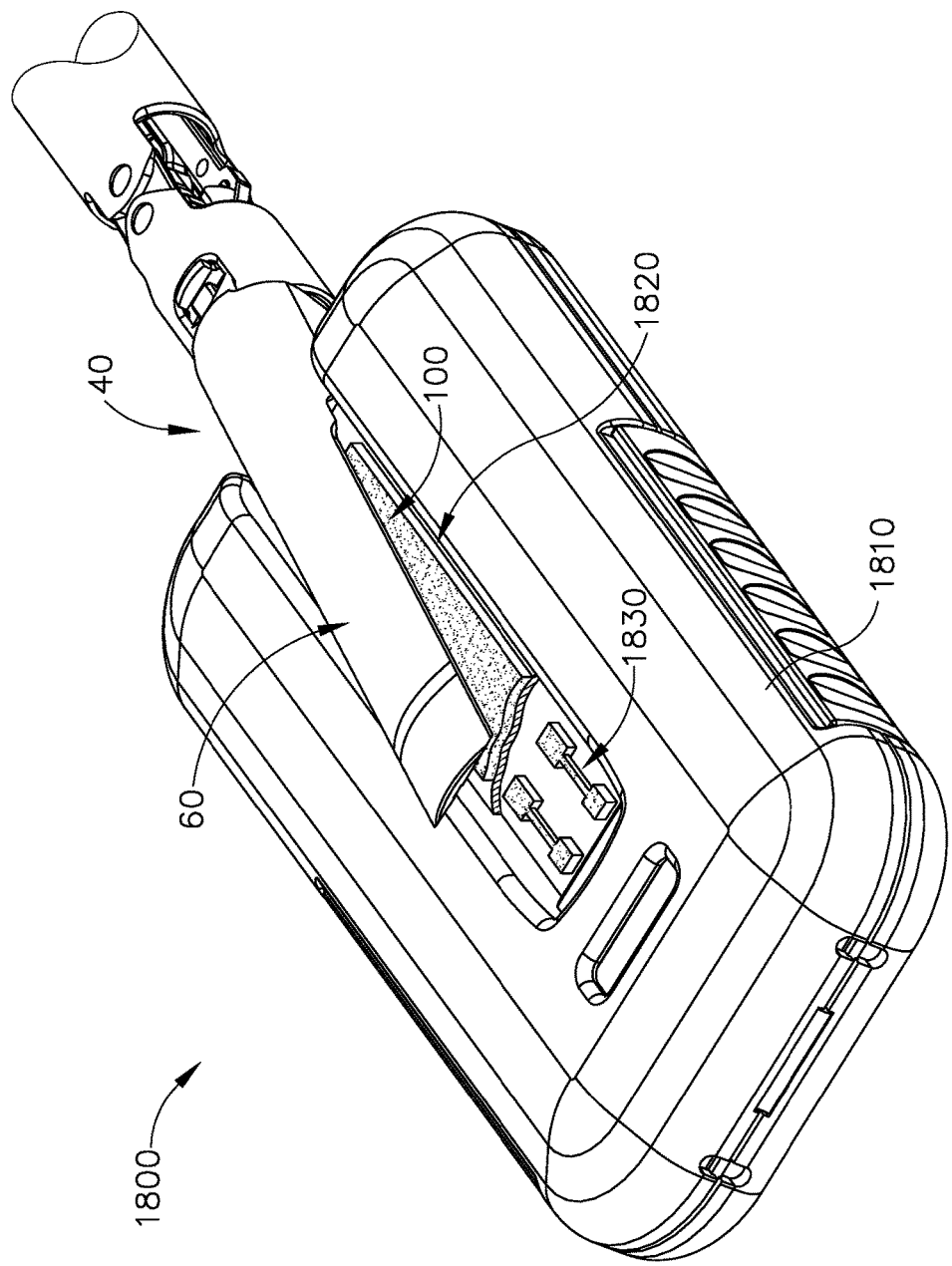
FIG. 21 depicts a perspective view of another exemplary alternative buttress applier cartridge, with a portion of the buttress applier cartridge cut away to reveal internal components, and with a platform positioned in the end effector of FIG. 2 while the end effector is in an open configuration.
Figure 22A:
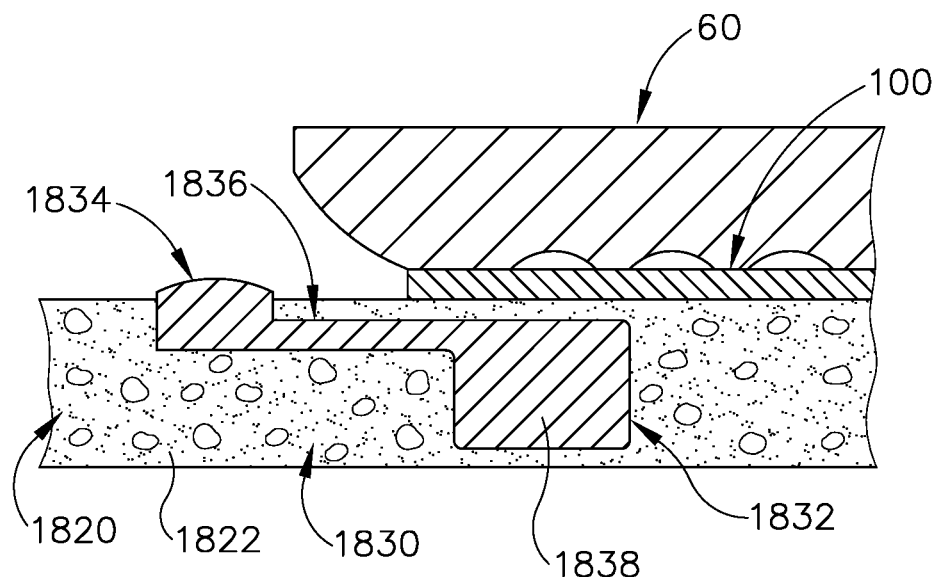
FIG. 22A depicts a cross-sectional detail view of a fluid transfer indicator of the buttress applier cartridge of FIG. 21, with the indicator in a non-actuated state.
Figure 22B:
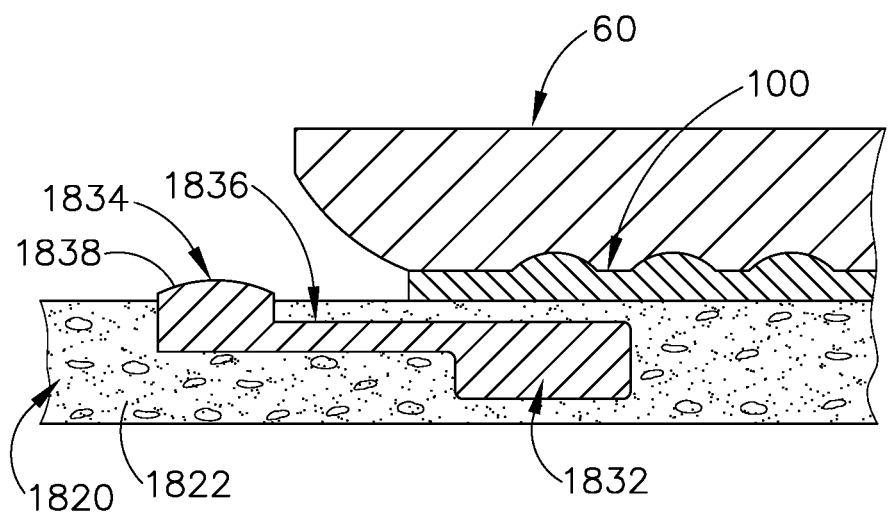
FIG. 22B depicts a cross-sectional detail view of the indicator of FIG. 22A, with the indicator in an actuated state.

FIG. 21 shows another exemplary alternative buttress applier cartridge (1800) that may be used to apply buttress assemblies (100, 110) to an end effector (40). Cartridge (1800) of this example includes a housing (1810) and a platform (1820). Platform (1820) includes a series of indicator assemblies (1830) embedded within the body (1822) of platform (1820). As best seen in FIGS. 22A-22B, each indicator assembly (1830) includes a first reservoir (1832), a second reservoir (1834), and a conduit (1836) extending between reservoirs (1832, 1834). Each set of reservoirs (1832, 1834) and conduit (1836) defines a closed fluid circuit that contains a fixed volume of liquid (1838).

In the present example, body (1822) is formed of a material that is compressible from an expanded thickness (FIG. 22A) to a compressed thickness (FIG. 22B); and is configured to maintain the compressed thickness after body (1822) has been compressed (e.g., even after end effector (40) opens to release platform (1820)). Reservoir (1832) is configured to compress with platform (1820), such that the volume of reservoir (1832) will decrease as platform (1820) is compressed. Reservoir (1834) includes an upper portion that is exposed relative to body (1822), such that an operator may visually observe reservoir (1834). When platform (1820) is in the uncompressed state as shown in FIG. 22A, none of liquid (1838) is positioned in reservoir (1834). As shown in the transition from FIG. 22A to FIG. 22B, some of liquid (1838) will be pressed out of reservoir (1832) when anvil (60) compresses body (1822) of platform (1820). Liquid (1838) will then flow into reservoir (1834). It should be understood that reservoir (1834) may include one or more vent openings (not shown) that will enable air to escape from reservoir (1834) when liquid (1838) is driven into reservoir (1834).

With reservoir (1834) filled with liquid (1838) as shown in FIG. 22B, the operator may readily view the presence of liquid (1838) in reservoir (1834) as a visual indication that the cartridge (1800) has been spent (i.e., that cartridge (1800) no longer has buttress assemblies (100, 110)). Since body (1822) is configured to maintain a compressed state even after platform (1820) is released from end effector (40), liquid (1838) will remain visible in reservoir (1834) to continue indicating that cartridge (1800) has been spent. It should be understood that the materials forming liquid (1838) and body (1822) may be selected to provide a strong contrast, thereby enhancing visibility of liquid (1838) in reservoir (1834).

In addition to providing a visual indication of whether cartridge (1800) has been spent, indicator assemblies (1830) may provide visual feedback to indicate whether the operator has applied sufficient clamping force with end effector (40) in order to successfully transfer buttress assemblies (100, 110) from platform (1820) to end effector (40). In particular, platform (1820) and indicator assemblies (1830) may be configured such that an operator must provide a clamping force with end effector (40) above a certain threshold before liquid (1838) will reach reservoir (1834). Thus, if an operator attempts to clamp end effector (40) on buttress assemblies (100, 110) and platform (1820) yet fails to apply a sufficient clamping force with end effector (40), liquid (1838) will not be driven from reservoir (1832) to reservoir (1834). The operator may thereby determine that the clamping force was insufficient in view of the fact that liquid (1838) is not seen in reservoir (1834). The operator may try again with greater clamping force and then observe reservoir (1834) again for the presence of liquid (1838) to determine whether the additional clamping force was sufficient.

VI. Exemplary Buttress Applier Cartridge with Fluid Capture Reservoir

Figure 23:
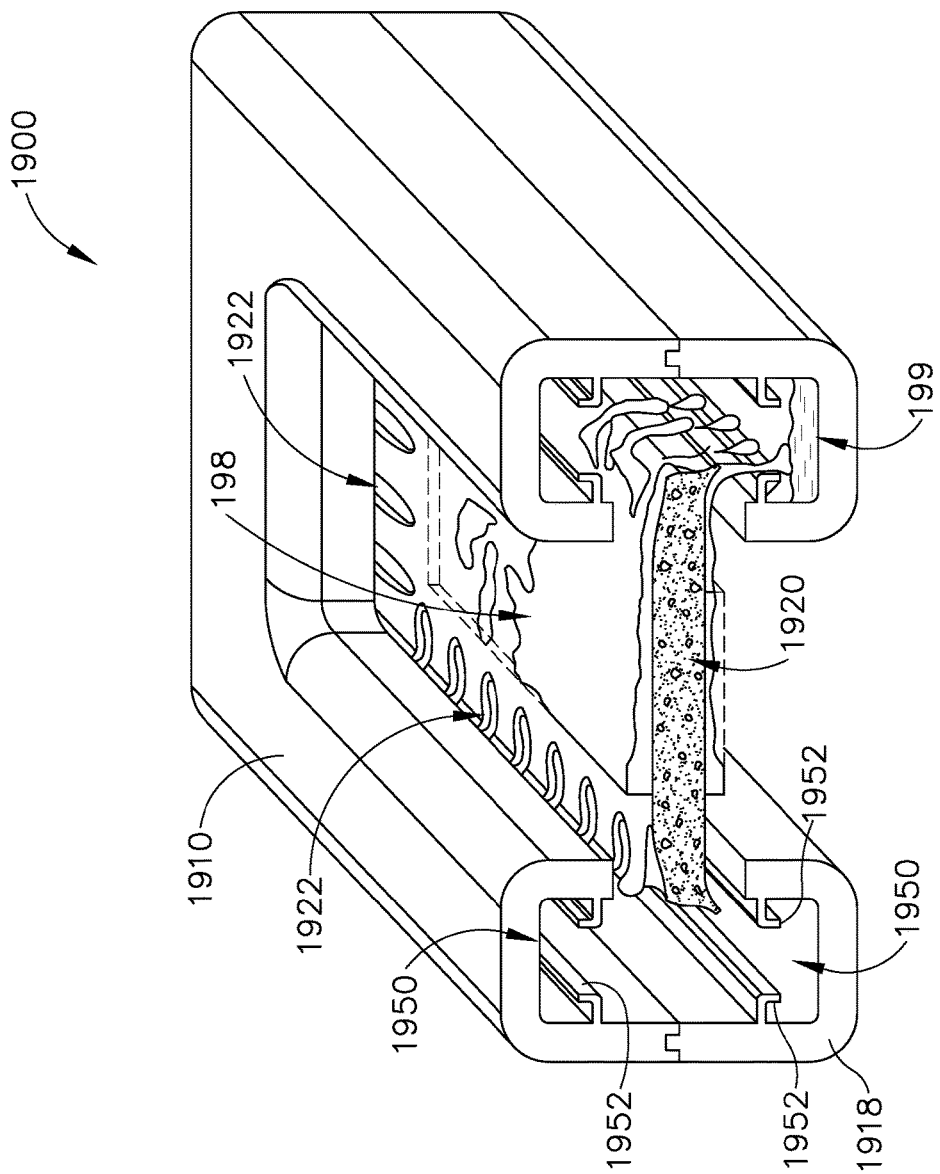
FIG. 23 depicts a perspective cross-sectional view of another exemplary alternative buttress applier cartridge.

Some versions of buttress assemblies (100, 110) may comprise a flowable adhesive material and/or some other flowable material. In some such versions, the flowable material may flow considerably in response to clamping of end effector (40) on buttress assemblies (100, 110), such that the clamping action of end effector (40) drives a flow of adhesive material out from buttress assemblies (100, 110) when end effector (40) clamps down on buttress assemblies (100, 110). It may therefore be desirable to provide features in a buttress applying cartridge to handle excess flowable adhesive material. To that end, FIG. 23 shows an exemplary buttress applier cartridge (1900) that comprises housings (1910, 1918), and a platform (1920). FIG. 23 shows cartridge (1900) in a state where an end effector (40) has already retrieved buttress assemblies (100, 110) from platform (1920), with an excess of flowable material (198) being left on platform (1920). Platform (1920) of this example further comprises a plurality of drainage openings (1922) near the interface regions of housings (1910, 1918). Drainage openings (1922) are in fluid communication with a cavity (1950) that is defined by housings (1910, 1918). Thus, drainage openings (1922) allow the flowable material (198) to drain through drainage openings (1922) and into cavity (1950). The interiors of housings (1910, 1918) further include baffles (1952) in cavity (1950). Baffles (1952) are configured to assist in retaining the excess flowable material (198) in cavity (199). Other suitable features that may be incorporated into a buttress applier cartridge to handle excess flowable materials will be apparent to those of ordinary skill in the art in view of the teachings herein.

As described in greater detail below, some versions of buttress assemblies (100, 110) may be sensitive to certain environmental conditions (e.g., high humidity levels, high temperatures, etc.) such that the effectiveness of buttress assembly (100, 110) may be compromised after buttress assembly (100, 110) has been sufficiently exposed to one or more adverse environmental conditions. In some such versions, flowable material (198) will liquefy in response to sufficient exposure to one or more adverse environmental conditions. If this occurs before buttress assembly (100, 110) is picked up by an end effector (40), flowable material (198) may simply flow off of buttress body (102, 112) and into cavity (199) as described above. In some such instances, buttress assembly (100, 110) may then be rendered inoperable by the absence of flowable material (198). For instance, buttress assembly (100, 110) may be unable to adhere to end effector (40) in the absence of flowable material (198).

VII. Exemplary Packaging for Buttress Applier Cartridge

Figure 24:
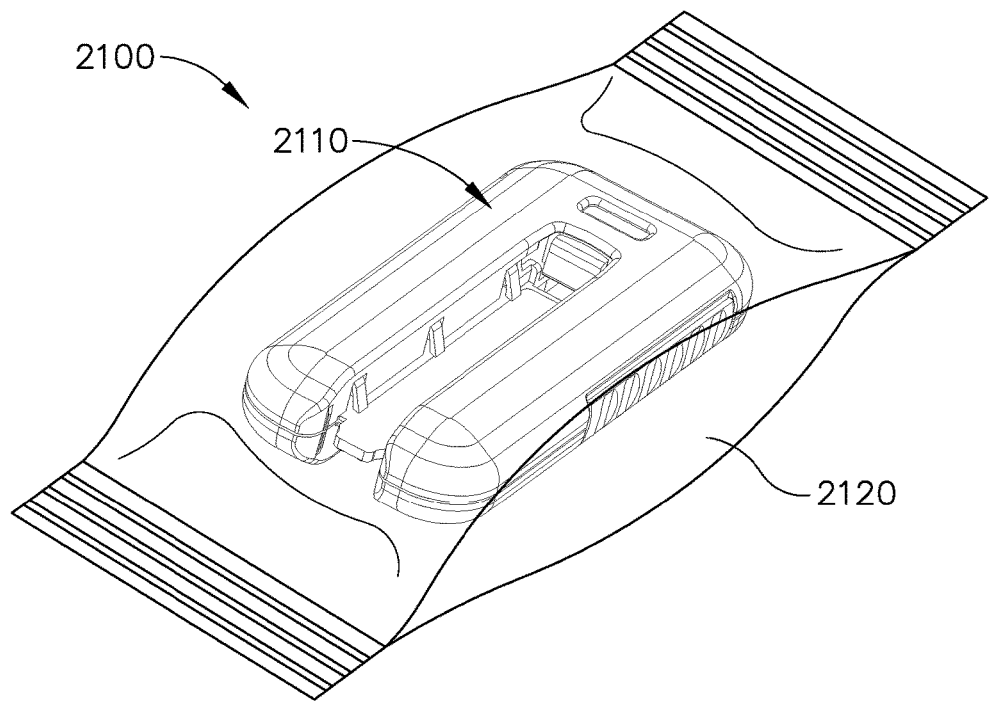
FIG. 24 depicts a perspective view of another exemplary alternative buttress applier cartridge, disposed in a package, with the package in a first state.
Figure 25:
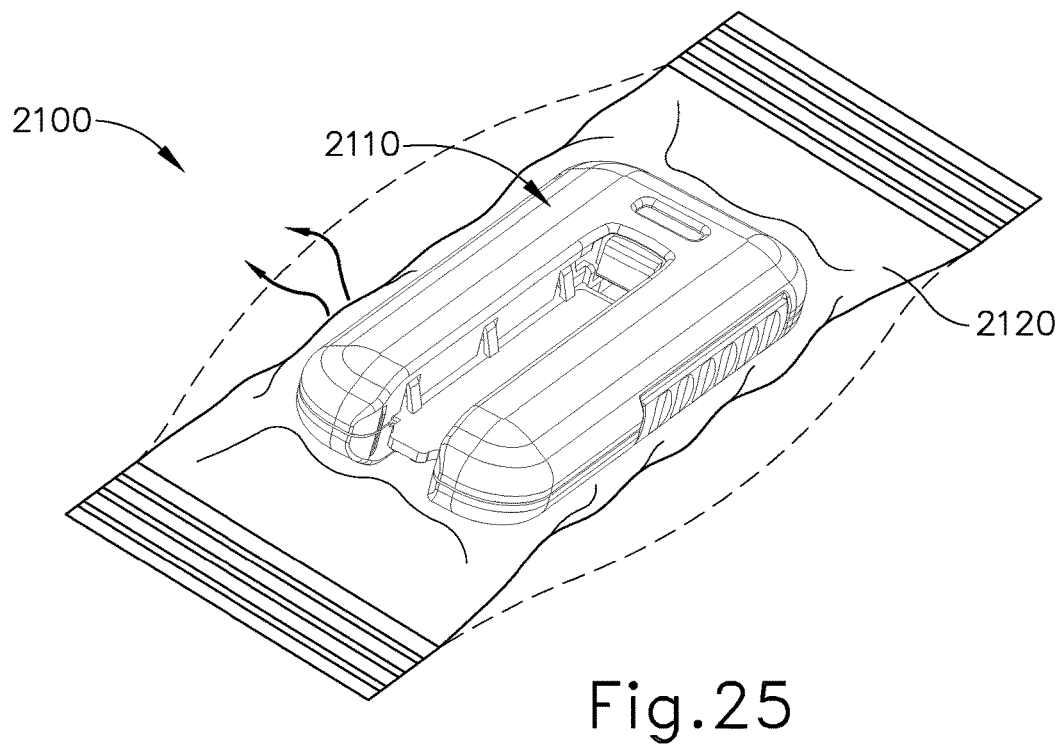
FIG. 25 depicts a perspective view of the buttress applier cartridge and package of FIG. 24, with the package in a second state.

It may be desirable to provide a buttress applier cartridge in a sealed package that maintains the sterility of the buttress applier cartridge. It may also be desirable to configure such packaging in a way that provides an operator with ready indication of whether the seal is being maintain or if the seal has been compromised. To that end, FIGS. 24-25 show a package (2100) comprising a sealed bag (2120) that contains a buttress applier cartridge (2110). Cartridge (2110) may comprise any of the various buttress applier cartridges described herein. As shown in FIG. 24, bag (2120) is filled with air and then sealed, keeping bag (2120) in an inflated state. In the event that the seal is broken, air will escape bag (2120), such that bag (2120) will transition to a deflated state as shown in FIG. 25. An operator may thus readily determine whether the seal of bag (2120) is intact or broken by observing whether bag (2120) is in an inflated state (FIG. 24) or a deflated state (FIG. 25). In some versions, bag (2120) is resiliently biased to conform to the shape of cartridge (2110) or to otherwise shrink in the deflated state, which may make the state of deflation even more readily apparent. It should also be understood that the air that is used to fill bag (2120) may contain a characteristic odor to provide olfactory feedback, such that when the operator opens bag (2120), the operator may observe whether the characteristic odor is present in order to determine whether bag (2120) had maintained a seal before the operator opened bag (2120). Bag (2120) may also provide a popping sound when the operator opens bag (2120), to provide audible feedback to indicate that the seal had been successfully maintained before the operator opened bag (2120). Other suitable ways in which package (2110) may be modified will be apparent to those of ordinary skill in the art in view of the teachings herein.

VIII. Exemplary Features in Buttress Applier Cartridge to React to Environmental Conditions In some instances, it may be desirable to discourage or prevent an operator from loading a buttress assembly (100, 110) onto end effector (40) when that buttress assembly (100, 110) has been exposed to certain environmental conditions that may compromise the effectiveness of buttress assembly (100, 110). For instance, it may be desirable to discourage or prevent an operator from loading a buttress assembly (100, 110) onto end effector (40) when that buttress assembly (100, 110) has been exposed to a humidity level above a certain threshold, other exposure to moisture, a temperature above a certain threshold, and/or some other environmental condition(s) that may compromise the effectiveness of buttress assembly (100, 110). By way of example only, the material forming body (102, 112) may be sensitive to certain environmental conditions in a way such that the effectiveness of body (102, 112) is adversely affected when body (102, 112) is exposed to certain environmental conditions for a prolonged period. Similarly, the material forming adhesive layer (104, 114) may be sensitive to certain environmental conditions in a way such that the effectiveness of adhesive layer (104, 114) is adversely affected when adhesive layer (104, 114) is exposed to certain environmental conditions for a prolonged period. The following examples provide various features that may be incorporated into a buttress applier cartridge in order to discourage or prevent an operator from loading a buttress assembly (100, 110) onto end effector (40) when that buttress assembly (100, 110) has been exposed to certain environmental conditions. It should be understood that the features described below may be readily incorporated into any of the various buttress applier cartridges described herein.

A. Exemplary Features to Control and Visually Indicate Environmental Condition Exposure in Buttress Applier Cartridge One way in which a buttress applier cartridge may discourage an operator from loading a buttress assembly (100, 110) onto end effector (40) when that buttress assembly (100, 110) has been exposed to certain environmental conditions is to provide a visual indication to the operator, indicating to the operator that buttress assembly (100, 110) has been exposed to certain environmental conditions. If such an indicator shows that buttress assemblies (100, 110) have been exposed to certain environmental conditions for prolonged periods, the operator may avoid using those particular buttress assemblies (100, 110). It may also be desirable to incorporate one or more features into a buttress applier cartridge that is/are configured to prevent buttress assemblies (100, 110) from being exposed to certain environmental conditions for prolonged periods. The following examples are provided in the context of excess humidity as an adverse environmental condition, though it should be understood that many of the same teachings may be readily applied to excess temperature as an adverse environmental condition and/or other kinds of adverse environmental conditions.

Figure 26:
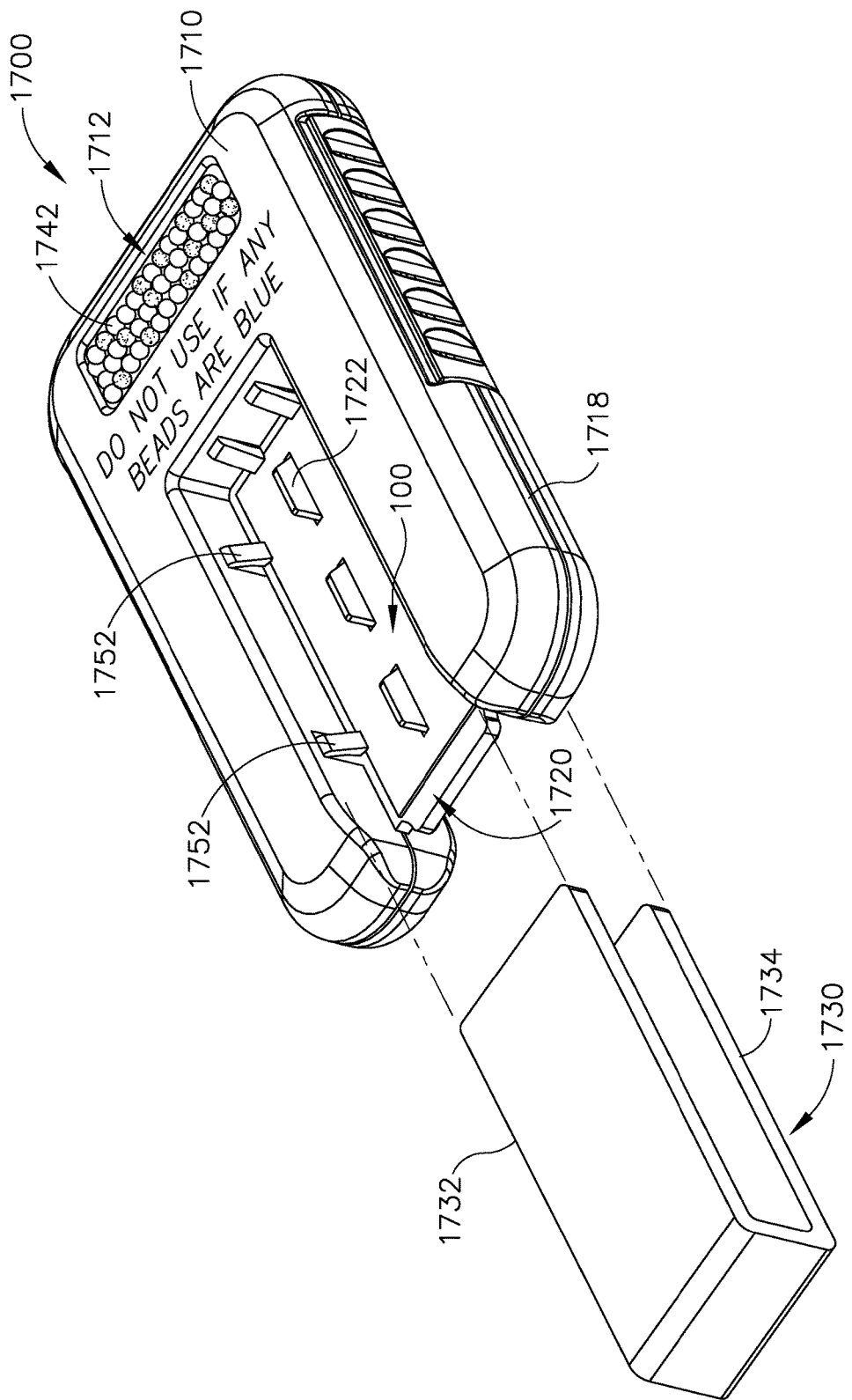
FIG. 26 depicts a perspective view of another exemplary alternative buttress applier cartridge.

FIG. 26 shows an exemplary buttress applier cartridge (1700) that includes housings (1710, 1718), a platform (1720) supporting a buttress assembly (100), and a plurality of retention features (1752). Retention features (1752) are configured to releasably secure buttress assembly (100) to platform (1720); and may be configured like any of the various retention features described herein. Platform (1720) includes a plurality of fins (1722). Fins (1722) are configured to fit within the sidewalls defining channel (62) to ensure that anvil (60) is properly aligned with buttress assembly (100) as anvil (60) is closed down toward buttress assembly (100) and platform (1720). It should also be understood that the underside of platform (1720) (i.e., the side carrying buttress assembly (110), associated with staple cartridge (70)), may also include fins (1722). Fins (1722) on the underside of platform (1720) may be sized and arranged to fit in channel (72) of staple cartridge (70). It should be understood that fins (1722) are merely optional.

Cartridge (1700) of the present example further includes a plurality of indicator beads (1742) that are viewable through a window (1712) formed in housing (1710). Indicator beads (1742) are formed of a color-changing desiccant material. In particular, beads (1742) are configured to reflect a first color when beads (1742) are in a substantially dry state; and a second color when beads (1742) are in a wet state. Beads (1742) may transition to a wet state in response to exposure to humidity that is above a threshold that is suitable for buttress assemblies (100, 110). In some versions, beads (1742) will maintain the second color even if the humidity level later drops back below the threshold level. Beads (1742) will thus provide visual indication to the user to indicate that buttress assemblies (100, 110) have been subject to an unacceptable level of humidity. Of course, beads (1742) may also transition from the first color to the second color if beads (1742) are otherwise exposed to fluid, such as spilled medical fluids, bodily fluids from a patient, etc. Various materials that may be used to form beads (1742) will be apparent to those of ordinary skill in the art in view of the teachings herein. It should also be understood that buttress assemblies (100, 110) may include materials that change color or otherwise change appearance in response to exposure to adverse environmental conditions.

Cartridge (1700) of the present example further includes a cover (1730) that may be removably secured to housings (1710, 1718). Cover (1730) includes an upper panel (1732) and a lower panel (1734) that are coupled together to define a "U" shape. Cover (1730) is sized and configured to cover the recesses in which platform (1720) and buttress assemblies (100, 110) are disposed when cover (1730) is secured to housings (1710, 1718). Cover (1730) may thus protect buttress assemblies (100, 110) up until an operator is ready to use cartridge (1700). To remove cover (1730), the operator may simply pull cover (1730) away from cartridge (1700). By way of example only, panels (1732, 1734) may be resiliently biased toward each other such that panels (1732, 1734) are oriented to be non-parallel with each other. Thus, panels (1732, 1734) may be deflected away from each other to reach a parallel state when cover (1730) is engaged with housings (1710, 1718), such that panels (1732, 1734) resiliently bear against housings (1710, 1718) to provide a secure fit through friction. Various other suitable configurations that may be used to form cover (1730), and to secure cover (1730) to housings (1710, 1718), will be apparent to those of ordinary skill in the art in view of the teachings herein. It should also be understood that cover (1730) may be used with any of the buttress applier cartridges described herein, such that cover (1730) is not at all limited to cartridge (1700).

In some versions, cover (1730) comprises a desiccant material that is configured to absorb moisture (e.g., from humidity) and thereby prevent that moisture from reaching buttress assemblies (100, 110). In addition or in the alternative, desiccant material may be incorporated into the material forming platform (1720), the material forming housing (1710), packets or compartments located within a cavity defined by housing (1710, 1718), and/or in various other suitable locations/configurations. By way of example only, silica gel may be included in packets that are located within a cavity defined by housing (1710, 1718). Other suitable desiccant materials that may be incorporated into cartridge (1700) will be apparent to those of ordinary skill in the art in view of the teachings herein. Similarly, various other ways in which one or more desiccant materials may be incorporated into cartridge (1700) will be apparent to those of ordinary skill in the art in view of the teachings herein.

B. Exemplary Lockout for Buttress Applier Cartridge

Figure 27:
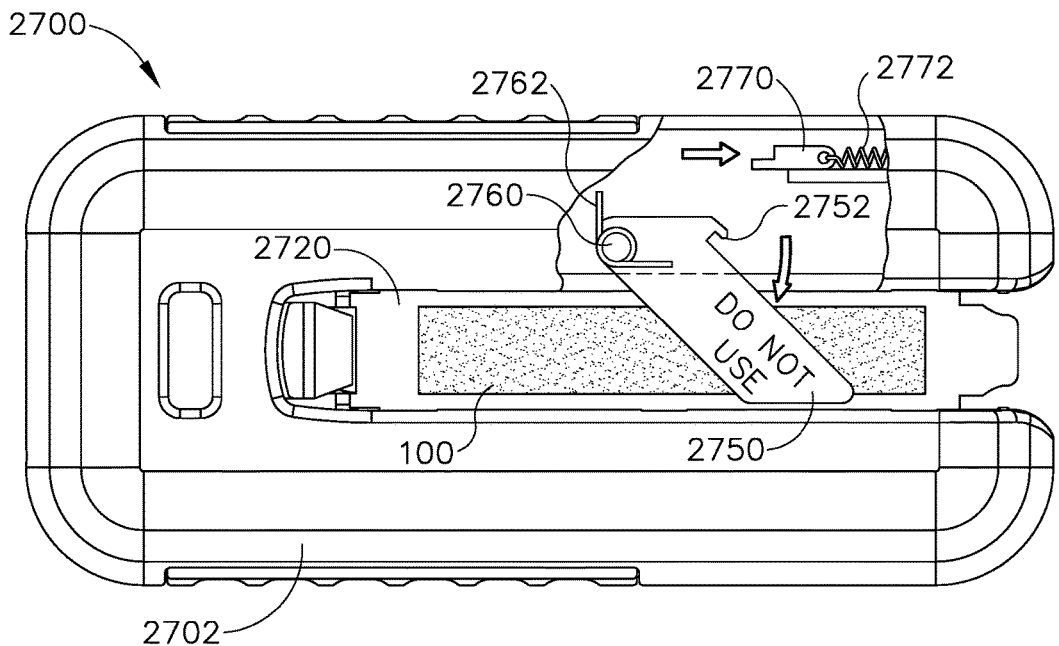
FIG. 27 depicts a top plan view of another exemplary alternative buttress applier cartridge, with a spent cartridge indicator in a deployed position.

In some instances, it may be desirable to physically prevent an operator from loading a buttress assembly (100, 110) onto end effector (40) when that buttress assembly (100, 110) has been exposed to certain environmental conditions that may compromise the effectiveness of buttress assembly (100, 110). For instance, it may be desirable to prevent an operator from loading a buttress assembly (100, 110) onto end effector (40) when that buttress assembly (100, 110) has been exposed to a humidity level above a certain threshold, other exposure to moisture, a temperature above a certain threshold, and/or some other adverse environmental condition(s). To that end, FIG. 27 shows an exemplary alternative buttress applier cartridge (2700) that includes a housing (2702) and a platform (2720) with a buttress assembly (100) disposed on platform (2720). Housing (2702), platform (2720), and buttress assembly (100) may be configured and operable in accordance with any of the various teachings herein. Similarly, buttress assembly (100) may be selectively retained on platform (2720) in accordance with any of the various teachings herein.

Figure 28A:
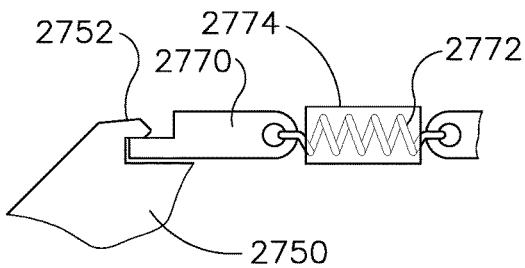
FIG. 28A depicts a partial plan view of the spent cartridge indicator of FIG. 27 in a retracted position and engaged with a retention feature.

Cartridge (2700) of the present example further comprises a lockout panel (2750). Lockout panel (2750) is pivotably coupled with housing (2702) via a pin (2760). A torsion spring (2762) is positioned about pin (2760) and is configured to resiliently bias lockout panel (2750) to the position shown in FIG. 27. In this position, lockout panel (2750) spans the gap defined between the prongs of housing (2702) and thereby covers buttress assembly (100). Lockout panel (2750) thus prevents an end effector (40) from engaging buttress assembly (100) when lockout panel (2750) is in the position shown in FIG. 27. However, lockout panel (2750) may be pivoted away from the position shown in FIG. 27 such that lockout panel (2750) does not cover buttress assembly (100) or otherwise obstruct access to buttress assembly (100) by end effector (40). To selectively hold lockout panel (2750) in a non-blocking position, cartridge (2700) includes a latch (2770). Latch (2770) is coupled with housing (2702) by a coil spring (2772) and is configured to engage a latching feature (2752) of lockout panel (2750) as shown in FIG. 28A. When latch (2770) is engaged with latching feature (2752), latch (2770) is configured to hold lockout panel (2750) in the non-blocking position despite the resilient bias provided by torsion spring (2762).

Figure 28B:
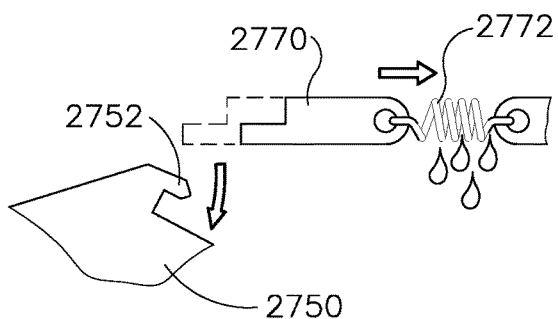
FIG. 28B depicts a partial plan view of the spent cartridge indicator of FIG. 27 in the deployed position and disengaged from the retention feature.

Coil spring (2772) is resiliently biased to assume a compressed configuration. When latch (2770) is engaged with latching feature (2752), coil spring (2772) is in a stretched configuration, such that coil spring (2772) is under stress. To hold coil spring (2772) in the stressed, stretched configuration, a spacing material (2774) is disposed about coil spring. Spacing material (2774) is positioned between coils of coil spring (2772). Under acceptable environmental conditions, spacing material (2774) has sufficient structural integrity to maintain the spacing between the coils of coil spring (2772), thereby maintaining coil spring (2772) in the stressed, stretched configuration, thereby holding lockout panel (2750) in the non-blocking position. However, spacing material (2774) is configured to liquefy and/or otherwise degrade in response to one or more environmental conditions that are adverse to buttress assemblies (100, 110). As shown in FIG. 28B, the liquification or other degradation of spacing material (2774) allows coil spring (2772) to return to a compressed configuration, which will pull latch (2770) out of engagement with latch feature (2752). When latch (2770) is disengaged from latch feature (2752), torsion spring (2762) pivots lockout panel (2750) about pin (2760) to the blocking position as shown in FIG. 27. Thus, cartridge (2700) will prevent the operator from engaging buttress (100) when cartridge (2700) has been exposed to one or more environmental conditions that are adverse to buttress (100). In addition to blocking access to buttress (100), lockout panel (2750) may also include a visual indication (e.g., text reading "do not use," the color red, a stop sign, etc.) to further indicate to the operator that cartridge (2700) has essentially been rendered inoperable.

Those of ordinary skill in the art will recognize that various kinds of materials may be used to form spacing material (2774). By way of example only, spacing material (2774) may comprise wax, PVP (e.g., for humidity sensitivity), PEG (e.g., for temperature sensitivity), and/or any other suitable material(s). It should also be understood that cartridge (2700) may be readily modified to deploy lockout panel (2750) to the blocking position in response to an end effector (40) picking up buttress assembly (100, 110) from platform (2720). Lockout panel (2750) may thus visually indicate to the operator that cartridge (2700) is spent, and may further prevent the operator from clamping end effector on an empty platform (2720). Such functionality may be provided in addition to or in lieu of deployment of lockout panel (2750) in response to adverse environmental conditions.

IX. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a housing defining a gap configured to receive a portion of an end effector of a surgical stapler; (b) a platform, wherein a portion of the platform is exposed in the gap defined by the housing; (c) a first buttress assembly positioned on the platform, wherein the buttress assembly is exposed in the gap defined by the housing; and (d) at least one retainer member configured to selectively retain the first buttress assembly against the platform, wherein the at least one retainer member is further configured to release the first buttress assembly from the platform in response to a clamping action of an end effector positioned in the gap defined by the housing.

Example 2

The apparatus of Example 1, wherein the housing defines a U shape.

Example 3

The apparatus of any one or more of Examples 1 through 2, wherein the platform is formed of a compressible material.

Example 4

The apparatus of any one or more of Examples 1 through 3, wherein the first buttress assembly comprises: (i) a body, and (ii) an adhesive layer

Example 5

The apparatus of Example 4, wherein the adhesive layer is exposed in the gap defined by the housing.

Example 6

The apparatus of any one or more of Examples 1 through 5, further comprising a second buttress assembly, wherein the first buttress assembly is positioned on a first side of the platform, wherein the second buttress assembly is positioned on a second side of the platform.

Example 7

The apparatus of any one or more of Examples 1 through 6, wherein the first buttress assembly comprises: (i) a first longitudinally extending portion, and (ii) a second longitudinally extending portion, wherein the second longitudinally extending portion is laterally spaced apart from the first longitudinally extending portion.

Example 8

The apparatus of Example 7, wherein the second longitudinally extending portion is laterally spaced apart from the first longitudinally extending portion by a distance corresponding to a width of a gap defined by a channel formed in an end effector in a surgical stapler.

Example 9

The apparatus of any one or more of Examples 1 through 8, wherein the housing further comprises a set of end effector alignment features, wherein the end effector alignment features are configured to engage an end effector positioned in the gap defined by the housing to thereby provide lateral alignment and yaw alignment of the end effector relative to the first buttress assembly

Example 10

The apparatus of any one or more of Examples 1 through 9, wherein the at least one retainer member comprises a plurality of fingers, wherein the first buttress assembly comprises an outer region interposed between the plurality of fingers and the platform.

Example 11

The apparatus of Example 10, wherein the fingers are configured to resiliently bear against the first buttress assembly and the platform.

Example 12

The apparatus of any one or more of Examples 1 through 11, wherein the at least one retainer member is configured to move between a first position and a second position, wherein the at least one retainer member configured to selectively retain the first buttress assembly against the platform when the at least one retainer member is in the first position, wherein the at least one retainer is further configured to release the first buttress assembly from the platform when the at least one retainer member is in the second position.

Example 13

The apparatus of Example 12, wherein the first buttress assembly defines a longitudinal axis, wherein the at least one retainer member is configured to move along a path that is transverse to the longitudinal axis to thereby move from the first position to the second position.

Example 14

The apparatus of any one or more of Examples 11 through 12, further comprising a sled member, wherein the sled member is configured to drive the at least one retainer member from the first position to the second position in response to a clamping action of an end effector positioned in the gap defined by the housing.

Example 15

The apparatus of Example 14, wherein the sled member is resiliently biased to drive the at least one retainer member from the first position to the second position.

Example 16

The apparatus of Example 15, further comprising a latch, wherein the latch is configured to engage the housing and the sled member to thereby hold the sled member in a position where the sled member holds the at least one retainer member in the first position, wherein the latch is further configured to disengage the sled member in response to a clamping action of an end effector positioned in the gap defined by the housing to thereby permit the sled member to drive the at least one retainer member from the first position to the second position.

Example 17

The apparatus of Example 16, wherein the latch has a first cam feature and a second cam feature, wherein the first cam feature is positioned and configured to engage an anvil of an end effector positioned in the gap defined by the housing, wherein the second cam feature is positioned and configured to engage a staple cartridge of an end effector positioned in the gap defined by the housing.

Example 18

The apparatus of Example 17, wherein the latch is configured to require clamping engagement of both an anvil against the first cam feature and a staple cartridge against the second cam feature, respectively, in order to disengage the sled member.

Example 19

The apparatus of any one or more of Examples 14 through 18, further comprising a set of pins secured to the at least one retainer member, wherein the sled member defines a set of slots, wherein the pins are disposed in the slots of the sled member, wherein the slots are configured to cooperate with the pins to drive the at least one retainer member to disengage the first buttress assembly in response to movement of the sled member.

Example 20

The apparatus of Example 19, wherein each slot of the set of slots comprises a longitudinally extending portion and an obliquely extending portion.

Example 21

The apparatus of any one or more of Examples 14 through 20, further comprising an indicator member coupled with the sled member, wherein the housing further defines a window, wherein the indicator member and the window are configured such that a first portion of the indicator member is visible through the window when the sled member is positioned to hold the at least one retainer member in the first position, wherein the indicator member and the window are configured such that a second portion of the indicator member is visible through the window when the sled member is actuated to move the at least one retainer member to the second position.

Example 22

The apparatus of any one or more of Examples 14 through 21, wherein the at least one retainer member is configured to move relative to the housing in order to transition from the first position to the second position.

Example 23

The apparatus of Example 22, wherein the at least one retainer member is configured to deform in order to move relative to the housing to thereby transition from the first position to the second position.

Example 24

The apparatus of Example 23, wherein the at least one retainer member comprises an angled cam surface, wherein the cam surface is configured to engage a clamping end effector positioned in the gap defined by the housing and thereby drive the at least one retainer member to deformably move from the first position to the second position in response to clamping forces exerted by the end effector.

Example 25

The apparatus of any one or more of Examples 1 through 24, wherein the housing comprises one or more visual indicators configured to visually indicate an alignment position relative to an end effector positioned in the gap defined by the housing.

Example 26

The apparatus of Example 25, wherein the one or more visual indicators are configured to indicate a yaw alignment position relative to an end effector positioned in the gap defined by the housing.

Example 27

The apparatus of any one or more of Examples 25 through 26, wherein the one or more visual indicators are configured to indicate a longitudinal position alignment relative to an end effector positioned in the gap defined by the housing.

Example 28

The apparatus of any one or more of Examples 25 through 27, wherein the one or more visual indicators are configured to indicate a lateral position alignment relative to an end effector positioned in the gap defined by the housing.

Example 29

The apparatus of any one or more of Examples 1 through 28, wherein the platform comprises one or more visual indicators configured to visually indicate an alignment position relative to an end effector positioned in the gap defined by the housing.

Example 30

The apparatus of Example 29, wherein the one or more visual indicators are configured to indicate a yaw alignment position relative to an end effector positioned in the gap defined by the housing.

Example 31

The apparatus of any one or more of Examples 29 through 30, wherein the one or more visual indicators are configured to indicate a longitudinal position alignment relative to an end effector positioned in the gap defined by the housing.

Example 32

The apparatus of any one or more of Examples 29 through 31, wherein the one or more visual indicators are configured to indicate a lateral position alignment relative to an end effector positioned in the gap defined by the housing.

Example 33

The apparatus of any one or more of Examples 1 through 32, wherein the first buttress assembly comprises one or more visual indicators configured to visually indicate an alignment position relative to an end effector positioned in the gap defined by the housing.

Example 34

The apparatus of Example 33, wherein the one or more visual indicators are configured to indicate a yaw alignment position relative to an end effector positioned in the gap defined by the housing.

Example 35

The apparatus of any one or more of Examples 33 through 34, wherein the one or more visual indicators are configured to indicate a yaw alignment position relative to the platform.

Example 36

The apparatus of any one or more of Examples 33 through 35, wherein the one or more visual indicators are configured to indicate a lateral position alignment relative to an end effector positioned in the gap defined by the housing.

Example 37

The apparatus of any one or more of Examples 33 through 36, wherein the one or more visual indicators are configured to indicate a lateral position alignment relative to the platform.

Example 38

The apparatus of any one or more of Examples 1 through 37, further comprising: (a) a flowable material interposed between the platform and the first buttress assembly, wherein the platform defines an recess, wherein the flowable material is configured to flow into the recess in response to compression of the first buttress assembly toward the platform, wherein the flowable material is electrically conductive; and (b) a pair of electrodes separated by the recess, wherein the flowable material is configured to provide a path for electrical continuity between the electrodes when the flowable material is driven into the recess.

Example 39

The apparatus of any one or more of Examples 1 through 38, further comprising an indicator assembly, wherein the indicator assembly comprises: (i) a first fluid chamber, wherein the first fluid chamber is embedded within the platform, (ii) a second fluid chamber, wherein at least a portion of the second fluid chamber is visible through the platform, (iii) a conduit coupling the first fluid chamber with the second fluid chamber, and (iv) a fluid disposed in the first fluid chamber, wherein the platform is configured to transition from a non-compressed state to a compressed state, wherein the indicator assembly is configured to provide the fluid in the first fluid chamber when the platform is in the non-compressed state such that the fluid is not visible in the second fluid chamber when the platform is in the non-compressed state, wherein the indicator assembly is further configured such that the fluid is driven into the second fluid chamber when the platform is compressed to the compressed state such that the fluid is visible in the second fluid chamber when the platform is in the compressed state.

Example 40

The apparatus of any one or more of Examples 1 through 39, wherein the platform comprises one or more openings configured to provide fluid drainage through the platform.

Example 41

The apparatus of Example 40, wherein the housing defines a cavity in fluid communication with the openings of the platform, wherein the cavity is configured to receive and retain fluid communicated through the openings of the platform.

Example 42

The apparatus of any one or more of Examples 1 through 41, further comprising a bag, wherein the housing, the platform, the first buttress assembly, and the at least one retainer are contained within the bag, wherein the bag is sealed.

Example 43

The apparatus of Example 42, wherein the bag further comprises a pressurized gas.

Example 44

The apparatus of Example 43, the wherein the pressurized gas is scented such that the pressurized gas is configured to provide olfactory feedback indicating the state of the bag in response to opening of the bag.

Example 45

An apparatus comprising: (a) a housing defining a gap configured to receive a portion of an end effector of a surgical stapler; (b) a platform, wherein a portion of the platform is exposed in the gap defined by the housing; (c) a buttress assembly positioned on the platform, wherein the buttress assembly is exposed in the gap defined by the housing; (d) at least one retainer member configured to selectively retain the buttress assembly against the platform, wherein the at least one retainer member is further configured to release the buttress assembly from the platform in response to a clamping action of an end effector positioned in the gap defined by the housing; and (e) an indicator, wherein the indicator is configured to provide indication of a state of one or both of the buttress assembly or the at least one retainer member, wherein the indicator is further configured to change state in response to a change of state of one or both of the buttress assembly or the at least one retainer member.

Example 46

The apparatus of Example 45, wherein the indicator is configured to move concomitantly with the at least one retainer member.

Example 47

The apparatus of Example 46, wherein the housing defines a window, wherein a first portion of the indicator is viewable through the window when the at least one retainer member is positioned to retain the first buttress assembly against the platform, wherein a second portion of the indicator is viewable through the window when the at least one retainer member is positioned to release the first buttress assembly from the platform.

Example 48

The apparatus of Example 47, wherein the first portion of the indicator has a first color, wherein the second portion of the indicator has a second color.

Example 49

The apparatus of any one or more of Examples 45 though 48, further comprising a boss, wherein the boss is fixedly positioned relative to the housing, wherein the indicator is configured to strike the boss in response to the at least one retainer member releasing the buttress assembly from the platform, wherein the indicator and the boss are configured to provide feedback that is one or both of audible or tactile when the indicator strikes the boss.

Example 50

The apparatus of any one or more of Examples 45 though 49, wherein the indicator is incorporated into the platform.

Example 51

The apparatus of Example 50, wherein the indicator comprises a first region of the platform having a first color, wherein the buttress is positioned over the first region such that the buttress obscures the first region and such that the first region is viewable in response to removal of the buttress from the platform, wherein the platform further includes a second region adjacent to the first region, wherein the second region has a second color.

Example 52

The apparatus of claim 1, wherein the housing comprises one or more alignment indicators, wherein the one or more alignment indicators are configured to indicate one or more of a yaw alignment position relative to an end effector positioned in the gap defined by the housing, a longitudinal position alignment relative to an end effector positioned in the gap defined by the housing, or a lateral position alignment relative to an end effector positioned in the gap defined by the housing.

Example 53

The apparatus of any one or more of Examples 45 though 52, wherein the platform comprises one or more alignment indicators, wherein the one or more alignment indicators are configured to indicate one or more of a yaw alignment position relative to an end effector positioned in the gap defined by the housing, a longitudinal position alignment relative to an end effector positioned in the gap defined by the housing, or a lateral position alignment relative to an end effector positioned in the gap defined by the housing.

Example 54

The apparatus of any one or more of Examples 45 though 53, wherein the buttress assembly comprises one or more alignment indicators, wherein the one or more alignment indicators are configured to indicate one or more of a yaw alignment position relative to one or both of an end effector positioned in the gap defined by the housing or the platform, a lateral position alignment relative to an end effector positioned in the gap defined by the housing, or a lateral position alignment relative to the platform.

Example 55

The apparatus of any one or more of Examples 45 though 54, wherein the indicator comprises: (i) a flowable material interposed between the platform and the first buttress assembly, wherein the platform defines an recess, wherein the flowable material is configured to flow into the recess in response to compression of the first buttress assembly toward the platform, wherein the flowable material is electrically conductive, and (ii) a pair of electrodes separated by the recess, wherein the flowable material is configured to provide a path for electrical continuity between the electrodes when the flowable material is driven into the recess.

Example 56

The apparatus of any one or more of Examples 45 though 55, wherein the indicator comprises: (i) a first fluid chamber, wherein the first fluid chamber is embedded within the platform, (ii) a second fluid chamber, wherein at least a portion of the second fluid chamber is visible through the platform, (iii) a conduit coupling the first fluid chamber with the second fluid chamber, and (iv) a fluid disposed in the first fluid chamber, wherein the platform is configured to transition from a non-compressed state to a compressed state, wherein the indicator assembly is configured to provide the fluid in the first fluid chamber when the platform is in the non-compressed state such that the fluid is not visible in the second fluid chamber when the platform is in the non-compressed state, wherein the indicator is further configured such that the fluid is driven into the second fluid chamber when the platform is compressed to the compressed state such that the fluid is visible in the second fluid chamber when the platform is in the compressed state.

Example 57

The apparatus of any one or more of Examples 45 though 56, further comprising a bag, wherein the housing, the platform, the first buttress assembly, and the at least one retainer are contained within the bag, wherein the bag is sealed, wherein the bag further comprises a pressurized gas, wherein the pressurized gas is scented such that the pressurized gas is configured to provide olfactory feedback indicating the state of the bag in response to opening of the bag.

Example 58

The apparatus of any one or more of Examples 45 though 57, further comprising an environmental condition indicator, wherein the environmental condition indicator is configured to indicate exposure of the buttress assembly to one or more predetermined environmental conditions.

Example 59

The apparatus of any one or more of Examples 45 though 58, further comprising a blocking member movably coupled with the housing, wherein the blocking member is configured to transition from a non-blocking position to a blocking position, wherein the blocking member is configured to block access to the buttress assembly by an end effector when the blocking member is in the blocking position, wherein the blocking member is configured to permit access to the buttress assembly by an end effector when the blocking member is in the non-blocking position.

Example 60

The apparatus of Example 59, wherein the blocking member is resiliently biased toward the blocking position, the apparatus further comprising a latch member configured to selectively prevent the blocking member from moving from the blocking position to the non-blocking position.

Example 61

The apparatus of Example 60, wherein the latch member is configured to permit the blocking member to move to the blocking position in response to exposure to one or more predetermined environmental conditions.

Example 62

The apparatus of any one or more of Examples 45 though 61, wherein the platform comprises one or more openings configured to provide fluid drainage through the platform, wherein the housing defines a cavity in fluid communication with the openings of the platform, wherein the cavity is configured to receive and retain fluid communicated through the openings of the platform.

Example 63

An apparatus comprising: (a) a housing defining a gap configured to receive a portion of an end effector of a surgical stapler, wherein the housing defines an indicator window; (b) a platform, wherein a portion of the platform is exposed in the gap defined by the housing; (c) a buttress assembly positioned on the platform, wherein the buttress assembly is exposed in the gap defined by the housing; (d) at least one retainer member configured to selectively retain the buttress assembly against the platform, wherein the at least one retainer member is further configured to release the buttress assembly from the platform in response to a clamping action of an end effector positioned in the gap defined by the housing; and (e) an indicator, wherein the indicator is positioned to be viewed through the indicator window of the housing, wherein the indicator is configured to provide at least one of visual feedback, audible feedback, or tactile feedback indicating release of the buttress assembly from the platform by the at least one retainer member.

Example 64

A method of securing a buttress assembly to an end effector of a surgical instrument, wherein the end effector comprises an upper jaw portion and a lower jaw portion, the method comprising: (a) positioning the end effector about a platform while the upper and lower jaw portions are in an open configuration, wherein the buttress assembly is supported by the platform during the act of positioning the end effector about the platform; (b) transitioning the end effector such that the upper and lower jaw portions are in a closed configuration, thereby closing the end effector on the buttress assembly and the platform; and (c) changing a state of an indicator in response to the act of transitioning the end effector such that the upper and lower jaw portions are in a closed configuration, wherein the indicator is transitioned to indicate capture of the buttress assembly by the end effector.

X. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

In addition to the foregoing, it should also be understood that any of the various buttress assemblies described herein may be further constructed and operable in accordance with at least some of the teachings of U.S. patent application Ser. No. 14/667,842, entitled "Method of Applying a Buttress to a Surgical Stapler," filed Mar. 25, 2015, published as U.S. Pub. No. 2016/0278774 on Sep. 29, 2016, the disclosure of which is incorporated by reference herein; U.S. patent application Ser. No. 14/827,856, entitled "Implantable Layers for a Surgical Instrument," filed Aug. 17, 2015, published as U.S. Pub. No. 2017/0049444 on Frb. 23, 2017, the disclosure of which is incorporated by reference herein; U.S. patent application Ser. No. 14/871,071, entitled "Compressible Adjunct with Crossing Spacer Fibers," filed Sep. 30, 2015, published as U.S. Pub. No. 2017/0086837 on Mar. 30, 2017, the disclosure of which is incorporated by reference herein; and U.S. patent application Ser. No. 14/871,131, entitled "Method for Applying an Implantable Layer to a Fastener Cartridge," filed Sep. 30, 2015, published as U.S. Pub. No. 2017/0086842 on Mar. 30, 2017 the disclosure of which is incorporated by reference herein. Furthermore, in addition to the methods described herein, any of the various buttress assemblies described herein may be applied to end effector (40) in accordance with at least some of the teachings of U.S. Provisional Patent App. No. 62/209,041, entitled "Method and Apparatus for Applying a Buttress to End Effector of a Surgical Stapler," filed Aug. 24, 2015, the disclosure of which is incorporated by reference herein; and/or U.S. patent application Ser. No. 14/871,131, entitled "Method for Applying an Implantable Layer to a Fastener Cartridge," filed Sep. 30, 2015, published as U.S. Pub. No. 2017/0086842 on Mar. 30, 2017, the disclosure of which is incorporated by reference herein. Various suitable ways in which the teachings herein may be combined with various teachings of the above-cited references will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, issued as U.S. Pat. No. 8,844,789 on Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, issued as U.S. Pat. No. 8,820,605 on Sep. 2, 2014, the disclosure of which is incorporated by reference herein; U.S. Pub. No. 2012/0132450, entitled "Shiftable Drive Interface for Robotically-Controlled Surgical Tool," published May 31, 2012, issued as U.S. Pat. No. 8,616,431 on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, issued as U.S. Pat. No. 8,573,461 on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued as U.S. Pat. No. 8,602,288 on Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, issued as U.S. Pat. No. 9,301,759 on Apr. 5, 2016, the disclosure of which is incorporated by reference herein; U.S. Pub. No. 2012/0203247, entitled "Robotically-Controlled Surgical End Effector System," published Aug. 9, 2012, issued as U.S. Pat. No. 8,783,541 on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012issued as U.S. Pat. No. 8,479,696 on Jul. 9, 2013; U.S. Pub. No. 2012/0138660, entitled "Robotically-Controlled Cable-Based Surgical End Effectors," published Jun. 7, 2012, issued as U.S. Pat. No. 8,800,839 on Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, issued as U.S. Pat. No. 8,573,465 on Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus comprising:
   (a) a housing defining a gap configured to receive a portion of an end effector of a surgical stapler;
   (b) a platform, wherein a portion of the platform is exposed in the gap defined by the housing;
   (c) a buttress assembly positioned on the platform, wherein the buttress assembly is exposed in the gap defined by the housing;
   (d) at least one retainer member configured to selectively retain the buttress assembly against the platform, wherein the at least one retainer member is further configured to release the buttress assembly from the platform in response to a clamping action of an end effector positioned in the gap defined by the housing; and
   (e) an indicator, wherein the indicator is configured to provide indication of a state of one or both of the buttress assembly or the at least one retainer member, wherein the indicator is further configured to change state in response to a change of state of one or both of the buttress assembly or the at least one retainer member, wherein an upper surface of the housing defines a window that is configured to change colors from a first color to a second color in response to the change of state of one or both of the buttress assembly or the at least one retainer member.

2. The apparatus of claim 1, wherein the indicator is configured to move concomitantly with the at least one retainer member.

3. The apparatus of claim 2, wherein a first portion of the indicator is viewable through the window when the at least one retainer member is positioned to retain the first buttress assembly against the platform, wherein a second portion of the indicator is viewable through the window when the at least one retainer member is positioned to release the first buttress assembly from the platform.

4. The apparatus of claim 3, wherein the first portion of the indicator has the first color, wherein the second portion of the indicator has the second color.

5. The apparatus of claim 1, further comprising a boss, wherein the boss is fixedly positioned relative to the housing, wherein the indicator is configured to strike the boss in response to the at least one retainer member releasing the buttress assembly from the platform, wherein the indicator and the boss are configured to provide feedback that is one or both of audible or tactile when the indicator strikes the boss.

6. The apparatus of claim 1, wherein the indicator is incorporated into the platform.

7. The apparatus of claim 6, wherein the indicator comprises a first region of the platform having a first color, wherein the buttress is positioned over the first region such that the buttress obscures the first region and such that the first region is viewable in response to removal of the buttress from the platform, wherein the platform further includes a second region adjacent to the first region, wherein the second region has a second color.

8. The apparatus of claim 1, wherein the housing comprises one or more alignment indicators, wherein the one or more alignment indicators are configured to indicate one or more of a yaw alignment position relative to an end effector positioned in the gap defined by the housing, a longitudinal position alignment relative to an end effector positioned in the gap defined by the housing, or a lateral position alignment relative to an end effector positioned in the gap defined by the housing.

9. The apparatus of claim 1, wherein the platform comprises one or more alignment indicators, wherein the one or more alignment indicators are configured to indicate one or more of a yaw alignment position relative to an end effector positioned in the gap defined by the housing, a longitudinal position alignment relative to an end effector positioned in the gap defined by the housing, or a lateral position alignment relative to an end effector positioned in the gap defined by the housing.

10. The apparatus of claim 1, wherein the buttress assembly comprises one or more alignment indicators, wherein the one or more alignment indicators are configured to indicate one or more of a yaw alignment position relative to one or both of an end effector positioned in the gap defined by the housing or the platform, a lateral position alignment relative to an end effector positioned in the gap defined by the housing, or a lateral position alignment relative to the platform.

11. The apparatus of claim 1, wherein the indicator comprises:
   (i) a flowable material interposed between the platform and the first buttress assembly, wherein the platform defines an recess, wherein the flowable material is configured to flow into the recess in response to compression of the first buttress assembly toward the platform, wherein the flowable material is electrically conductive, and
   (ii) a pair of electrodes separated by the recess, wherein the flowable material is configured to provide a path for electrical continuity between the electrodes when the flowable material is driven into the recess.

12. The apparatus of claim 1, wherein the indicator comprises:
   (i) a first fluid chamber, wherein the first fluid chamber is embedded within the platform,
   (ii) a second fluid chamber, wherein at least a portion of the second fluid chamber is visible through the platform,
   (iii) a conduit coupling the first fluid chamber with the second fluid chamber, and
   (iv) a fluid disposed in the first fluid chamber,
   wherein the platform is configured to transition from a non-compressed state to a compressed state, wherein the indicator assembly is configured to provide the fluid in the first fluid chamber when the platform is in the non-compressed state such that the fluid is not visible in the second fluid chamber when the platform is in the non-compressed state, wherein the indicator is further configured such that the fluid is driven into the second fluid chamber when the platform is compressed to the compressed state such that the fluid is visible in the second fluid chamber when the platform is in the compressed state.

13. The apparatus of claim 1, further comprising a bag, wherein the housing, the platform, the first buttress assembly, and the at least one retainer are contained within the bag, wherein the bag is sealed, wherein the bag further comprises a pressurized gas, wherein the pressurized gas is scented such that the pressurized gas is configured to provide olfactory feedback indicating the state of the bag in response to opening of the bag.

14. The apparatus of claim 1, further comprising an environmental condition indicator, wherein the environmental condition indicator is configured to indicate exposure of the buttress assembly to one or more predetermined environmental conditions.

15. An apparatus comprising:
(a) a housing defining a gap configured to receive a portion of an end effector of a surgical stapler;
(b) a platform, wherein a portion of the platform is exposed in the gap defined by the housing;
(c) a buttress assembly positioned on the platform, wherein the buttress assembly is exposed in the gap defined by the housing;
(d) at least one retainer member configured to selectively retain the buttress assembly against the platform, wherein the at least one retainer member is further configured to release the buttress assembly from the platform in response to a clamping action of an end effector positioned in the gap defined by the housing;
(e) an indicator, wherein the indicator is configured to provide indication of a state of one or both of the buttress assembly or the at least one retainer member, wherein the indicator is further configured to change state in response to a change of state of one or both of the buttress assembly or the at least one retainer member, and
(f) a blocking member movably coupled with the housing, wherein the blocking member is configured to transition from a non-blocking position to a blocking position, wherein the blocking member is configured to block access to the buttress assembly by an end effector when the blocking member is in the blocking position, wherein the blocking member is configured to permit access to the buttress assembly by an end effector when the blocking member is in the non-blocking position.

16. The apparatus of claim 15, wherein the blocking member is resiliently biased toward the blocking position, the apparatus further comprising a latch member configured to selectively prevent the blocking member from moving from the blocking position to the non-blocking position.

17. The apparatus of claim 16, wherein the latch member is configured to permit the blocking member to move to the blocking position in response to exposure to one or more predetermined environmental conditions.

18. The apparatus of claim 1, wherein the platform comprises one or more openings configured to provide fluid drainage through the platform, wherein the housing defines a cavity in fluid communication with the openings of the platform, wherein the cavity is configured to receive and retain fluid communicated through the openings of the platform.

19. The apparatus of claim 1, wherein the window is configured to reflect the first color when the indicator is in a substantially dry state and switch to the second color when the indicator is in a wet state.

20. An apparatus comprising:
(a) a housing defining a gap configured to receive a portion of an end effector of a surgical stapler;
(b) a platform, wherein a portion of the platform is exposed in the gap defined by the housing;
(c) a buttress assembly positioned on the platform, wherein the buttress assembly is exposed in the gap defined by the housing;
(d) at least one retainer member configured to selectively retain the buttress assembly against the platform, wherein the at least one retainer member is further configured to release the buttress assembly from the platform in response to a clamping action of an end effector positioned in the gap defined by the housing; and
(e) an indicator, wherein the indicator is configured to provide indication of a state of one or both of the buttress assembly or the at least one retainer member, wherein the indicator is further configured to change state in response to a change of state of one or both of the buttress assembly or the at least one retainer member, wherein the indicator further comprises at least one of:
(i) a flowable material interposed between the platform and the first buttress assembly, wherein the platform defines an recess, wherein the flowable material is configured to flow into the recess in response to compression of the first buttress assembly toward the platform, wherein the flowable material is electrically conductive, and
(ii) a pair of electrodes separated by the recess, wherein the flowable material is configured to provide a path for electrical continuity between the electrodes when the flowable material is driven into the recess;
or
(i) a first fluid chamber, wherein the first fluid chamber is embedded within the platform,
(ii) a second fluid chamber, wherein at least a portion of the second fluid chamber is visible through the platform,
(iii) a conduit coupling the first fluid chamber with the second fluid chamber, and
(iv) a fluid disposed in the first fluid chamber,
wherein the platform is configured to transition from a non-compressed state to a compressed state, wherein the indicator assembly is configured to provide the fluid in the first fluid chamber when the platform is in the non-compressed state such that the fluid is not visible in the second fluid chamber when the platform is in the non-compressed state, wherein the indicator is further configured such that the fluid is driven into the second fluid chamber when the platform is compressed to the compressed state such that the fluid is visible in the second fluid chamber when the platform is in the compressed state.

* * * * *